United States Patent
Day et al.

(10) Patent No.: US 10,695,491 B2
(45) Date of Patent: Jun. 30, 2020

(54) DRUG DELIVERY DEVICE INCLUDING MOTION DETECTION SYSTEM

(71) Applicant: Sanofi-Aventis Deutschland GmbH, Frankfurt am Main (DE)

(72) Inventors: Shane Alistair Day, Warwick (GB); Daniel Thomas De Sausmarez Lintell, Rugby (GB); Steven Wimpenny, Leamington Spa (GB); Christopher Jones, Tewkesbury (GB); Aidan Michael O'Hare, Kenilworth (GB); Barry Yates, Kenilworth (GB); Robert Frederick Veasey, Leamington Spa (GB); Christopher James Smith, Cheshire (GB); Malcolm Boyd, Wellsbourne (GB); David Martin Leak, Lake Hopatcong, NJ (US); Carmen Patricia Keating, Nowendoc (AU); David Sanders, Warwick (GB); Elizabeth Anne Marshall, Leamington Spa (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 16/598,882

(22) Filed: Oct. 10, 2019

(65) Prior Publication Data

US 2020/0030533 A1     Jan. 30, 2020

Related U.S. Application Data

(63) Continuation of application No. 16/512,127, filed on Jul. 15, 2019, which is a continuation of application
(Continued)

(30) Foreign Application Priority Data

Dec. 17, 2009 (EP) .................................... 09179724

(51) Int. Cl.
*A61M 5/19* (2006.01)
*A61M 5/142* (2006.01)
(Continued)

(52) U.S. Cl.
CPC .......... *A61M 5/19* (2013.01); *A61M 5/14244* (2013.01); *A61M 5/14248* (2013.01);
(Continued)

(58) Field of Classification Search
CPC .......... A61M 5/19; A61M 5/24; A61M 5/347; A61M 5/14248; A61M 5/20;
(Continued)

(56) References Cited

U.S. PATENT DOCUMENTS

| 533,575 A | 2/1895 | Wilkens |
| 4,318,399 A | 3/1982 | Berndtsson |

(Continued)

FOREIGN PATENT DOCUMENTS

| EP | 0937471 A2 | 8/1999 |
| EP | 0937476 A2 | 8/1999 |

(Continued)

OTHER PUBLICATIONS

International Search Report and Written Opinion for Application No. PCT/EP2010/068358, dated Feb. 16, 2011, 14 pages.
(Continued)

*Primary Examiner* — Amber R Stiles
(74) *Attorney, Agent, or Firm* — McCarter & English, LLP

(57) ABSTRACT

A computerized electro-mechanical drug delivery device configured to deliver at least one dose of two or more medicaments. The device comprises a control unit. An electro-mechanical drive unit is operably coupled to the control unit and a primary reservoir for a first medicament and a secondary reservoir for a fluid agent, e.g. a second
(Continued)

medicament. An operator interface is in communication with the control unit. A single dispense assembly is configured for fluid communication with the primary and the secondary reservoir. Activation of the operator panel sets a first dose from the primary reservoir and based on the first dose and a therapeutic dose profile, the control unit is configured to determine a dose or range of the fluid agent. Alternatively, the control unit determines or calculates a dose or range of a third medicament. Further, a dispense interface for use with a drug delivery device is disclosed.

17 Claims, 37 Drawing Sheets

Specification includes a Sequence Listing.

Related U.S. Application Data

No. 15/245,821, filed on Aug. 24, 2016, now Pat. No. 10,350,355, which is a continuation of application No. 13/509,603, filed as application No. PCT/EP2010/068358 on Nov. 29, 2010, now Pat. No. 9,457,142.

(60) Provisional application No. 61/265,414, filed on Dec. 1, 2009.

(51) Int. Cl.
| | |
|---|---|
| *A61M 5/172* | (2006.01) |
| *A61M 5/20* | (2006.01) |
| *A61M 5/24* | (2006.01) |
| *A61M 5/315* | (2006.01) |
| *A61M 5/32* | (2006.01) |
| *A61M 5/34* | (2006.01) |
| *A61M 5/31* | (2006.01) |

(52) U.S. Cl.
CPC ............ *A61M 5/1723* (2013.01); *A61M 5/20* (2013.01); *A61M 5/24* (2013.01); *A61M 5/31511* (2013.01); *A61M 5/31525* (2013.01); *A61M 5/31546* (2013.01); *A61M 5/3202* (2013.01); *A61M 5/3294* (2013.01); *A61M 5/3295* (2013.01); *A61M 5/347* (2013.01); *A61M 5/31583* (2013.01); *A61M 2005/2407* (2013.01); *A61M 2005/2411* (2013.01); *A61M 2005/2496* (2013.01); *A61M 2005/3126* (2013.01); *A61M 2005/31518* (2013.01); *A61M 2005/31588* (2013.01); *A61M 2205/14* (2013.01); *A61M 2205/50* (2013.01); *A61M 2205/502* (2013.01); *A61M 2205/52* (2013.01); *A61M 2205/6063* (2013.01); *A61M 2205/6072* (2013.01); *A61M 2205/8206* (2013.01)

(58) Field of Classification Search
CPC ............ A61M 5/14244; A61M 5/1723; A61M 5/31525; A61M 5/31511; A61M 5/31546; A61M 5/3294; A61M 5/3295; A61M 5/3202; A61M 2205/14; A61M 2005/31588; A61M 2205/8206; A61M 2005/2407; A61M 2205/6063; A61M 2205/50; A61M 2205/6072; A61M 5/31583; A61M 2005/31518; A61M 2205/502; A61M 2005/2496; A61M 2005/2411; A61M 2005/3126; A61M 2205/52
See application file for complete search history.

(56) References Cited

U.S. PATENT DOCUMENTS

| | | |
|---|---|---|
| 4,450,415 A | 5/1984 | Gontowski, Jr. |
| 4,741,732 A | 5/1988 | Crankshaw et al. |
| 5,176,502 A | 1/1993 | Sanderson et al. |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,545,140 A | 8/1996 | Conero et al. |
| 5,582,598 A | 12/1996 | Chanoch |
| 5,626,566 A | 5/1997 | Petersen et al. |
| 5,674,204 A | 10/1997 | Chanoch |
| 5,681,285 A | 10/1997 | Ford et al. |
| 5,688,251 A | 11/1997 | Chanoch |
| 5,814,015 A | 9/1998 | Gargano et al. |
| 5,848,988 A | 12/1998 | Davis |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 9,457,142 B2 | 10/2016 | Day |
| 10,350,355 B2 | 7/2019 | Day et al. |
| 2001/0056258 A1 | 12/2001 | Evans |
| 2002/0052578 A1 | 5/2002 | Moller |
| 2002/0120235 A1 | 8/2002 | Enggaard |
| 2003/0009133 A1* | 1/2003 | Ramey ............... A61M 5/1456 |
| | | 604/155 |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0031322 A1* | 2/2005 | Boyle ............... A61M 16/0057 |
| | | 388/800 |
| 2005/0113765 A1 | 5/2005 | Veasey et al. |
| 2005/0277911 A1 | 12/2005 | Stewart et al. |
| 2006/0153693 A1 | 7/2006 | Fiechter et al. |
| 2007/0073267 A1 | 3/2007 | Muller |
| 2007/0088271 A1 | 4/2007 | Richards |
| 2007/0191770 A1 | 8/2007 | Moberg et al. |
| 2007/0197968 A1 | 8/2007 | Pongpairochana et al. |
| 2007/0233051 A1 | 10/2007 | Hohl et al. |
| 2008/0262469 A1 | 10/2008 | Brister |
| 2008/0294109 A1 | 11/2008 | Estes et al. |
| 2009/0099507 A1 | 4/2009 | Koops |
| 2009/0275916 A1 | 11/2009 | Harms et al. |
| 2009/0299328 A1* | 12/2009 | Mudd .................... A61M 5/19 |
| | | 604/506 |

FOREIGN PATENT DOCUMENTS

| | | |
|---|---|---|
| EP | 1839690 A1 | 10/2007 |
| EP | 2058020 A2 | 5/2009 |
| JP | 2006-514990 A | 5/2006 |
| JP | 2009-532117 A | 9/2009 |
| WO | 1999/38554 A1 | 8/1999 |
| WO | 2001/10484 A1 | 2/2001 |
| WO | 2002/058767 A1 | 8/2002 |
| WO | 2004/060387 A1 | 7/2004 |
| WO | 2007/049961 A2 | 5/2007 |
| WO | 2007/115039 A2 | 10/2007 |
| WO | 2008/016621 A1 | 2/2008 |
| WO | 2009/004627 A2 | 1/2009 |

(56) References Cited

OTHER PUBLICATIONS

International Preliminary Report on Patentability for Application No. PCT/EP2010/068358, dated Jun. 14, 2012, 9 pages.
U.S. Appl. No. 15/245,821, filed Aug. 24, 2016, U.S. Pat. No. 10,350,355, Issued.
U.S. Appl. No. 16/512,127, filed Jul. 15, 2019, U.S. Pub. No. 2020-0023129, Published.
U.S. Appl. No. 16/598,555, filed Oct. 10, 2019, U.S. Pub. No. 2020-0030531, Published.
U.S. Appl. No. 16/598, 839, filed Oct. 10, 2019, U.S. Pub. No. 2020-0030532, Published.

\* cited by examiner

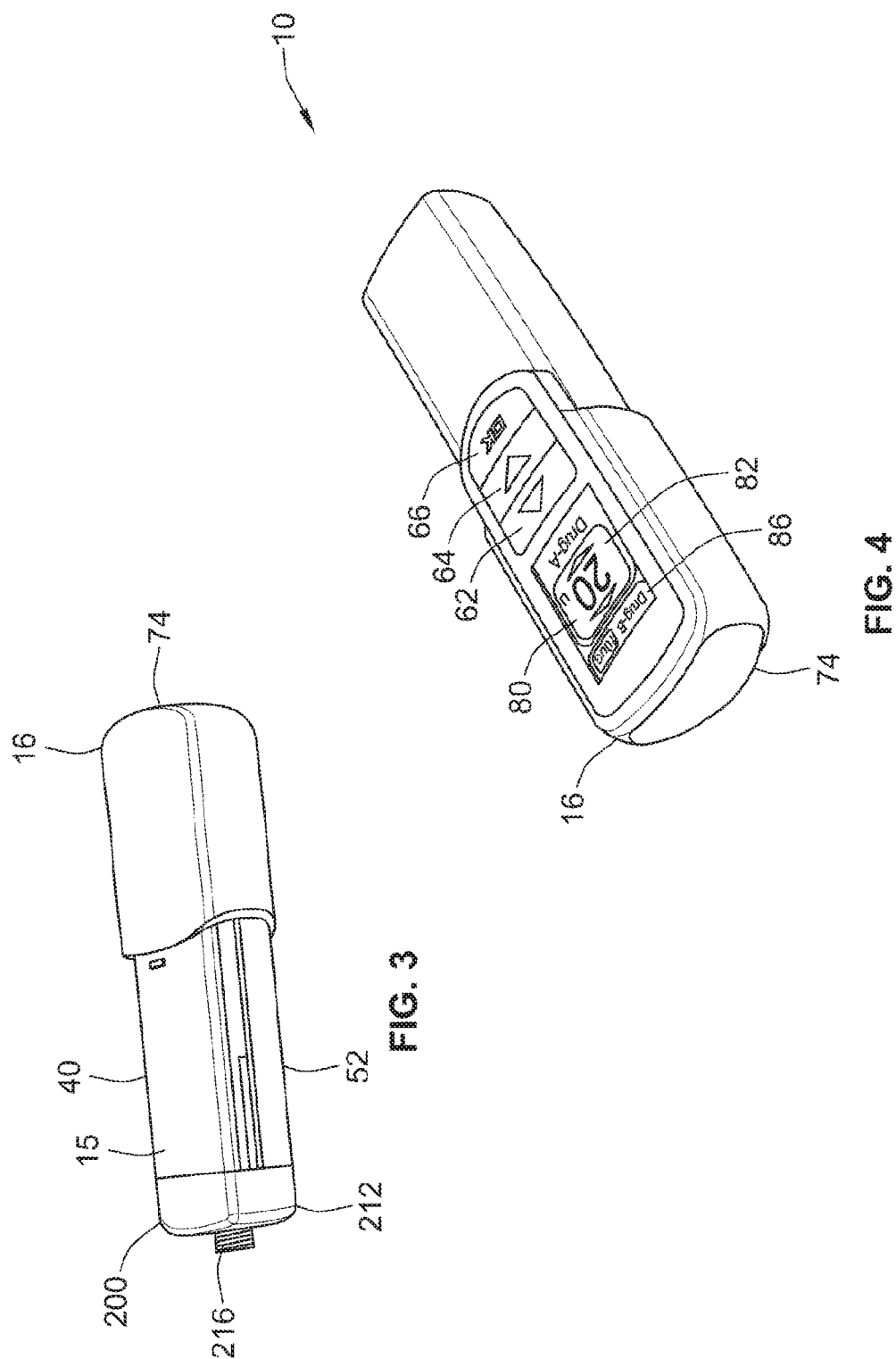

DRUG DELIVERY DEVICE INCLUDING MOTION DETECTION SYSTEM

CROSS REFERENCE TO RELATED APPLICATIONS

The present application is a continuation of U.S. patent application Ser. No. 16/512,127 filed Jul. 15, 2019, which is a continuation U.S. patent application Ser. No. 15/245,821 filed Aug. 24, 2016, now U.S. Pat. No. 10,350,355, which is a continuation of U.S. patent application Ser. No. 13/509,603 filed Sep. 12, 2012, now U.S. Pat. No. 9,457,142, which is a U.S. National Phase Application pursuant to 35 U.S.C. § 371 of International Application No. PCT/EP20101068358 filed Nov. 29, 2010, which claims priority to U.S. Provisional Patent Application No. 61/265,414 filed Dec. 1, 2009 and to European Patent Application No. 09179724.1 filed Dec. 17, 2009. The entire contents of each of these applications are herewith incorporated by reference into the present application in their entirety.

SEQUENCE LISTING

This application contains a Sequence Listing which has been submitted electronically in ASCII format and is hereby incorporated by reference. The ASCII text file, created Oct. 10, 2019, is named 128868-02206_ST25.txt and is 2 kilobytes in size.

FIELD OF THE PRESENT PATENT APPLICATION

The present patent application relates to medical devices and methods of delivering at least two drug agents from separate reservoirs using a device having a programmable dose setting mechanism and a single dispense interface. Such drug agents may comprise a first and a second medicament. A single dose setting procedure initiated by the user causes the drug delivery device to compute a dose of a second drug agent based on a selected therapeutic dose algorithm. This single dose setting procedure initiated by the user may also cause the drug delivery device to compute a dose of a third drug agent based on a (potentially) different selected therapeutic dose algorithm. Such algorithms may either be previously selected prior to dose setting or at the time that the dose is set.

The drug agents may be contained in two or more multiple dose reservoirs, containers or packages, each containing independent (single drug compound) or pre-mixed (co-formulated multiple drug compounds) drug agents. The electro-mechanical dose setting mechanism is of particular benefit where a targeted therapeutic response can be optimized for a specific target patient group. This may be achieved by a microprocessor based drug delivery device that is programmed to control, define, and/or optimize a therapeutic dose profile. A plurality of potential dose profiles may be stored in a memory device operatively coupled to the microprocessor. For example, such stored therapeutic dose profiles may include, but are not limited to, a linear dose profile; a non-linear dose profile; a fixed ratio—fixed dose profile; a fixed dose variable dose profile; a delayed fixed dose—variable dose profile; or a multi-level, fixed dose variable dose profile as discussed and described in greater detail below. Alternatively, only one dose profile would be stored in a memory device operatively coupled to the microprocessor.

BACKGROUND

Certain disease states require treatment using one or more different medicaments.

U.S. 2007088271 describes a dispenser for medicaments comprising a first metering pump for insulin and a second metering pump for glucose or glucagon. A controller for both pumps is programmed to maintain a basal supply of insulin, and is responsive to a signal from a separate glucometer to dispense either additional insulin or glucose or glucagon as appropriate.

U.S. 2008262469 describes an integrated system for the monitoring and treating of diabetes, including an integrated receiver/hand-held medicament injection pen with electronics, for use with a continuous glucose sensor. In some embodiments, the receiver is configured to receive continuous glucose sensor data, to calculate a medicament therapy (e.g., via the integrated system electronics) and to automatically set a bolus dose of the integrated hand-held medicament injection pen, whereby the user can manually inject the bolus dose of medicament. US2008262469 further describes an integrated system for use with at least two hand-held medicament injection pens, such as both a medicament pump and a handheld medicament injection pen. Regardless of the type of medicament delivered and the delivery device used, the processor module includes programming to calculate the dose of that particular medicament in response to the continuous glucose sensor data.

WO2009004627 describes delivery of more than one therapeutic fluid as a means to control symptoms of health conditions. More than one therapeutic fluid may be dispensed from more than one reservoir and delivered to a user's body via one or more cannula that penetrate the skin. The therapeutic fluids may be delivered by action of one or more pumping mechanisms that may be controlled by a processor in a portable, ambulatory device. The therapeutic fluids may optionally be insulin and one or more of an amylin analog, pramlintide acetate and an exenatide, and the health condition may optionally be diabetes.

WO2007049961 shows a device for regulating the concentration of glucose in the blood of a diabetes patient which comprises: a measuring means for measuring said concentration, a pump means for selectively introducing glucagon, glucose, or insulin into the body of the patient, for instance by means of at least one hypodermic needle to be inserted into the body of the patient, and a control means which receives signals from the measuring means which are representative of said concentration and which control the pump means on the basis of at least one reference value for said concentration pre-entered into the control means and a program. The device is embodied such that the measuring means and the pump means can be in substantially permanent contact with the bodily fluid or the blood of a patient.

U.S. 2007073267 describes injection devices, systems and methods for injecting two or more medicaments to a patient at a single injection site while preferably minimizing any mixing of the medicaments prior to delivery to the patient. The invention can also be used to sequentially deliver the medicaments to the patient in a repetitive manner. For example, the injection apparatus can sequentially provide a first medicament and then a second medicament to the patient during a first injection procedure. During a second injection procedure, the injection apparatus can again sequentially provide the first medicament and the second medicament to the patient either at the injection site of the first injection procedure or at a different injection site.

Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament). GLP-1 is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g., injection, needle-less injection, pumps, or inhalation. However, the process for combining the two agents and then administering this combination therapy needs to be simple and convenient for the user to perform reliably, repeatedly and safely.

A further problem that may often arise is that the quantities and/or proportions of each active agent making up the combination therapy may need to be varied for each user or at different stages of their therapy. For example, one or more active agents may require a titration period to gradually introduce a patient to a "maintenance" dose. A further example would be if one active agent requires a non-adjustable fixed dose while the other active agent is varied. This other active agent may need to be varied in response to a patient's symptoms or physical condition. Because of such a potential problem, certain pre-mixed formulations comprising two or more active agents may not be suitable as these pre-mixed formulations would have a fixed ratio of the active components, which could not be varied by the healthcare professional or user.

Additional problems can arise where a multi-drug compound therapy is required, because many users cannot cope with having to use more than one drug delivery system or make the necessary accurate calculation of the required dose combination. Other problems arise where a drug delivery system requires the user to physically manipulate the drug delivery device or a component of the drug delivery device (e.g., a dose dialing button) so as to set and/or inject a dose. This may be especially true for certain users who are challenged with dexterity or computational difficulties.

Accordingly, there exists a need to provide devices and/or methods for the delivery of two or more medicaments in a single injection or delivery step that is simple for the user to perform without complicated physical manipulations of the drug delivery device. The proposed programmable electro-mechanical drug delivery device overcomes the above-mentioned problems. For example, the proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other. This may be just one programmable feature of the proposed electro-mechanical drug delivery device.

In addition, when a user sets a dose of the first or primary medicament, the proposed electro-mechanical micro-processor based drug delivery device automatically calculates the dose of the second medicament (i.e., non-user settable) based at least in part on a programmed therapeutic dose profile or programmed algorithm. In an example embodiment, the dose of the second medicament is calculated based only on the dose of the first medicament and the therapeutic dose profile or the programmed algorithm. In an alternative arrangement, the proposed electro-mechanical micro-processor based drug delivery device automatically calculates the dose of the second medicament and/or a third medicament based on a programmed therapeutic dose profile or programmed algorithm. The profile used to compute the dose of the third medicament may or may not be the same type of profile used to compute the dose of the secondary medicament.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent. The user, for example a patient, a healthcare professional or any other person using the device, would then select the most appropriate secondary package or series or combination of series of different packages for a particular treatment regime.

SUMMARY

The present application allows for a combination of multiple drug compounds within a single electro-mechanical device to achieve a therapeutic dose profile. Such therapeutic dose profile may be a pre-selected profile and may be one of a plurality of dose profiles stored in a memory device contained within the drug delivery device. The electro-mechanical device may comprise two or more such medicaments. The device allows the user to set a multi-drug compound device through one single dose setting mechanism (such as a digital display, a soft-touch operable panel, and/or graphical user interface (GUI)). The device then allows the dispense of at least a plurality of medicaments through a single dispense interface (such as a double-ended needle assembly). This single dose setter can control the electro-mechanical drive unit of the device such that a predefined combination of the individual drug compounds may be administered when a single dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like forms of drug delivery.

According to a first aspect of the present invention, a device is disclosed comprising a control unit configured to receive information on a dose of a primary medicament. The control unit is further configured to determine at least one value of a dose of a fluid agent based at least in part on the dose of the primary medicament and a therapeutic dose profile. The control unit may further comprise a microcontroller and a memory configured to store the therapeutic dose profile.

In an example embodiment, the therapeutic dose profile is a non-linear profile of the primary medicament and the fluid agent.

In an example embodiment, the fluid agent is a secondary medicament.

In an example embodiment, the control unit is configured to determine the at least one value of a dose of the fluid agent based only on the dose of the primary medicament and the therapeutic dose profile.

In a further example embodiment, the device comprises an operator interface in communication with the control unit, wherein the information on the dose of the primary medicament is received by the control unit from the operator interface.

In an example embodiment, the control unit is configured to determine one value of the dose of the fluid agent. A user confirmation for the determined value may be requested on the display. The control unit may then be configured to receive the user confirmation of the determined value of the dose of the fluid agent from the operator interface.

In a further embodiment, the at least one value of the dose of the fluid agent is a range of values. Thus, the control unit is configured to determine a range of values of the dose of the fluid agent. The range of values of the dose of the fluid agent may be displayed on a display of the operator interface, for example so that a user may select a dose value within the range. The control unit may then be configured to receive the user selection of a dose value within the range of values of the dose of the fluid agent from the operator interface.

In a further example embodiment, the control unit may further be configured to determine at least one value of a dose of another fluid agent, for example a third medicament, based at least in part on the dose of the primary medicament and the therapeutic dose profile.

The primary medicament may comprise an insulin and/or an insulin analog. The fluid agent or second medicament may comprise a GLP-1 and/or a GLP-1 analog.

In a further example embodiment, the device comprises an electro-mechanical drive unit operably coupled to the control unit. The electro-mechanical drive unit may also be coupled to a primary reservoir containing the primary medicament and a secondary reservoir containing the fluid agent. Further, the device may comprise a single dispense assembly configured for fluid communication with the primary and the secondary reservoir. Thus, the primary medicament and the fluid agent may be expelled through the single dispense interface, for example in a subsequent manner or simultaneously. In an example embodiment, activation of an input element from the operator interface, for example of an injection button, causes the electro-mechanical drive unit to dispense the dose of the primary medicament and the dose of the fluid agent through the single dispense assembly.

In an example embodiment, the electromechanical drive unit may be in another device, and the control unit may be operably coupled to the electromechanical drive unit through a communication interface, for example through a wired or wireless communication interface. A wired communication interface may comprise a serial interface, for example a universal serial bus (USB) interface. A wireless interface may comprise a Bluetooth™ or a W-LAN interface.

In a further example embodiment, the single dispense assembly comprises a first inner body comprising a first piercing needle in fluid communication with the primary reservoir and a second piercing needle in fluid communication with the secondary reservoir. The single dispense assembly may comprise a double ended needle assembly.

The primary and the secondary reservoirs may be contained in at least one multi-dose cartridge comprising a stopper and a pierceable septum. For example, a multi-dose cartridge may comprise both the primary and the secondary reservoirs. The multi-dose cartridge may further comprise at least one third reservoir. Alternatively, a single cartridge may be used for each, reservoir.

According to a second aspect of the invention, a method is disclosed comprising receiving at a control unit information on a therapeutic dose profile, and receiving at the control unit information on a dose of a primary medicament. The control unit determines at least one value of a dose of a fluid agent based at least in part on the information on the dose of the primary medicament and the therapeutic dose profile. Administration of the dose of the primary medicament and the dose of the fluid agent is initiated in accordance with the therapeutic dose profile. The information on the dose of the primary medicament may be received by the control unit from an operator interface. In an example embodiment, the fluid agent is a secondary medicament.

In an example embodiment, the control unit determines one value of the dose of the fluid agent. The method may further comprise requesting a user confirmation for the determined value on the display. A user confirmation of the determined value of the dose of the fluid agent may be received from the operator interface. Alternatively, no request for a user confirmation is displayed, and the determined value of the dose of the fluid agent is selected automatically.

In an alternative embodiment, the at least one value of the dose of the fluid agent is a range of values. Thus, the control unit determines a range of values of the dose of the fluid agent. The method may further comprise displaying the range of values of the dose of the fluid agent on a display of the operator interface, for example so that a user may select a dose value within the range. In an example embodiment, the method further comprises receiving the user selection of a dose value within the range of values of the dose of the fluid agent from the operator interface. The control unit may not receive a dose value outside the displayed range. In response to a value outside the range, a user query may be shown, asking the user to select a value within the range.

In a further example embodiment, the method comprises determining at least one value of a dose of another fluid agent, for example of a third medicament, based at least in part on the dose of the primary medicament and the therapeutic dose profile.

In an example embodiment, the method comprises determining the at least one value of a dose of another fluid agent based only on the dose of the primary medicament and the therapeutic dose profile.

The primary medicament may comprise an insulin and/or an insulin analog. The fluid agent or second medicament may comprise a GLP-1 and/or a GLP-1 analog.

In an example embodiment, activation of the operator interface may cause an electro-mechanical drive unit to dispense the dose of the primary medicament and the dose of the fluid agent through a single dispense interface.

The predefined therapeutic dose profile may be a linear ratio profile or a non-linear ratio profile of the primary and the secondary medicaments.

In a further aspect of the invention, a computer program, a computer program product and a computer readable medium are disclosed, comprising code that—when executed—performs the steps described above in relation to the method aspect.

By defining the therapeutic relationship between at least a plurality of drug compounds, the proposed microprocessor based drug delivery device helps to ensure that a patient/user receives the optimum therapeutic combination dose from a multi-drug compound device. This microprocessor may comprise a microcontroller. This combination dose may be set and administered without the potential inherent risks that may be associated with multiple inputs, where the user is often called upon to calculate and set the correct dose combination each time that the device is used to administer a dose. The medicaments can be fluids, defined herein as liquids, gases or powders that are capable of flowing and that change shape when acted upon by a force tending to change its shape. Alternatively, one of the medicaments may be a solid where such a solid may be carried, solubilized or otherwise dispensed with another fluid, for example a fluid medicament or a liquid.

The proposed electro-mechanical device is of particular benefit to users with dexterity or computational difficulties as the single input and associated predefined therapeutic profile removes the need for a user to calculate a prescribed dose every time they use the device. In addition, the single input allows easier dose setting and dose administration of the combined compounds. The electro-mechanical nature of the preferred drug delivery device also benefits users with dexterity and visual challenges since the proposed drug delivery device may be operated and/or controlled by way of a micro-processor based operator panel.

In a preferred embodiment a master drug compound, such as insulin, contained within a multiple dose device could be used with at least a secondary medicament contained within the same device. A third medicament contained within the same device may also be provided. For example, this third medicament could be a long or a short acting insulin.

In a preferred arrangement, a computerized electro-mechanical drug delivery device delivers at least one dose of two or more medicaments. In an alternative embodiment, the device delivers more than one dose of two or more medicaments. This dose may be a combined dose. The device comprises a main body comprising a microprocessor based control unit. An electro-mechanical drive unit is operably coupled to the control unit. The electro-mechanical drive unit is coupled to a primary reservoir and a secondary reservoir. Preferably, the electro-mechanical drive unit is coupled to the primary reservoir and the secondary reservoir by way of first and second drive trains. The first and the second drive trains may be similar in operation.

An operator interface is in communication with the control unit. A single dispense assembly (such as a dispense interface and/or a needle assembly) may be configured for fluid communication with the primary and the secondary reservoir. Activation of the operator panel sets a dose of the primary medicament from the primary reservoir. Based on at least the selected dose of the primary medicament, the control unit computes a dose of the secondary medicament based at least in part on a therapeutic dose profile. In an alternative arrangement, based on at least the selected dose of the primary medicament, the control unit computes a range of a dose of the secondary medicament based at least in part on a therapeutic dose profile. A user may then select a dose of the secondary medicament within the determined range. Based on at least the selected dose of the primary medicament, the control unit may also compute a dose or a range of a dose of the third medicament based at least in part on a therapeutic dose profile. The primary medicament may or may not be administered to an injection site simultaneously with the secondary medicament. In an example embodiment, the control unit may base its computations only on the dose of the primary medicament and the therapeutic dose profile.

In one arrangement, the selected profile may be determined when a cartridge of medicament is inserted into a cartridge retainer of the drug delivery device. A cartridge may comprise one or more reservoirs for storing and releasing one or more medicaments. Separate cartridges for each medicament may be used in a device, or a single cartridge with multiple reservoirs may be used. For example, the cartridge retainer of the device may contain a cartridge identification circuit that when or if the device 'reads' a cartridge identifier provided on the inserted cartridge, logic contained in the device could determine which of the plurality of stored profiles is the appropriate profile to select for the particular medicament contained within the cartridge. In one such arrangement, this selection process might therefore be fully automatic. That is, no user intervention is required to select the proper profile. In an alternative embodiment, cartridge identification information may be used to request a profile through a wired or wireless connection, for example a universal serial bus (USB) connection, a Bluetooth™ connection, a cellular connection and/or the like. The profile may be requested from an internet page. The profile may be received by the device through the same wired or wireless connection. The profile may then be stored and applied in the apparatus without any user intervention or after confirmation by a user.

Alternatively, this therapeutic profile selection process might be semi-automatic. For example, this therapeutic profile may be suggested and selected via a graphical user interface provided on a digital display. For example, the GUI may prompt the user to confirm which profile they want from a limited range of options or fully configurable by the user, for example by a patient or health care provider.

Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of the present application, the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), (SEQ ID NO:1) Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Lys-Lys-Lys-Lys-Lys-Lys-NH2) (SEQ ID NO:2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipres sin, Gonadorelin, Triptorelin, Leuprorelin, Buserelin, Nafarelin, Goserelin.

In one preferred arrangement, the proposed electro-mechanical drug delivery device has a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

In one preferred arrangement, the secondary reservoir contains multiple doses of medicament. The system may be designed such that a single activation of a dose button causes the user set dose of medicament to be expelled from the primary reservoir. As a result, a dose of medicament from the second reservoir is determined based on a preprogrammed therapeutic profile and this combination of medicaments will be expelled through the single dispense interface. By user settable dose it is meant that the user (e.g., patient or health care provider) can enter the dose of the primary medicament by way of the device so as to set a desired dose. Additionally, the user settable dose can be set remotely through a communications port such as a wireless communication port (e.g., Bluetooth, WiFi, satellite, etc.). Alternatively, the user settable dose can be set through a wired communications port such as a Universal Serial Bus (USB) communications port. Additionally, the dose may be set by another device, such as a blood glucose monitor after performing a therapeutic treatment algorithm.

By calculated dose, it is meant that the user (or any other input) cannot independently set or select a dose of medicament from the secondary reservoir but rather it is computed to achieve a predefined therapeutic profile of a combination of both primary and secondary medicaments. In other words, when the user (or another input as described above) sets the dose of the primary medicament in the primary reservoir, the dose of the second medicament is determined by the micro-processor control unit. This combination of medicaments is then administered via a single interface.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

Attach a dose dispenser, such as a double-ended needle assembly, to a distal end of the dispense interface. In this manner, a proximal end of the needle assembly is in fluidic communication with both the primary compound and secondary compound.

Dial up/set a desired dose of the primary compound from the injection device, for example, via a graphical user interface (GUI).

After the user sets the dose of the primary compound, the micro-processor controlled control unit determines or computes a dose of the secondary compound and preferably determines or computes this second dose based on a previously stored therapeutic dose profile. Where the drug delivery device includes a third medicament, the micro-processor controlled control unit computes a dose of the third medicament based on the same or a different therapeutic dose profile. It is this computed combination of medicaments that will then be injected by the user. The therapeutic dose profile may be user selectable.

Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

The proposed drug delivery system may be designed in such a way as to limit its use to exclusive primary and secondary reservoirs through employment of dedicated or coded cartridge features. In some situations, it may be beneficial from a therapeutic and safety point of view to ensure that the primary reservoir can be a standard drug containing vial or cartridge. This would allow the user to deliver a combined therapy when a secondary reservoir is included in the device. It would also allow delivery of the primary compound independently through a standard dose dispenser in situations where the combined therapy is not required. This could include situations, such as, but not limited to, dose splitting (i.e., delivering the complete dose of the primary therapy in two separate injections) or top-up of the primary compound in a way that would prevent the potential risk of double dosing of the secondary compound that such scenarios might otherwise present.

A particular benefit of the proposed drug delivery device is that the use of two or more multi-dose reservoirs makes it possible to tailor dose regimes when required, for example where a titration period is necessary for a particular drug. The secondary reservoir, third reservoir, and/or other reservoirs may be supplied in a number of titration levels with certain differentiation features such as, but not limited to, aesthetic design of features or graphics, numbering or the like symbols, so that a user could be instructed to use the supplied secondary reservoirs in a specific order to facilitate titration. Alternatively, a prescribing physician or health care provider may provide the patient with a number of "level one" titration secondary reservoirs and then when these were finished, the physician could then prescribe the next level. Alternatively, a single strength formulation could be provided and the device could be designed to deliver a predefined fraction of the full intended dose during the titration period. Such a fraction could be gradually increasing, stepped or any therapeutically beneficial or desirable variant thereof. One advantage of such a titration program is that the primary device remains constant throughout the administration process.

In a preferred arrangement, the drug delivery device is used more than once and therefore is multi-use. Such a device may or may not have a replaceable reservoir of the primary drug compound, but the presently disclosed arrangements are equally applicable to both scenarios. It is possible to have a suite of different secondary reservoirs for various conditions that could be prescribed as one-off extra medication to patients already using a standard drug delivery device.

A further feature of a preferred arrangement is that both medicaments are delivered via one injection needle or dose dispenser and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

In a further aspect, an apparatus is described comprising a control unit configured to receive information on a dose of a primary medicament. The control unit is further configured to determine a dose of a fluid agent based at least in part on said dose of said primary medicament and a therapeutic dose profile. The fluid agent may be a medicament, for example a liquid medicament or a liquid solution of a medicament.

In a further aspect, a method is disclosed comprising receiving at a control unit information on a therapeutic dose profile. The method further comprises receiving at the control unit information on a dose of a primary medicament, determining at the control unit a dose of a fluid agent based at least in part on said information on said dose of said primary medicament and the therapeutic dose profile, and initiating administration of said dose of said primary medicament and said dose of said fluid agent in accordance with the therapeutic dose profile.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 3 illustrates a perspective view of a cartridge holder and a back side of the delivery device illustrated in FIG. 1b;

FIG. 4 illustrates a perspective view of a proximal end of the delivery device illustrated in FIG. 1b;

DETAILED DESCRIPTION

Figure 1A:
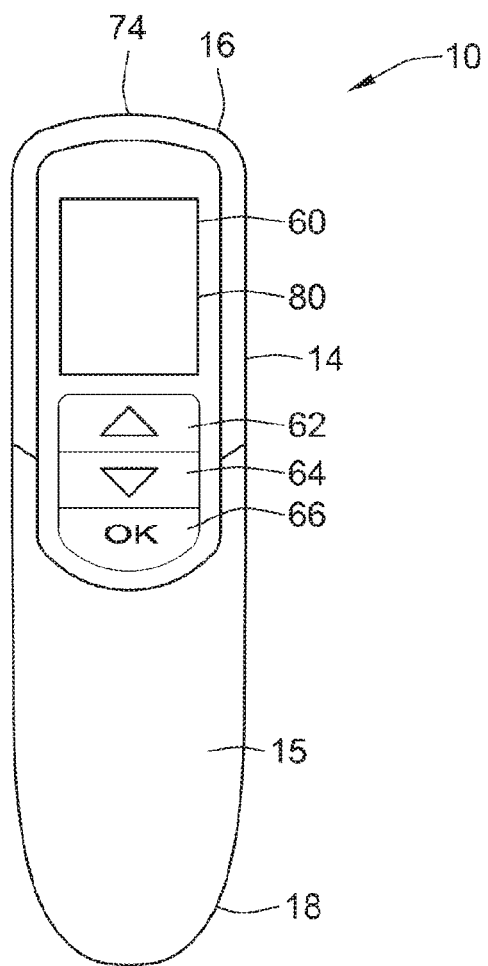
FIG. 1a illustrates a plan view of a programmable drug delivery device in accordance with one aspect of the present invention and FIG. 1b illustrates a plan view of a programmable drug delivery device with an end cap removed in accordance with one aspect of the present invention.
Figure 1B:
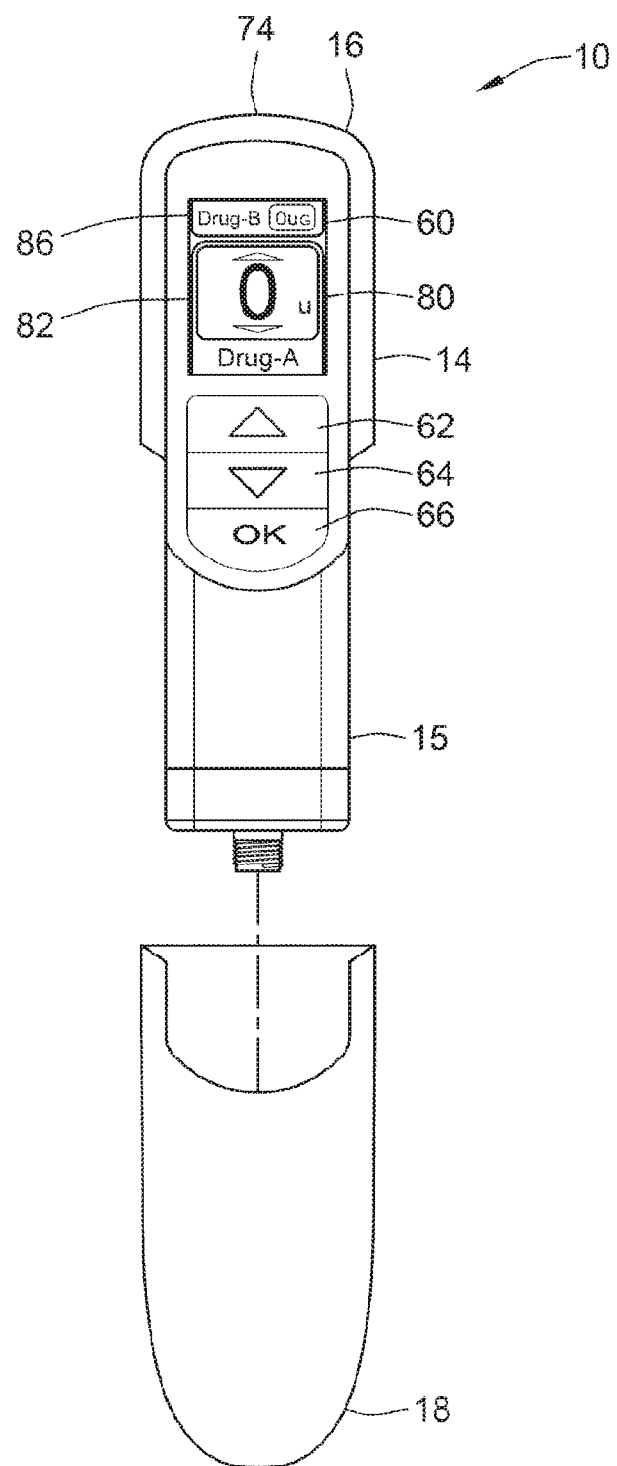
Figure 2:
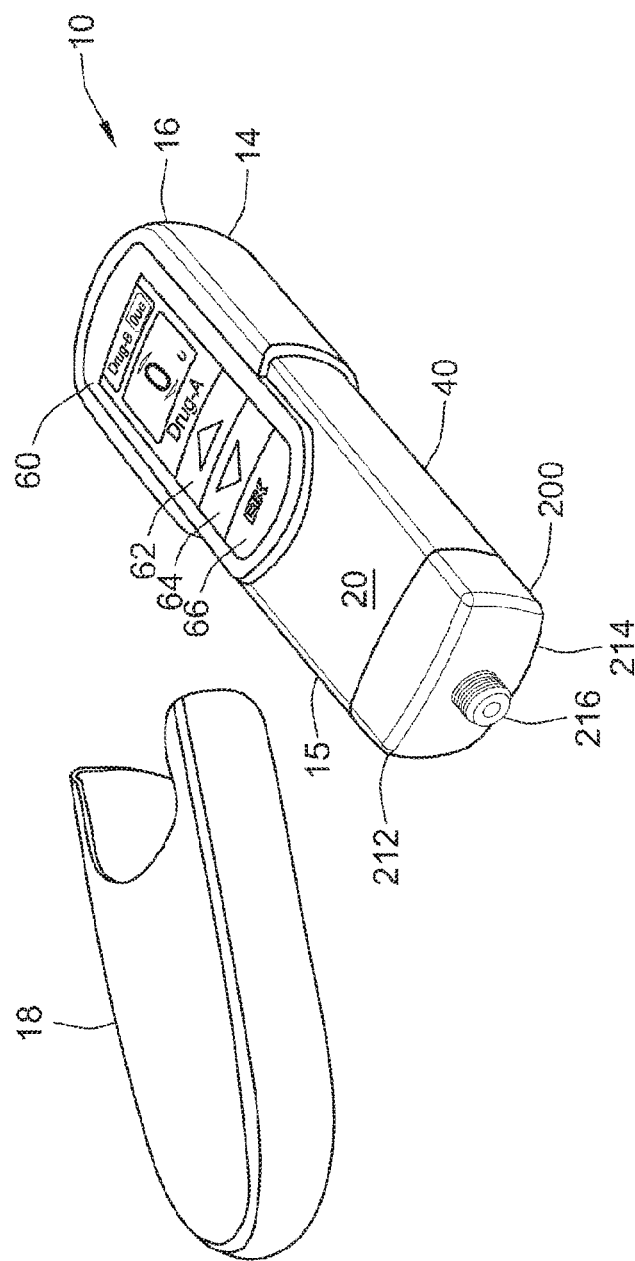
FIG. 2 illustrates a perspective view of the delivery device illustrated in FIGS. 1a and 1b with an end cap of the device removed.

FIGS. 1a and 1b illustrate plan views of a programmable drug delivery device 10 in accordance with one aspect of the present invention. FIG. 1a illustrates the device 10 when an end cap 18 is on the device 10. In FIG. 1b, the device 10 is illustrated in a ready mode in that the end cap 18 is off and the device 10 has been turned on so that the digital display 80 is illuminated. When the device is activated with the cap on only cartridge contents, battery status and last dose information will be available for display. When the cover is removed the dose setting screen will be available. FIG. 2 illustrates a perspective view of the delivery device 10 illustrated in FIGS. 1a and 1b with the end cap 18 of the device 10 removed. In FIG. 2, the device is turned on so that the digital display is illuminated. FIG. 3 illustrates a perspective view of a cartridge holder and the back side of the delivery device illustrated in FIGS. 1a and 1b. FIG. 4 illustrates a perspective view of a proximal end of the delivery device 10.

Referring now to FIGS. 1 through 4, there can be seen a micro-processor controlled electro-mechanical drug delivery device 10 in accordance with the present invention. Preferably, this drug delivery device 10 is generally rectangular in shape comprising generally rounded ends so as to easily fit in a user's shirt pocket and is also compact enough to fit in a hand bag.

As will be described in greater detail below, the drug delivery device 10 contains a micro-processor control unit that operates an electro-mechanical drive that is used to deliver at least two drugs (a first or primary medicament and a second or secondary medicament) during a single dosing operation. This enables the drug delivery device 10 to provide, for example, a primary medicament such as a long acting insulin along with a secondary medicament such as a GLP1 as a combination therapy. Such combination therapy may be defined by one of a plurality of therapeutic profiles stored in a memory device that is coupled to the micro-processor contained within the device 10.

The drug delivery device illustrated in FIGS. 1 through 4 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body. Other types of connection mechanisms may also be used such as frictional fits or snap fits provided by way of a clip feature.

As will be described in greater detail below, the main body 14 contains a micro-processor control unit, an electromechanical drive train, and at least two medicament reservoirs. When the end cap or cover 18 is removed from the device 10 (as illustrated in FIGS. 1b, 2, 3, and 4), a dispense interface 200 (see FIG. 3) is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." As illustrated, the first dose setting button 62 resides above the second dose button 64 which is positioned above the OK button 66. Alternative button arrangements may also be used. As just one example, the first buttons 62 and a second button 64 may, as a pair, be rotated through 90 degrees and sit underneath the screen, with each button being adjacent to a screen area. In such an arrangement, the first and second buttons could be used as soft keys to interact with icons on the user digital display 80. In addition, along the most proximal end of the main body, an injection button 74 is also provided (see e.g., FIG. 4).

Utilizing micro-processor controlled human interface elements such as an operator panel (e.g., hard keys, buttons or soft keys with the key legend appearing on the display screen), setting the dose of the primary medicament allows the control unit to compute or determine the fixed dose of the second medicament. In one preferred arrangement, a computerized electronic control unit computes the dose of the second medicament. Most preferably, the computerized electronic control unit computes the dose of the second medicament based at least in part on a therapeutic dose profile that is stored in a memory device coupled to the micro-processor. Such a therapeutic profile may or may not be user or caregiver selectable. Alternatively, this profile may not be user selectable. As will be explained in greater detail below, a plurality of different such dose profiles may be stored on a memory storage device in the drug delivery device. In one arrangement, the preferred memory storage device comprises Flash memory of the micro-processor. An optional storage device could comprise an EEPROM that is coupled via a serial communication bus to the micro-processor of the control unit.

Figure 6:
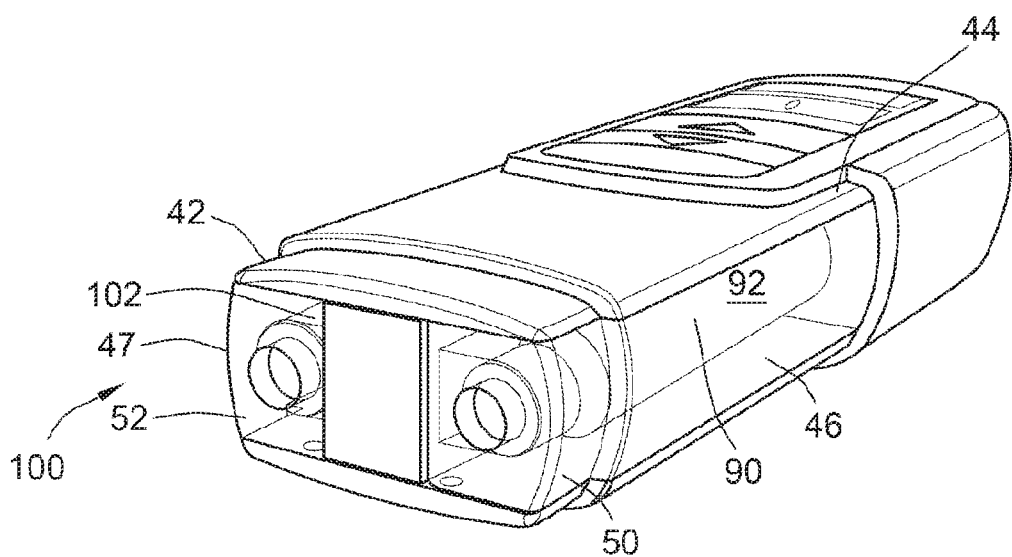
FIG. 6 illustrates a perspective view of the delivery device distal end showing the cartridge.

FIG. 2 illustrates a perspective view of the drug delivery device 10 of FIGS. 1a and 1b with the cover 18 removed so as to illustrate the main body 14 and a cartridge holder 40. By removing the cover 18 from the device, a user is provided access to the cartridge holder 40 and also the dispense interface 200. In one preferred arrangement, this cartridge holder 40 can be removably attached to the main body 14. In this arrangement, and as illustrated in FIG. 6, the cartridge holder 40 may contain at least two cartridge retainers 50 and 52. Each retainer is configured so as to contain one medicament reservoir, such as a glass cartridge. Preferably, each cartridge contains a different medicament. However, in alternative drug delivery device arrangements, more than two cartridge retainers may be contained within the cartridge housing.

Figure 10:
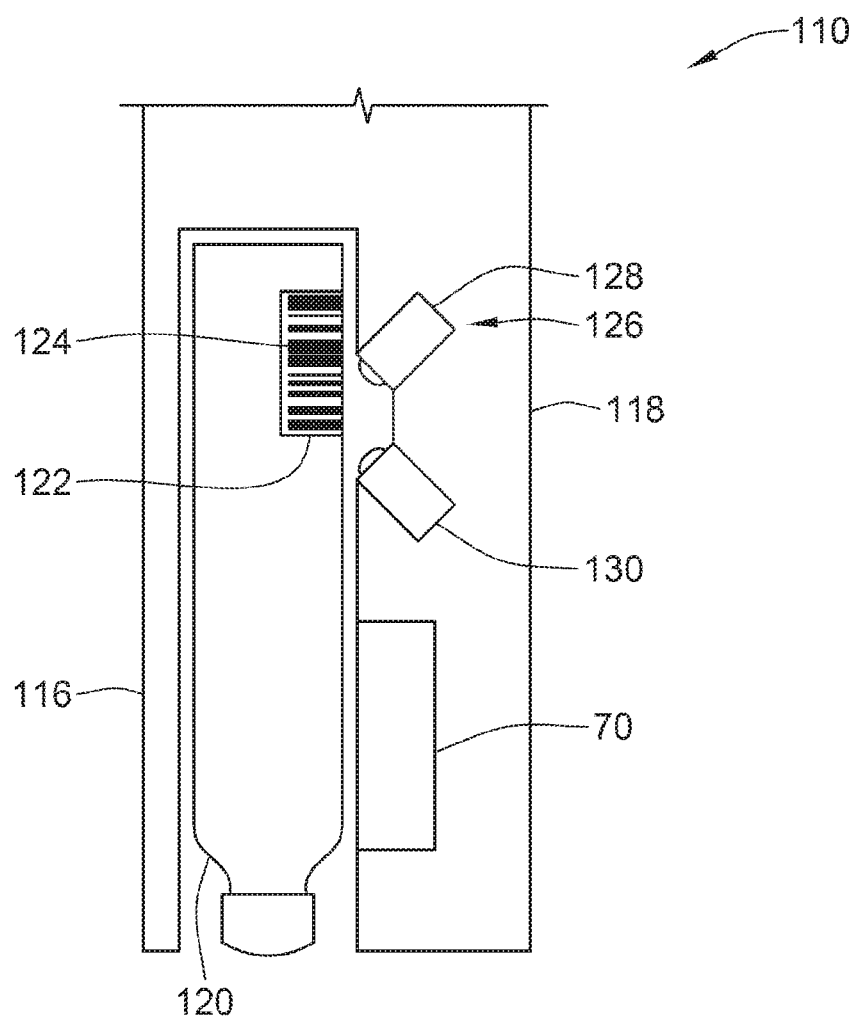
FIG. 10 illustrates one type of cartridge dedication system that may be used with the cartridge holder.

In one preferred arrangement, each cartridge retainer 50, 52 may be provided with a cartridge detecting system, such as the cartridge detecting system illustrated and described with respect to FIG. 10. Such a cartridge detecting system may comprise a mechanical or electrical switch that can be used to determine if a cartridge has been correctly inserted into the retainers 50 and 52. Ideally, such a detection system can determine if the correct size cartridge has been properly inserted into the retainer.

In addition, at the distal end of the cartridge holder 40, the drug delivery device illustrated in FIG. 2 includes a dispense interface 200. As will be described in relation to FIG. 11, this dispense interface 200 includes a main outer body 212 that is removably attached to a distal end 42 of the cartridge housing 40. As can be seen in FIGS. 2 and 3, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

At a first end or a proximal end 16 of the main housing 14, there is provided a control panel region 60. This control panel region 60 comprises a digital display, preferably an Organic Light Emitting Diode (OLEO) display 80 along with a plurality of user interface keys such as push buttons. Alternatively, this region could comprise a touch screen and icons on the display. A further option would be a display screen with a joystick, a control wheel and/or possibly push buttons. In addition, the control panel region may also comprise a swipe section so as to either increase or decrease the dose size or provide other means by which a user could operate the device 10. Preferably, the human interface controls may be configured to provide tactile, audible and/or visual feedback.

The digital display 80 may be part of a user interface that allows the user to interact with the device 10. As explained in greater detail below, this display provides a visual indication of device operation such as dose setting, dose administration, injection history, device errors, etc. The digital display 80 can also display various drug delivery device parameters. For example, the display can be programmed to display an identified medicament contained in either medicament containers and also provide a visual confirmation that the correct cartridge and therefore medicament is being used. In addition, the display can also provide dose history information such as the time since the last dose has been administered, battery level, dose size set, device status, dose dispense status, dose history information, warnings, and errors.

In addition, the display 80 may also provide the time and date and be used to set a current time and date. The display may also be used to provide the user with training information as to how the device should be used and operated. Alternatively, the display may be used to educate the user on diabetes or other therapy information via instructional videos. The display may also be used to communicate with, or receive feedback from a health care professional via the wireless or wired communication link such as USB to a PC and then potentially via the internet, or via a mobile phone coupled to the device using a wired or wireless link such as a Bluetooth™ link, a WLAN link, and/or the like. The display may also be used to configure a device communication link: that is, used for device set up and to enter passwords for a data link, such as a Bluetooth data link. In addition, the display may be used to provide drug delivery device priming information or possibly an indication of the orientation and/or relative position of the device. For example, a micro-electro-mechanical accelerometer could be provided within the device so that the device will have the intelligence to know if the user is using the device to perform a safety or priming shot (i.e., having the distal end of the device pointing upwards) or using the device to perform a dose administration step (i.e., having the distal end of the device pointing downwards).

The display may also potentially be used as a diary or life style calendar and perhaps communicate with a patient's BGM and perhaps store and display blood glucose data. The display could also indicate a dwell period, possibly proportional to a dose size, following the delivery of a dose. The display could indicate if the device is armed i.e., ready to deliver a dose and also be used to provide an indication if the dose is outside of expected limits.

In addition, by manipulating certain other buttons, the display can be used to display information stored in the control unit. For example, such stored information could include user or patient information. Such user or patient information could include their name, their address, their health number, contact details, their prescribed medication or dosage regime.

In addition, there is also the opportunity to include calendar information, which could include blood glucose readings, the size of last dose taken, exercise taken, state of health, the time these events occurred including meal times, etc. Certain key events can also be stored and viewed. For example, such key events could include device failures that could potentially result in an over or under dose, cartridge changes, priming shots, reading the dose history, removing the cap, removing the dose dispenser, removing the dispense interface, time since manufacture, time since first use along with other similar types of information and data.

The digital display could also allow the user access to a time reference maintained by the device. Such a time reference could keep track of the current time and date. This clock may be set by the user via the interface or alternatively, via a data link (e.g., USB or IRDA) provided on the device. In addition, the time reference may be provided with a permanently connected battery backup so as to maintain the passage of time if and when the main battery has been removed or is flat. This time reference may be used to determine when the last dose was taken, which can then be displayed on the display. This time reference may also be used to store certain key events. Such events could include the time and date of the following: the last dose; whether any drug delivery device errors occurred; cartridge changes; any parameter changes, any changes in therapeutic profiles; dispense interface changes; and time since manufacture.

As previously mentioned, FIG. 1b illustrates one arrangement of the drug delivery device 10 after the user has turned the device on. One way in which a user may turn the device on is for the user to press the "OK" button 66 provided on the control panel region 60. Alternatively, the device 10 can be programmed to be turned on by removing the end cap 18. The OK button 66 may then be used when the device 10 has gone into a sleep mode after a certain period of inactivity. The sleep mode may be indicated by a possibly blank display screen. Preferably, when the cap 18 is placed back upon the device, it may be possible to review via the display 80 certain dose or dosing history data by pressing one of the human interface elements, such as the OK button 66.

Once the device is turned on, the digital display 80 illuminates and provides the user certain device information, preferably information relating to the medicaments contained within the cartridge holder 40. For example, as illustrated in FIGS. 1 and 5, the user is provided with certain information relating to both the primary medicament (Drug A) and the secondary medicament (Drug B). Preferably, the display comprises at least two display regions 82, 86 containing medicament information. The first display region 82 provides the user information relating to the primary medicament: the type of medicament—"Drug A" and the amount of Drug A that has been selected by the user—"0 Units." In addition, the second display region 86 provides the user with information relating to the secondary medicament: the type of medicament—"Drug B" and the amount of Drug B that has been calculated by the device based on the amount of Drug A selected by the user and on the particular therapeutic profile—"0 µGrams." As those of ordinary skill in the art will recognize, if in an alternative arrangement the drug delivery device 10 contained three medicaments and then was used to administer a combination therapy of these three medicaments, the digital display 80 would be modified so as to comprise at least three display regions containing information for at least these three medicaments.

Where the size of the second dose is determined from the size of the first it may not be necessary to indicate the size of the second dose and hence an alternative embodiment of the display graphics may be used, for example an "O.k." indication, such as a green dot, a green check mark, or the letters "O.k.".

Aside from the digital display 80, the control panel region 60 further comprises various user interface keys. For example, as illustrated in FIGS. 1a, 1b, 2 and 4, the control panel region 60 of the drug delivery device 10 further provides the following user interface keys:

a first dose setting button 62,
a second dose setting button 64, and
an OK or Enter button 66.

The first and second dose buttons 62, 64 may be manipulated so as to allow a user of the device 10 to either increase or decrease a selected dose of the primary medicament "Drug A" to be delivered. For example, to set or increase a primary medicament dose amount, a user could toggle the first dose setting button 62. The first display region 82 would provide a visual indication to the user of the amount he or she is setting.

In the event that a user wants to decrease a previously set dose, the second dose setting button 64 may be toggled or pushed so as to decrease the set dose. Once the user has selected the amount of the primary medicament, the user may then push the "OK" button 66. Pushing the OK button 66 may instruct the device 10 to compute the corresponding dose of the secondary medicament "Drug B". Alternatively, the dose of the secondary medicament may be determined when the dose of the first medicament is set or changed.

In an alternative display arrangement, the display 80 can display the calculated amount of the secondary medicament Drug B for every incremental change of Drug A. Thereafter, the OK button 66 could then be used. For example, pressing and holding this OK button 66 for a certain period of time (e.g., 2 seconds) could be used by the user to confirm the set and calculated dose and thereby arming the device 10 ready for delivery. The combined dose could then be dispensed through a single dose dispenser by pressing the injection button 74. In one preferred arrangement, the device armed condition may be available for a limited period, for example, 20 seconds or so. In an alternative arrangement, the arm feature may not be included.

Figure 5A:
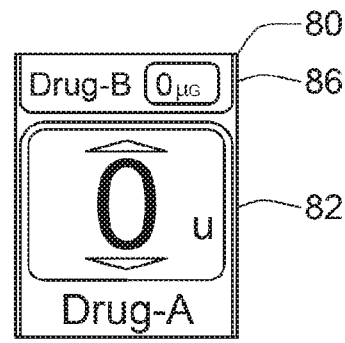
FIG. 5a illustrates a plan view of a digital display of the delivery device after the device has been turned on but before a dose is set.
Figure 5B:
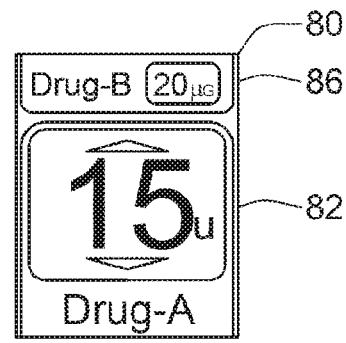
FIG. 5b illustrates a plan view of the digital display illustrated in FIG. 5a after a dose has been set.

FIG. 5a illustrates the display 80 of device 10 illustrated in FIG. 1b after the device has been turned on but before a user sets a first dose of the primary medicament Drug A. FIG. 5b illustrates this display 80 after a user has set a first dose of the primary medicament Drug A and after the device has computed the corresponding amount of the secondary medicament Drug B. As illustrated in FIG. 5b, the user has set a 15 Unit dose of the primary medicament Drug A and this is confirmed by what is displayed in the first display region 82. After the device 10 computes the secondary dose of the second medicament Drug B, this is also indicated by what is displayed in the second region 86. For example, in this situation, the device 10 calculated a dose of 20 μGrams for Drug B based in part on a 15 Unit dose of the primary medicament Drug A and based in part on one of the algorithms stored within the device.

This combined dose, 15 Units of the primary medicament Drug A and 20 μGrams of the secondary medicament Drug B, can then be injected. As may be seen from FIG. 4, at a proximal end of the main body 14 of the device 10, an injection button 74 is provided for injecting this combined dose. Alternatively, this dose inject button 74 could be provided elsewhere on the main housing 14 such as on the control panel region 60.

Other information that may be taken into account when calculating the amount of the second medicament may be the time interval since the previous dose of either the first or the second medicament. For example, the following description provides an example algorithm and process that may be used in the calculation of the size of the dose to be dispensed from the second medicament. This algorithm maybe illustrated in a flowchart 150 provided as FIG. 7.

Figure 7:
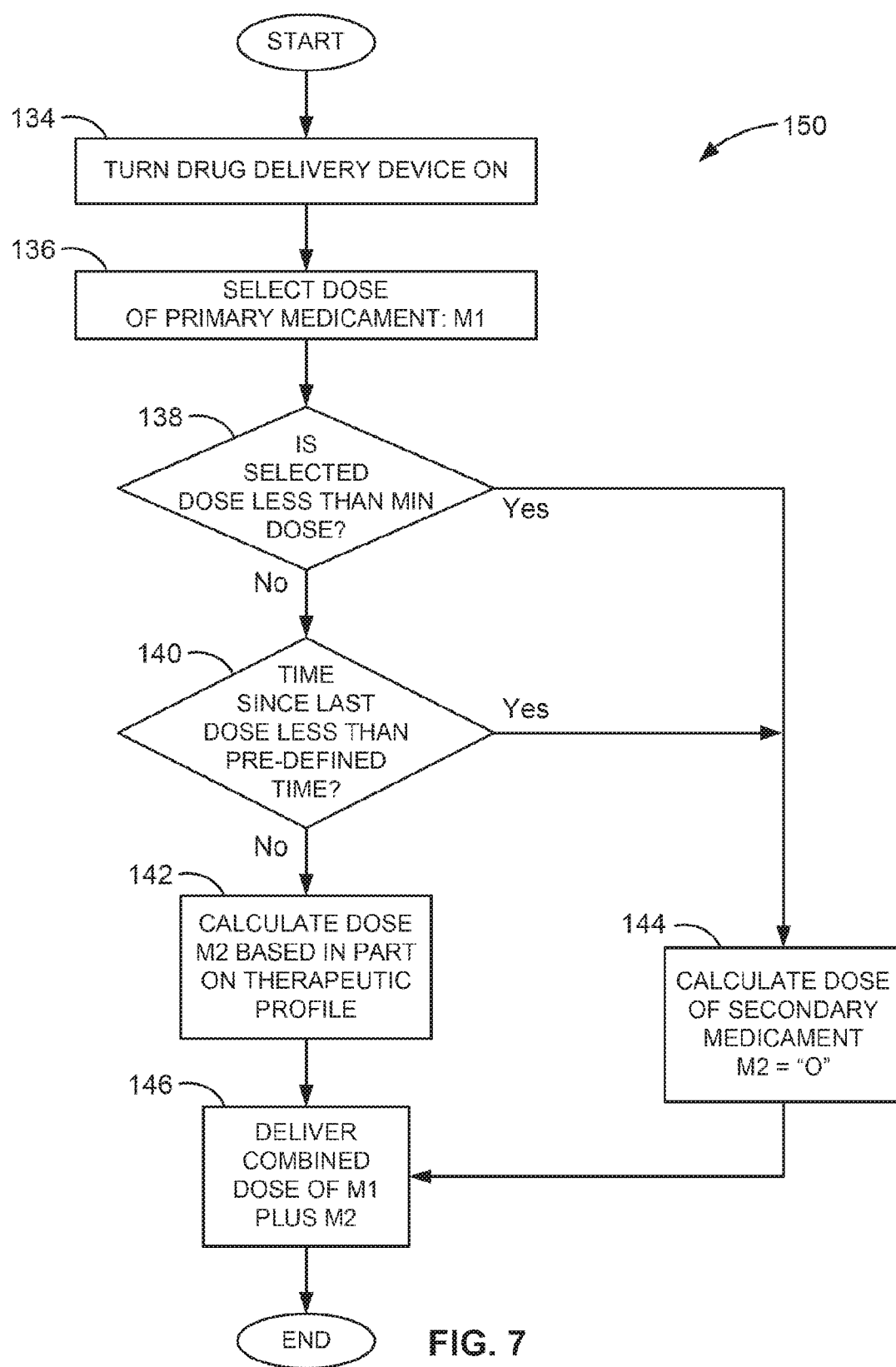
FIG. 7 illustrates a flowchart of one algorithm that can be programmed into the drug delivery device illustrated in FIGS. 1a and 1b.

As may be seen from the flowchart 150 provided in FIG. 7, first a user begins the dose selection process by turning the device on at step 134. Then, at step 136, the user selects the size of the dose to be delivered from the first medicament M1 in the first cartridge and then presses the OK button to confirm. At step 138, the microcontroller determines if the selected dose size of the first medicament M1 is less than a minimum dose threshold for the first medicament (e.g., 5 units). If it is determined that the selected dose size is indeed less than the minimum dose threshold, the process proceeds to step 144 where the calculated dose of the second medicament M2 is then computed as a zero dose. Then, the process moves to step 146 where the dose (comprising only a selected dose of the primary medicament) is administered.

If the selected dose size is determined to be greater than or equal to this minimum dose threshold, the process 150 proceeds to step 140. At step 140, the microcontroller determines if the time interval since the previous injection is less than, or equal to the predefined threshold (e.g., 18 hours). If the answer to this inquiry is yes, the process 150 proceeds to step 144 where the size of the dose from the second medicament M2 would be calculated as equal to a zero ("0") dose. Then, the process moves to step 146 where the dose (comprising only a selected dose of the primary medicament) is administered.

Alternatively, if the answer to both inquiries at steps 138 and 140 are no, then process 150 would proceed to the step 142. At step 142, the microcontroller would compute the dose of the secondary medicament M2 based at least in part on a stored therapeutic profile. If a third medicament would be provided in the drug delivery device, the microcontroller would compute a dose of a third medicament based at least in part on a stored therapeutic profile as well. This later profile may or may not be the same profile that is used to calculate the dose of the secondary medicament.

Therefore, if a user selects a dose size of the primary medicament M1 at step 136 that is equal to, or greater than, a certain minimum dose threshold for the first medicament (e.g., 5 units), and the time interval since the previous injections is greater than the predefined threshold (e.g., 18 hours) then the predefined dose of the secondary medicament from the second cartridge (e.g., 0.5 units) will be delivered when the injection is administered at step 146.

Figure 8:
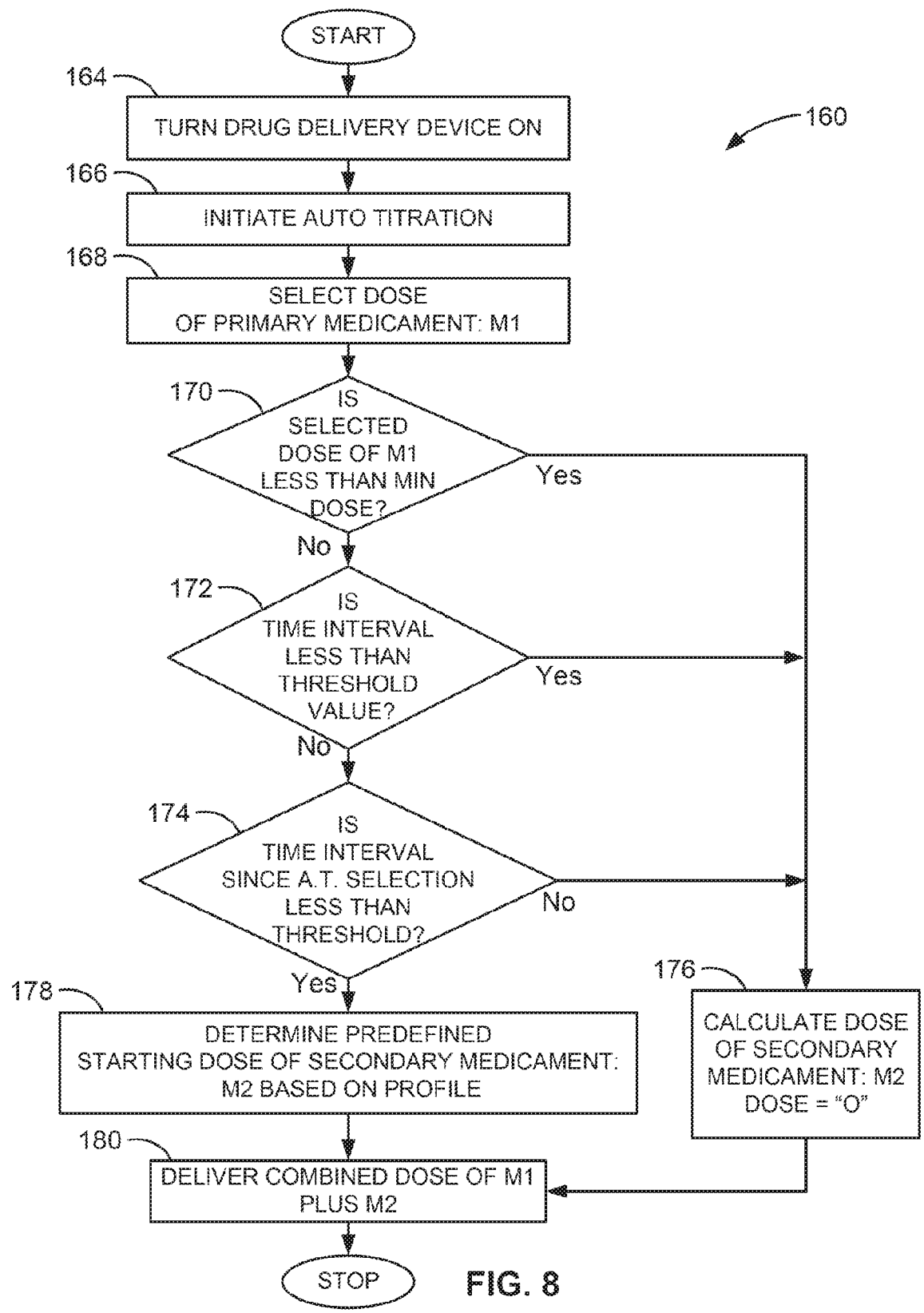
FIG. 8 illustrates a flowchart of another algorithm that can be programmed into the drug delivery device illustrated in FIGS. 1a and 1b.

The drug delivery device 10 may also be programmed with an auto titration algorithm. As just one example, such an algorithm may be used where the dose of the second medicament needs to be increased over a period of time to allow a patient to get used to the second medicament, such as is the case for GLP1 or GLP1 analogs. An exemplary auto titration algorithm is presented in a flowchart 160 illustrated in FIG. 8.

In one arrangement, after the device is turned on at step 164, a user initiates an auto titration mode of operation by manipulating one of the keys provided on the control panel. This is represented at step 166. Alternatively, this auto titration mode of operation could be automatically activated. For example, the auto titration mode of operation could be automatically activated when the drug delivery device 10 is first used, for example, when a battery is first connected to the device, when the battery is first charged, or when a profile is loaded into the device and selected by a user. After step 166, a prompt on the digital display 80 may ask a user for a password and then to confirm that the auto titration algorithm is indeed desired by the patient. In an alternative embodiment, a prompt on the digital display 80 may ask the user for a confirmation only.

Aside from using a stored algorithm for operating the device in an auto titration mode, this auto titration mode might be achieved via providing a user with cartridges containing the same medicament but with different strengths or concentrations. One disadvantage of such a scenario is that the provider of such cartridges would have to produce cartridges in at least two different strength concentrations of drugs rather than through smaller doses from a standard strength cartridge. If different strength cartridges are used, then the device may be programmed not to provide the auto-titration functionality. If this functionality is optional and patient determined, then such a function could be accessed through the digital display 80 via a 'menu' button (or other similar user interface element).

At step 168, a user selects a dose of the primary medicament M1. Then, at step 170, the microcontroller determines if the selected dose size is less than a minimum dose threshold for the first medicament (e.g., 5 units). If the microcontroller determines that the selected dose size is less than a minimum dose threshold for the first medicament, the process 160 proceeds to step 176. At step 176, the microcontroller determines that the calculated dose of the secondary medicament M2 should be a zero ("0") dose.

If at step 170 the microcontroller determines that the selected dose size of M1 is not less than a minimum dose threshold for the first medicament, the process 160 proceeds to step 172. At step 172, the microcontroller computes a time interval since the previous dose administration and determines if this computed time interval is less than, or equal to a predefined threshold (e.g., 18 hours). If at step 172 the microcontroller determines that this computed time interval is less than, or equal to a predefined threshold, the process 160 proceeds on to step 176. At step 176, the microcontroller determines that the calculated dose of the secondary medicament M2 should be a zero ("0") dose.

Alternatively, if at step 172, the microcontroller determines that this computed time interval since the previous injection is not less than, or equal to a predefined threshold, the process proceeds to step 174.

If the microcontroller determines that the selected dose size is equal to, or greater than, the minimum dose threshold for the first medicament (e.g., 5 units) at step 170 and determines that the time interval since the previous injection is greater than the predefined threshold (e.g., 18 hours) at step 172, the process proceeds to step 174. At step 174, the microcontroller determines whether the time interval since the auto-titration feature was activated is less than a predefined threshold (e.g., 1 week). If at step 174 the microcontroller determines that the time interval since the auto-titration feature was activated is greater than this predefined threshold, the process 160 moves to step 176 where a zero "0" dose of M2 is determined.

Alternatively, if the microcontroller determines that the time interval since the auto-titration feature was activated is less than the predefined threshold at step 174, the process moves to step 178. At step 178, the microcontroller determines a predefined starting dose of the secondary medicament based in part on a therapeutic profile. Then, at step 180, the predefined starting dose from the second cartridge (e.g., 0.25 micro Grams) M2 along with the previously selected dose of the primary medicament M1 from step 168 will be delivered during an injection step.

Therefore, in accordance with the auto titration flowchart 160, if the selected dose size is equal to, or greater than, the minimum dose threshold for the first medicament (e.g., 5 units) and the time interval since the previous injections is greater than the predefined threshold (e.g., 18 hours) and the time interval since the auto-titration feature was activated is greater than a predefined threshold (e.g., 1 week) then the predefined maintenance dose from the second cartridge (e.g., 0.5 units) will be delivered when the injection is taken at step 180. If the calculated responses to the steps 170 and 172 are yes or if the response to step 174 is no, then the dose that is administered would comprise only the selected dose of the primary medicament from step 168.

Aside from the user interface keys, the drug delivery device may also comprise a sounder or a sound control. For example, the device may have a sounder that generates a range of tones. Such tones could be provided so as to indicate when a button is pressed, when certain key events occur (e.g., after a dose is set, after the completion of a dose delivery, etc.), warnings that the device is not working correctly or if an incorrect cartridge has been inserted, if the device experiences certain operational errors, or if an alarm condition is triggered. The volume of the sounder may be set or configured by using a menu system controlled by the human interface elements or alternatively through a dedicated volume control button.

The main housing portion is preferably coupled to a proximal end of the cartridge holder 40. Preferably, this cartridge holder 40 comprises at least two separate cartridge retainers that are configured to hold two reservoirs of medicament. Depending on the reservoirs, these two retainers may or may not be similarly sized. For example, FIG. 3 illustrates a back side of the drug delivery device 10 illustrated in FIGS. 1*a* and 1*b* and illustrates one of the cartridge retainers 52. FIG. 6 illustrates a distal end of the cartridge holder of the drug delivery device illustrated in FIGS. 1*a* and 1*b* and illustrates both the first and the second cartridge retainers 50, 52. In one preferred arrangement, the first cartridge retainer 50 is configured for receiving a first cartridge 90 containing a primary medicament 92 and the second cartridge retainer 52 is configured for receiving a second cartridge 100 containing a secondary medicament 102. The first and second cartridges 90, 100 may or may not be of similar size and/or dimensions.

As illustrated in FIG. 6, the cartridge housing 40 comprises a first window 46 residing along a first side portion of the cartridge housing. Similarly, the cartridge housing 40 comprises a second window 47 residing along a second side portion of the cartridge housing 40. This cartridge housing 40 comprises two cartridge retainers 50, 52 and these retainers are positioned essentially side-by-side one another. Once the cap 18 is removed from the drug delivery device 10, the windows 46, 47 enable a user to view the medicaments contained within the cartridges and monitor the amount of medicament remaining in each reservoir. For example, as may be seen from FIG. 6, the first window 46 allows the user to monitor the primary medicament 92 contained within the first cartridge 90 while the second window 47 allows the user to monitor the second medicament 102 contained within the second cartridge 100. The visible cartridge contents could be confirmed by what is displayed on the digital display 80.

In this illustrated arrangement, the first cartridge 90 contains a primary medicament 92 and the second cartridge 100 may contain a secondary medicament 102. Preferably, both the first and the second cartridges contain multiple doses of each medicament 92, 102, respectively. Each cartridge is self-contained and provided as a sealed and sterile cartridge. These cartridges can be of different volumes and replaceable when empty or they can be fixed (non-removable) in the cartridge holder 40. They can also have a pierceable seal or septa at a distal end of the cartridge and configured to accept needle cannula.

Various cartridge holder arrangements may be used with the drug delivery device illustrated in FIGS. 1-6. As just one example, the cartridge holder 40 may comprise separately shaped cartridge retainers 50, 52. As just one example, the first cartridge retainer 50 may be shaped to receive a cartridge having a first volume while the second cartridge retainer 52 may be shaped to receive a cartridge having a second volume. As just one example, in one preferred arrangement, the primary medicament 92 contained in the first cartridge 90 may comprise a long acting insulin whereas the second medicament 102 contained within the secondary cartridge 100 may comprise a GLP1 or like analog.

As such, in one preferred arrangement, the volume of the first cartridge 90 may be a standard 300 Unit cartridge and therefore the first cartridge retainer 50 must be geometrically configured for such a volume. In contrast, the volume of the second cartridge 100 may be a smaller volume (e.g., in the order of 20 Units) and therefore must be geometrically configured to receive such a smaller volume cartridge. As those of ordinary skill in the art with recognize, other cartridge and cartridge retainer arrangements and geometries are possible as well.

Figure 9:
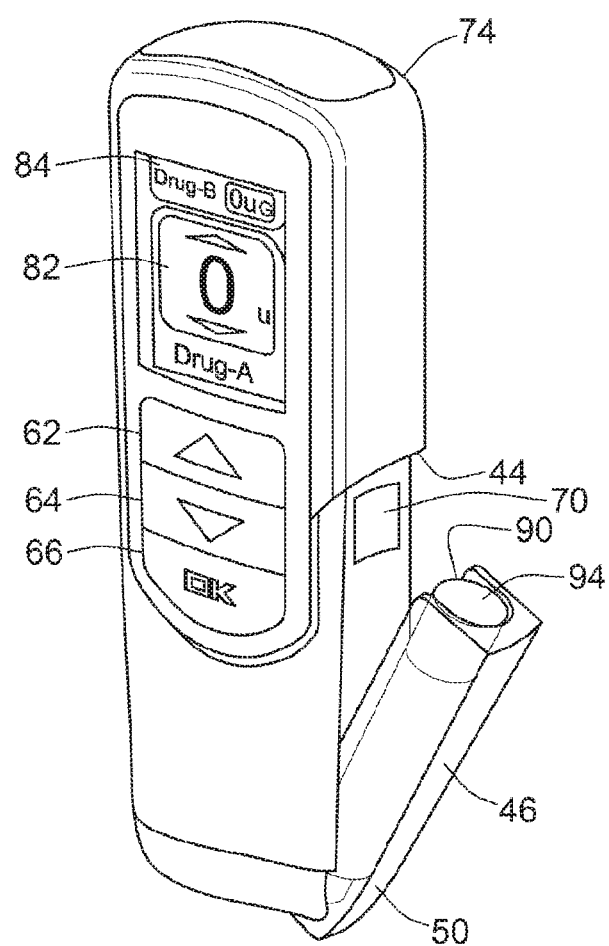
FIG. 9 illustrates a perspective view of the cartridge holder illustrated in FIG. 3 with one cartridge retainer in an open position.

In one preferred arrangement, the first and a second cartridge retainers 50, 52 comprise hinged cartridge retainers. These hinged retainers allow user access to the cartridges. For example, FIG. 9 illustrates a perspective view of the cartridge holder 40 illustrated in FIG. 2 with the first hinged cartridge retainer 50 in an open position. FIG. 9 illustrates how a user might access the first cartridge 90 by opening up the first retainer 50 and thereby having access to the first cartridge 90. A user might access the second cartridge 100 contained in the second hinged retainer 52 in a similar manner. Of course, if different sized cartridges are used, a user might access the second cartridge 100 in a different manner.

As illustrated in at least FIGS. 9 and 10, the drug delivery device 10 may comprise a cartridge detection system. Such a system may be used so as to confirm that the cartridge 90 has been properly inserted into the first cartridge retainer 50. In this illustrated arrangement, the cartridge detection device 70 is provided along an inner portion of the cartridge holder 40. An alternative location of the detection device may also be used.

In one preferred arrangement, the first or primary cartridge 90 containing the first medicament and the second or secondary cartridge 100 containing the second medicament are of similar dimensions. In a more preferred arrangement, the first cartridge 90 is a different size than the second cartridge. As just one example, the first medicament (e.g., a long acting insulin) could be provided within a 3 ml cartridge and this cartridge loaded into the first cavity. In addition, the second medicament (e.g., a GLP1) may be provided within a shortened 1.7 ml cartridge and could be loaded into the second cavity. Because the second hinged retainer contains a smaller sized cartridge, the second retainer would be sized differently than the first retainer. In a most preferred arrangement, the primary cartridge holder is designed so as to accept a 3 ml cartridge of insulin and the secondary holder is designed so as to accept a 1.7 ml cartridge of a GLP1. However, those of skill in the art will readily recognize, alternative cartridge holder structures and cartridge configurations could also be used.

In one arrangement, the cartridge holder 40 includes a cartridge dedication or coding system, such as a mechanical or an electronic cartridge dedication or coding system. Such a system would help to ensure that only a correctly coded cartridge and therefore the correct medicament could be loaded into each cartridge retainer. An electronic coding system that is able to detect a drug type, expiry date or other similar information would be a preferred arrangement. In such an electronic system, the microprocessor control unit could be programmed so that only a properly coded cartridge (and therefore the proper medicaments) would be acceptable in such a system. In such a coded system, the control unit could be programmed with an electronic lockout so as to lock out or disable the operator interface if an improperly coded cartridge was detected. Preferably, if such an incorrect cartridge were loaded, an error message would be displayed on the digital display 80 so as to notify the user that an incorrect cartridge (and therefore perhaps an incorrect medicament) had been loaded. Most preferably, if such an incorrect cartridge were loaded, the drug delivery device 10 could be programmed so as to lockout the user interface keys and prevent the user from setting a dose.

FIG. 10 illustrates one type of cartridge identification system 110 that may be used with the cartridge housing of drug delivery device 10. For example, FIG. 10 illustrates a cartridge 120 (similar to either the first or the second cartridge 90, 100) residing in a cartridge retainer 116 of a cartridge holder 118. Cartridge retainer 116 may be similar to the cartridge retainers 50, 52 illustrated in FIGS. 3 and 6. A cartridge 120 is illustrated as being nested within an internal cavity of the cartridge retainer 116. A label 122 is provided along an outer surface of the cartridge 120 and a bar code 124 is provided along a portion of this label 122.

In FIG. 10, the cartridge identification system 110 comprises a one dimensional ("1D") bar code reading system. In such a cartridge identification system 110, the barcode is provided along the cartridge surface and this bar code is an optical machine-readable representation of certain information. Alternatively, a two dimensional bar code reader could also be used. In such an arrangement, patterns of squares, dots, hexagons and other geometric patterns within images may be provided either on the cartridge outer surface itself or on a cartridge label. In addition, a cartridge detection device 70 may be provided along an inner surface wall of the system 110.

As just one example, the cartridge holder 118 may comprise a bar code reader 126. In one arrangement, this reader could comprise a 1D bar code reader comprising a light source 128 and a photo diode 130 and these two elements could be provided along an inner surface of the cartridge housing 118 adjacent the cartridge retainer 116. As illustrated, the light source 128 and a photo diode 130 may placed next to each other and directed towards the barcode on the cartridge. To read the bar code 124 provided on the label 122 of the cartridge 120, the light source 128 illuminates various lines provided on the label 122 as the cartridge is inserted into the cartridge housing 118. This light is then reflected and the photo diode 130 measures the intensity of the light reflected back from the light source 128 and a waveform is generated. The micro-processor coupled to this cartridge identification system 110 uses this generated waveform to measure the widths of the bars and spaces of the bar code 124. For example, dark bars in the bar code absorb the illuminated light while the white spaces reflect light.

As such, the voltage waveform generated by the photo diode will represent a duplicate of the bar and space pattern in the bar code. This waveform is then decoded by an algorithm provided in the micro-processor. Alternatively, a 2D barcode reader could also be used. One advantage of such a reader is that relative motion between the cartridge and the cartridge holder would not be required.

Utilizing such cartridge identification in the proposed drug delivery device 10 results in certain advantages. For example, such a cartridge identification arrangement can provide a method of retrieving information from the cartridges to determine the manufacturer or supplier of the cartridge. Such a system could also determine the type of medicament contained within the cartridge and then may also determine information relating to the drug contained within the cartridge. For example, the cartridge identification system could determine whether the cartridge that was inserted into the first retainer that is supposed to contain the primary medicament actually comprises a cartridge containing such a primary medicament. Such an identification scheme could comprise either a passive or active type of identification scheme. For example, it could comprise a passively (typically mechanical) or active (typically electrical) identification scheme. Such cartridge identification schemes may comprise identification through a microchip interface or through a radio frequency identification (RF-ID) interface. The cartridge may then comprise a readable memory comprising information about the cartridge. The memory may also be writeable, for example to store information on the used number of units, or information on an estimated remaining content in the cartridge and the date first used. The remaining content may be given in number of units, mg, ml and/or the like. The information on the remaining content may be updated when content has been expelled from the cartridge.

In an alternative arrangement, the cartridge holder 40 may be provided as a disposable cartridge holder. For example, in such an arrangement, a medical device supplier or a medicament supplier could supply the cartridge holder containing the two medicaments and these would not be replaceable by the end user. Therefore, once either the primary or secondary medicament of such a cartridge holder has been expended, the entire cartridge holder is removed from the drug dispensing portion of the drug delivery device and is discarded. Thereafter, the user or patient could then attach a new cartridge holder containing two fresh cartridges to the drug dispensing portion of the drug delivery device.

The disposable nature of such a cartridge holder would provide a number of advantages. For example, such a cartridge holder would help to prevent inadvertent medicament cross use: that is, using an incorrect primary or secondary medicament within the cartridge housing. Such an arrangement could also help prevent tampering of the medicaments and could also help eliminate counterfeit products from being used with the drug delivery device. In addition, the cartridge holder may be connected to the device main body where the device main body comprise a one dimensional ("1D") bar code reading system. Such a coding system could comprise a system similar to the coding system 110 discussed above.

Figure 11:
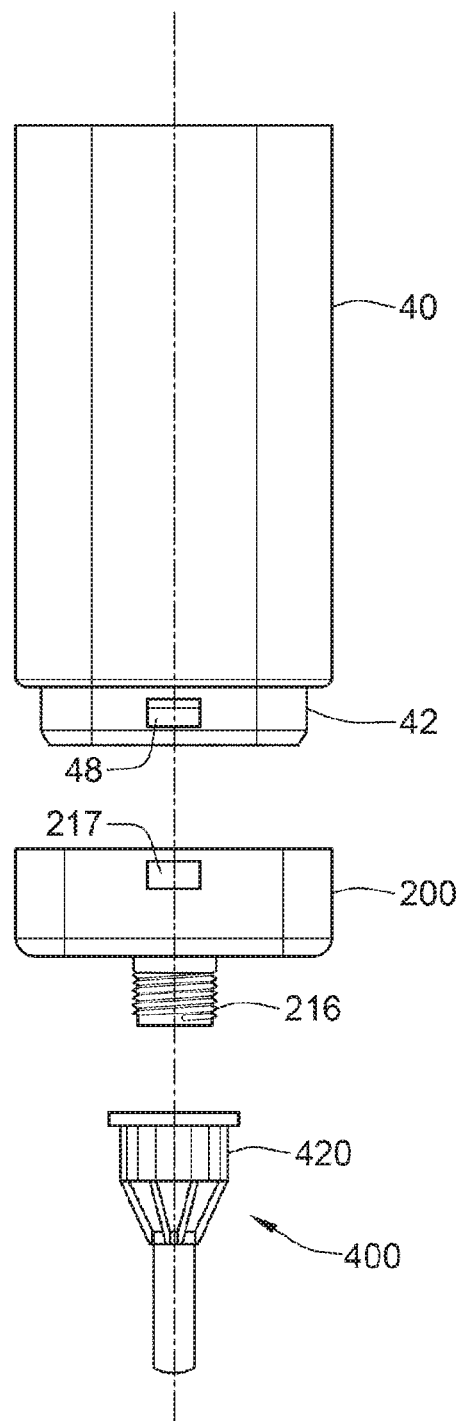
FIG. 11 illustrates a dispense interface and a dose dispenser that may be removably mounted on a distal end of the delivery device illustrated in FIGS. 1a, 1b, and 2.

As mentioned above when discussing FIGS. 2 and 3, a dispense interface 200 is coupled to the distal end of the cartridge holder 40. FIG. 11 illustrates a flat view of the dispense interface 200 unconnected to the distal end of the cartridge holder 40. A dose dispenser or needle assembly that may be used with the interface 200 is also illustrated and is provided in a protective outer cap 420.

Figure 12:
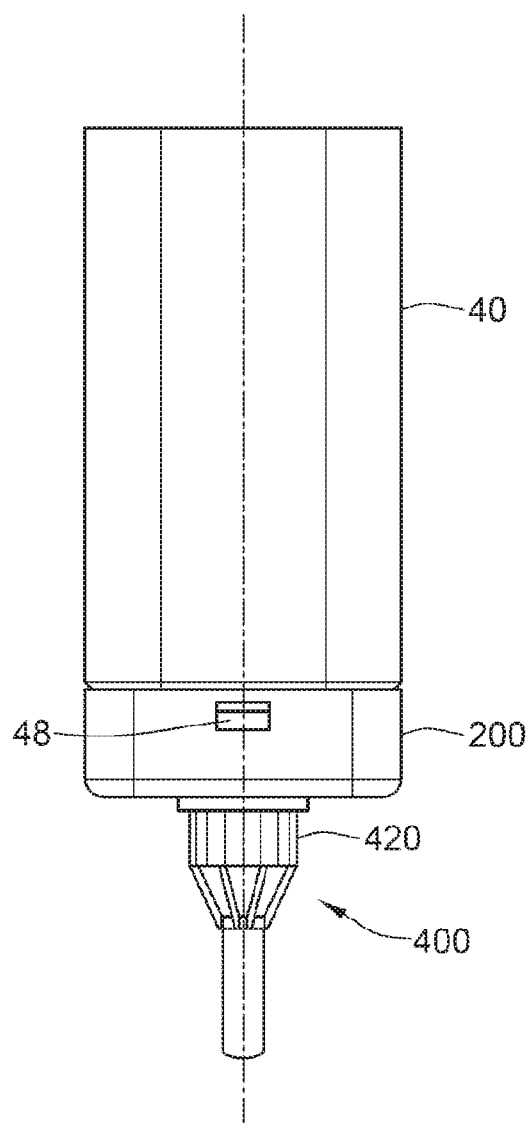
FIG. 12 illustrates the dispense interface and the dose dispenser illustrated in FIG. 11 mounted on a distal end of the delivery device illustrated in FIGS. 1a, 1b, and 2.

In FIG. 12, the dispense interface 200 illustrated in FIG. 11 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 13:
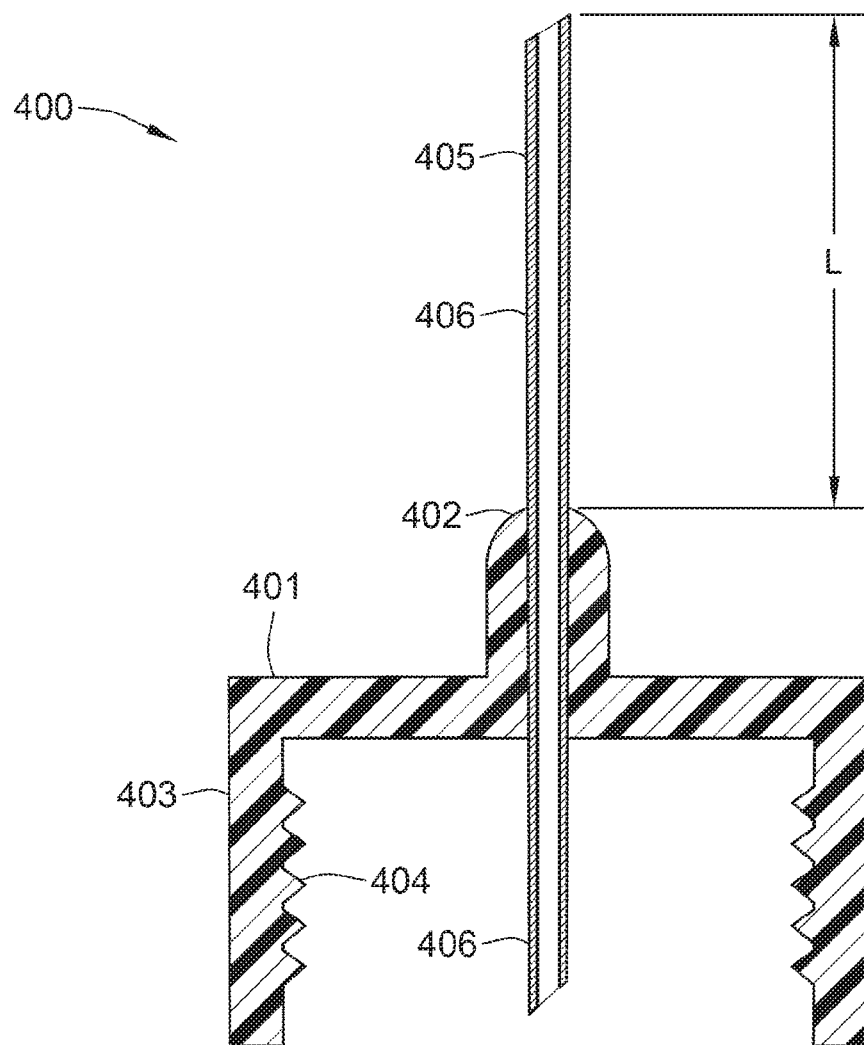
FIG. 13 illustrates one arrangement of the dose dispenser that may be mounted on a distal end of the delivery device.
Figure 14:
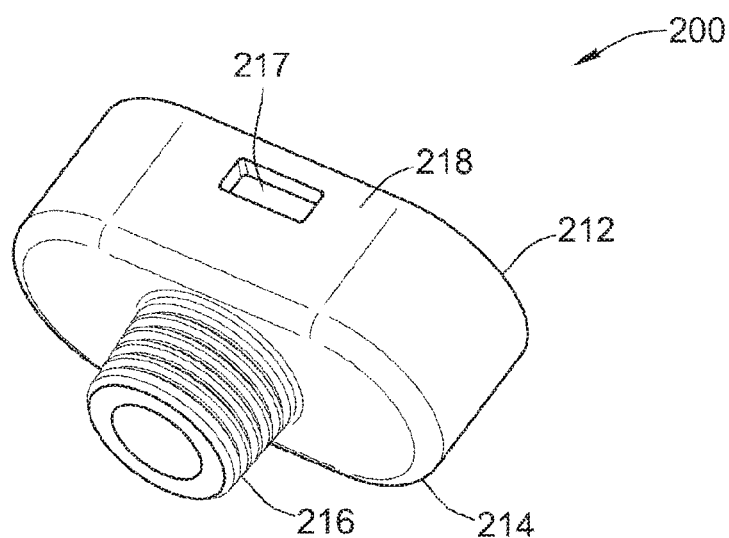
FIG. 14 illustrates a perspective view of the dispense interface illustrated in FIG. 11.
Figure 15:
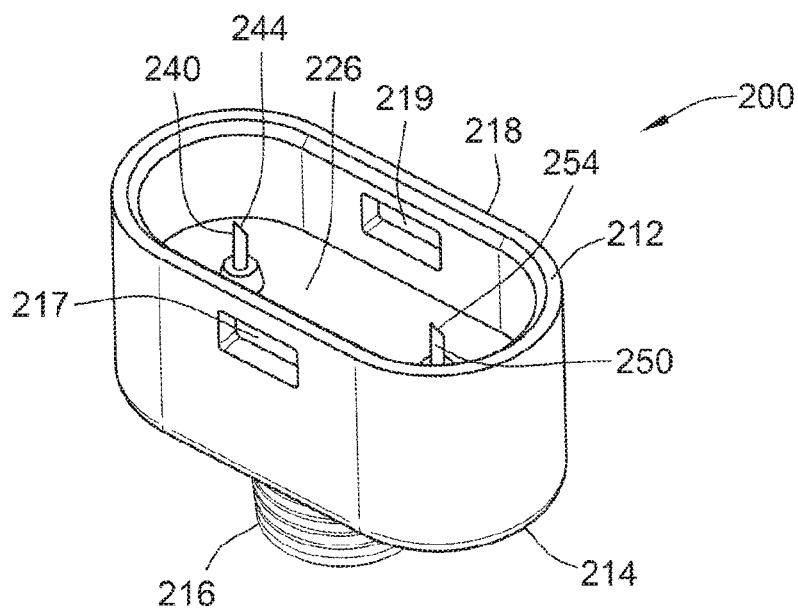
FIG. 15 illustrates another perspective view of the dispense interface illustrated in FIG. 11.

FIG. 12 also illustrates the needle assembly 400 and protective cover 420 coupled to the distal end of the dispense interface 200 that may be screwed onto the needle hub of the interface 200. FIG. 13 illustrates a cross sectional view of the double ended needle assembly 400 mounted on the dispense interface 200 in FIG. 12.

The needle assembly 400 illustrated in FIG. 13 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 11 and 12 provides a form fit around the outer surface 403 of the hub 401.

The needle assembly of FIG. 11 may be removably coupled to the distal end of the dispense interface 200. Referring now to FIGS. 11-12 and 14-19, one preferred arrangement of this interface 200 will now be discussed. In this one preferred arrangement, this interface 200 comprises:
a main outer body 210,
an first inner body 220,
a second inner body 230,
a first piercing needle 240,
a second piercing needle 250,
a valve seal 260, and
a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 15, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 11 and 12. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 13. Alternative releasable connectors may also be provided such as a snap lock, a snap lock released through threads, a bayonet lock, a form fit, or other similar connection arrangements.

Figure 16:
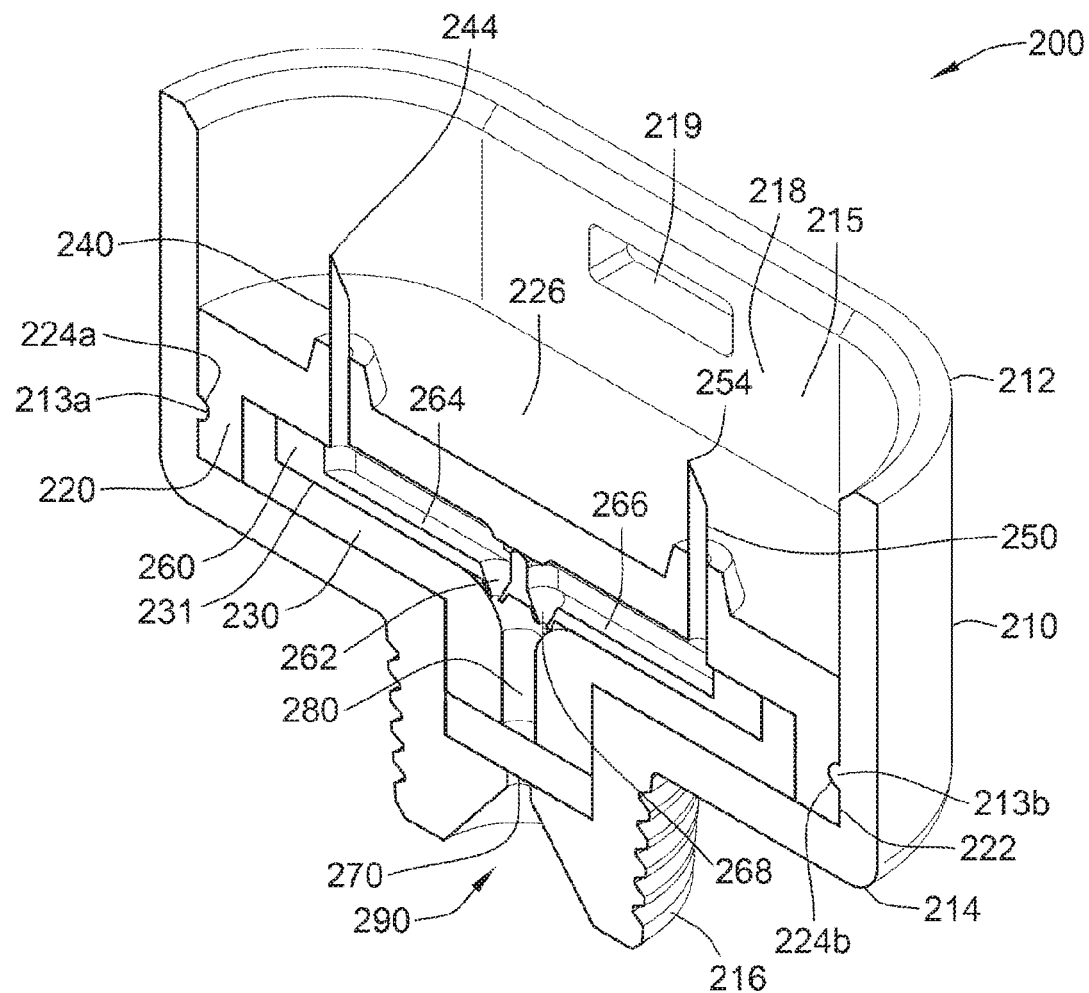
FIG. 16 illustrates a cross-sectional view of the dispense interface illustrated in FIGS. 11 and 12.
Figure 17:
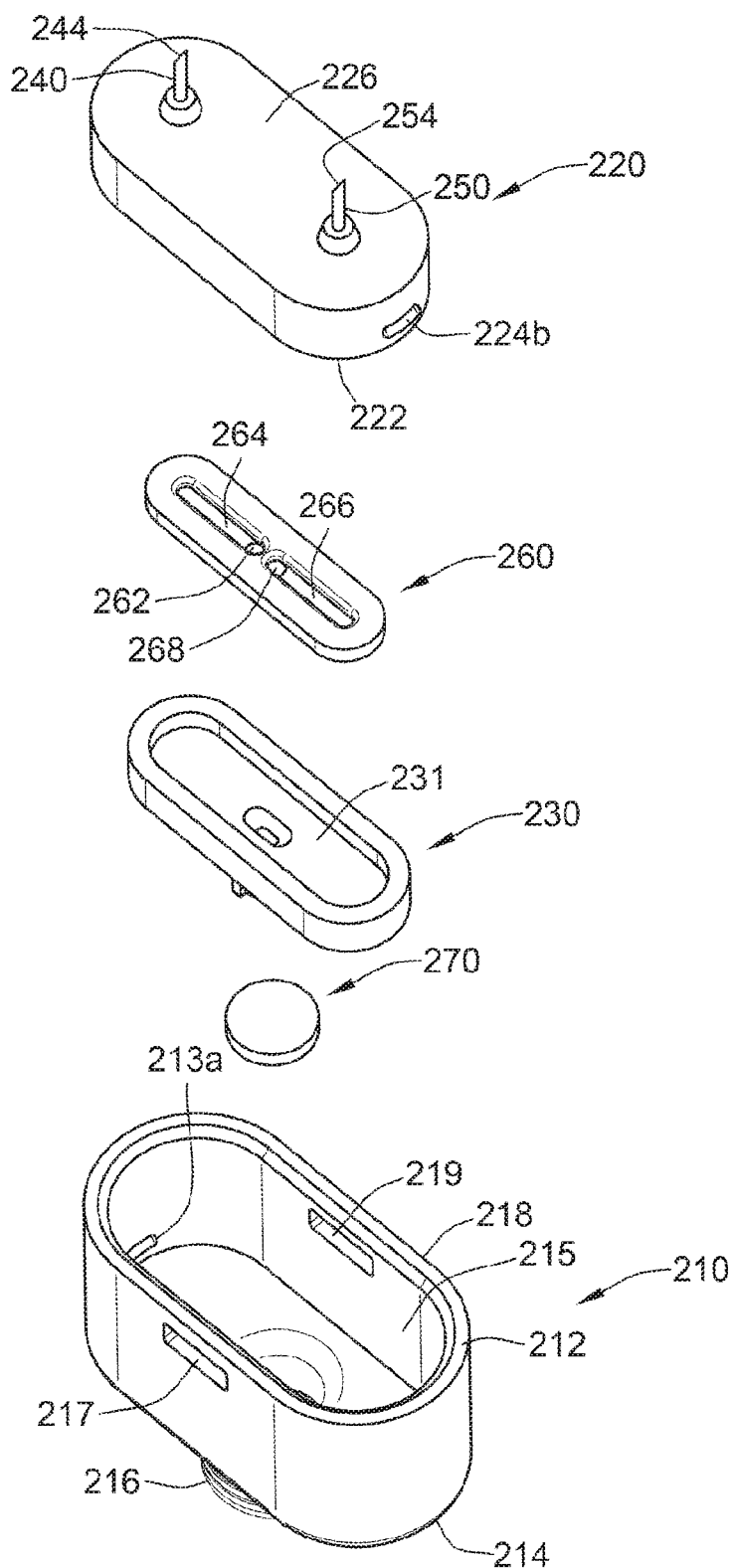
FIG. 17 illustrates an exploded view of the dispense interface illustrated in FIG. 11.
Figure 18:
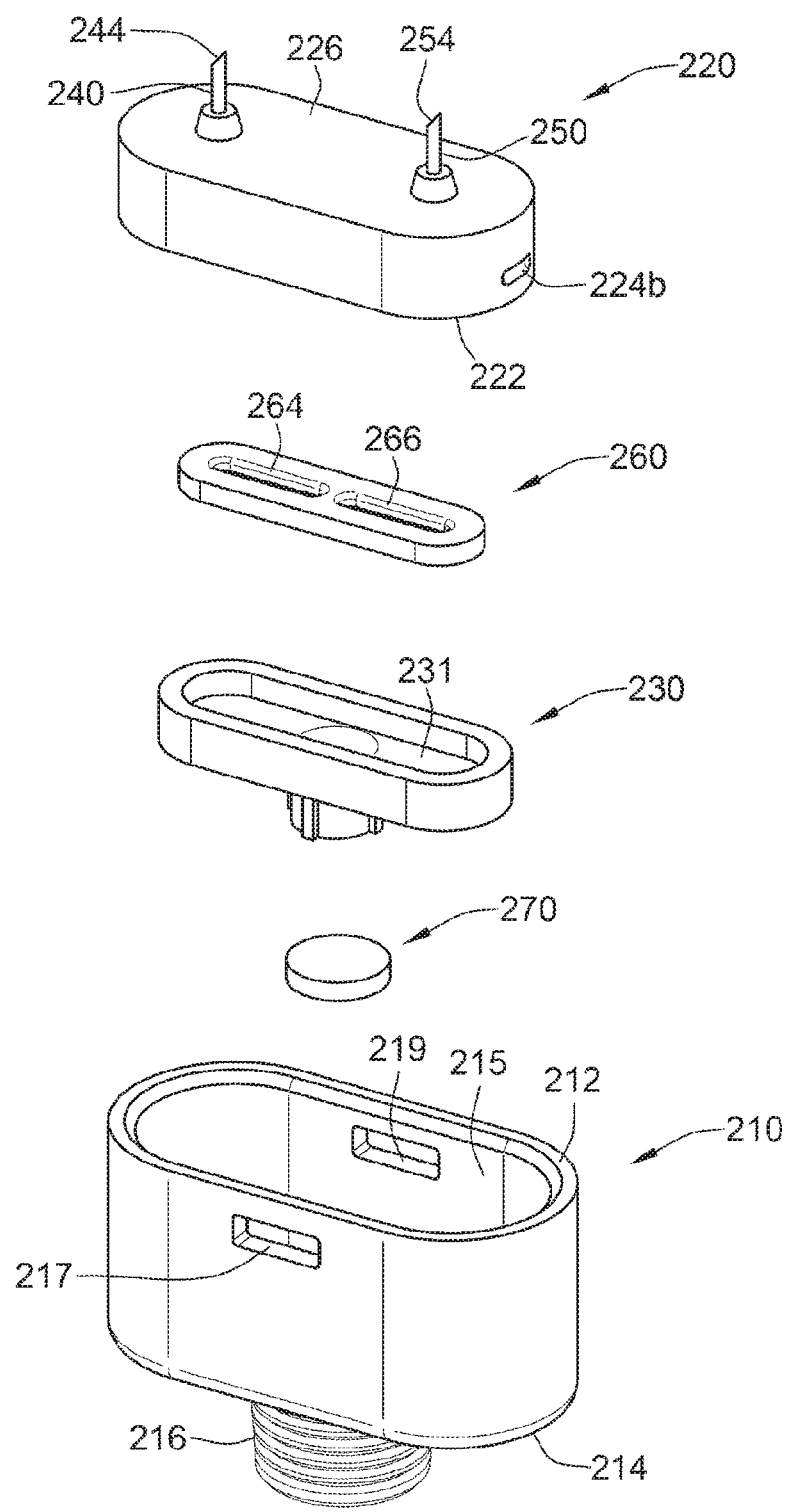
FIG. 18 illustrates another exploded view of the dispense interface illustrated in FIG. 11.

The dispense interface 200 further comprises a first inner body 220. Certain details of this inner body are illustrated in FIGS. 15-19. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 16, the extending wall 218 of the main outer body 210 is provided with a first rib 213*a* and a second rib 213*b*. This first rib 213*a* is also illustrated in FIG. 17. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

In addition, as can be seen in FIGS. 15-18, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 16 illustrates the position of the valve seal 260, seated between the first inner body 220 and the second inner body 230. During an injection step, this seal valve 260 helps to prevent the primary medicament in the first pathway from migrating to the secondary medicament in the second pathway while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position.

As such, when a double ended needle assembly is attached to the needle hub of the interface (such as the double ended needle illustrated in FIG. 13), the output fluid path allows both medicaments to be in fluid communication with the attached needle assembly.

The hub interface 200 further comprises a second inner body 230. As can be seen from FIG. 16, this second inner body 230 has an upper surface that defines a recess, and the valve seal 260 is positioned within this recess. Therefore, when the interface 200 is assembled as shown in FIG. 16, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Although not shown, the dispense interface 200 could be supplied by a manufacturer as being contained in a protective and sterile capsule or container. As such, where the user would peel or tear open a seal or the container itself to gain access to the sterile single dispense interface. In some instances it might be desirable to provide two or more seals for each end of the interface. The seal may allow display of information required by regulatory labeling requirements. When a double ended needle assembly is used as a single dispense assembly to deliver the single dose of both medicaments, it is preferred that the interface is designed to be economical and safe for allowing the user to attach a new hub for each injection.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 19:
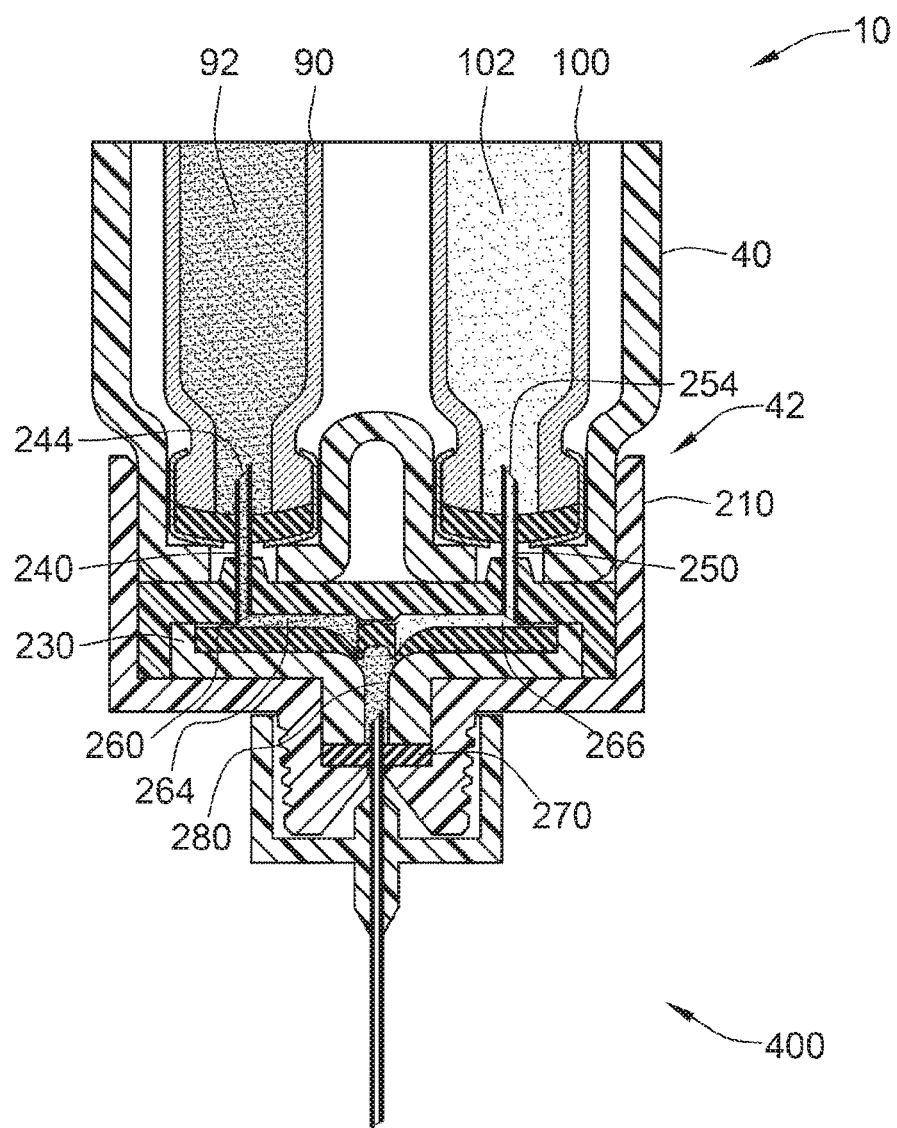
FIG. 19 illustrates a cross-sectional view of the dispense interface and dose dispenser mounted onto a drug delivery device, such as the device illustrated in FIGS. 7a and 1b.

FIG. 19 illustrates the dispense interface 200 after it has been mounted onto the distal end 42 of the cartridge holder 40 of the drug delivery device 10 illustrated in FIG. 1. A double ended needle 400 is also mounted to the distal end of this interface.

The cartridge holder 40 is illustrated as having a first cartridge containing a fast medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 19 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 19, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 19, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In one arrangement, the drug delivery device 10 comprises a detection sensor so as to sense or confirm that the dispense interface 200 has been correctly mounted onto the cartridge housing 40. Such a detection sensor may comprise either a mechanical, an electrical, a capacitive, an inductive or other similar type sensor. As illustrated, this sensor may be provided near the distal end of the cartridge housing.

In addition, the drug delivery device may comprise a similar detection sensor for detecting the presence of the dose dispenser. For example, such a sensor may be provided adjacent the needle hub of the interface 200. Preferably, either or both of the detection sensors would be communicatively coupled to the micro-processor. Optionally, the micro-processor would be programmed so as prevent a user from setting a dose with the drug delivery device 10 unless the device has detected that both the dispense interface 200 has been properly mounted to the cartridge holder 40 and that a dose dispenser has been properly mounted onto the interface. If either the dispense interface or the dose dispenser has been detected as being incorrectly mounted, the user may be locked out of the device and a connection error may be shown on the digital display 80.

Additionally, the dispense interface 200 could incorporate a safety shield device that would prevent accidental needle sticks and reduce the anxiety experienced by users who suffer from needle phobia. The exact design of the safety shield is not critical to the presently described drug delivery device and system. However, a preferred design is one that is operably connected to drug delivery device 10. In such a design, the activation of the safety shield could unlock the drug delivery system or enable medicament to be dispensed via the dispense interface and dose dispenser. Another preferred design would physically prevent insertion of the used drug dispense interface into the patient (e.g., a single use needle-guard type arrangement). Preferably, the interface is configured to work with a conventional double ended needle assembly. Alternatively, the interface may be configured to work with a non-conventional needle assembly.

One example of such a non-conventional-needle assembly may comprise a coded needle assembly.

In one preferred electro-mechanical drug delivery device, a single dispense assembly comprising a catheter may be coupled to the interface 200.

In one preferred arrangement, the dispense interface 200 is a disposable interface and as such, the needle hub comprises a disposable element that is discarded when either the first or the second cartridge in the device is replaced (e.g., when such cartridge is empty). In one arrangement, the dispense interface 200 may be provided in a drug delivery kit. For example, in one drug delivery kit arrangement, a needle assembly interface can be provided with each replacement cartridge. In an alternative kit arrangement, a plurality of double ended needle assemblies are provided with a multi-use dispense interface.

Figure 20:
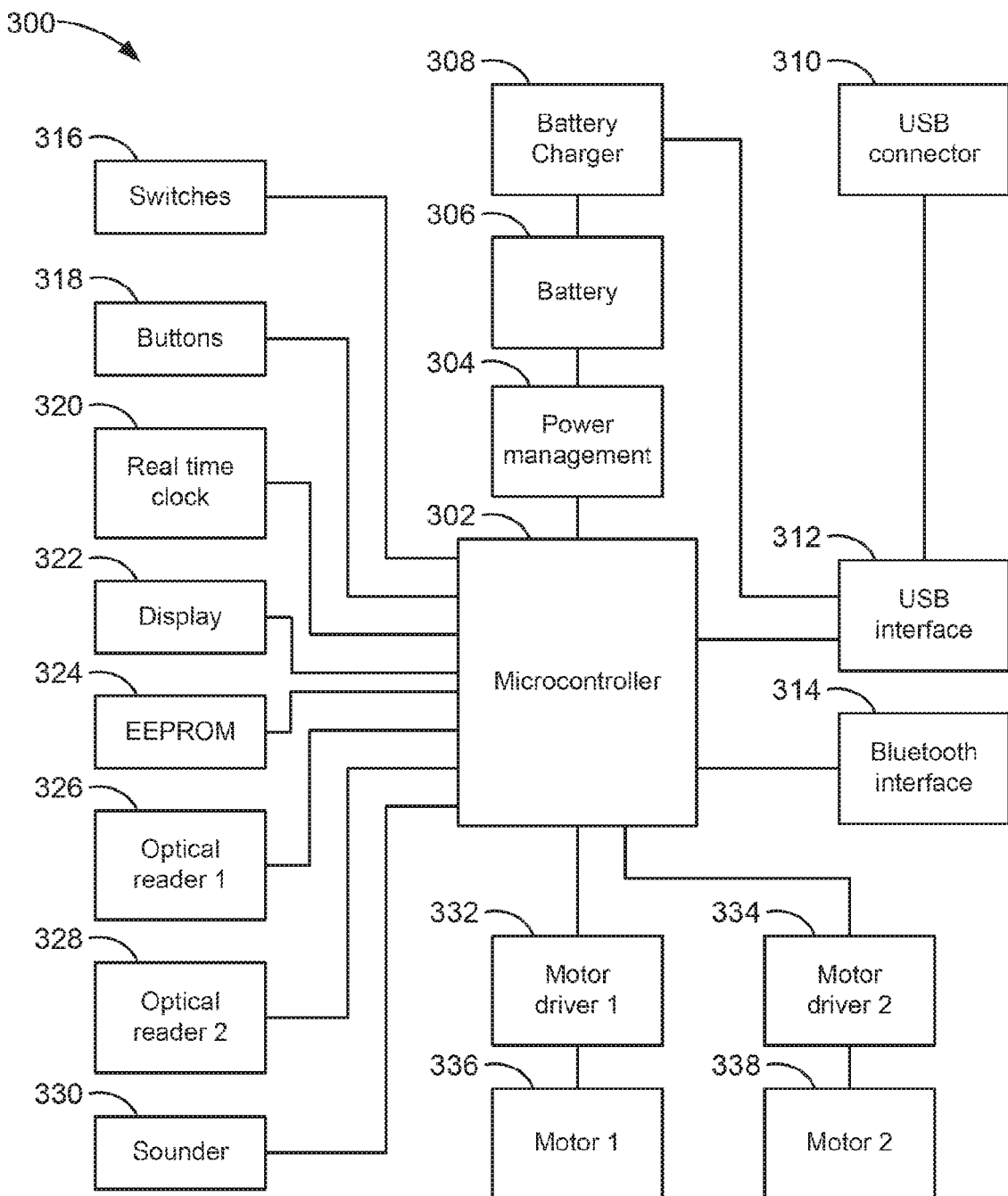
FIG. 20 illustrates a block diagram functional description of a control unit for operation of the drug delivery device illustrated in FIG. 11.
Figure 21:
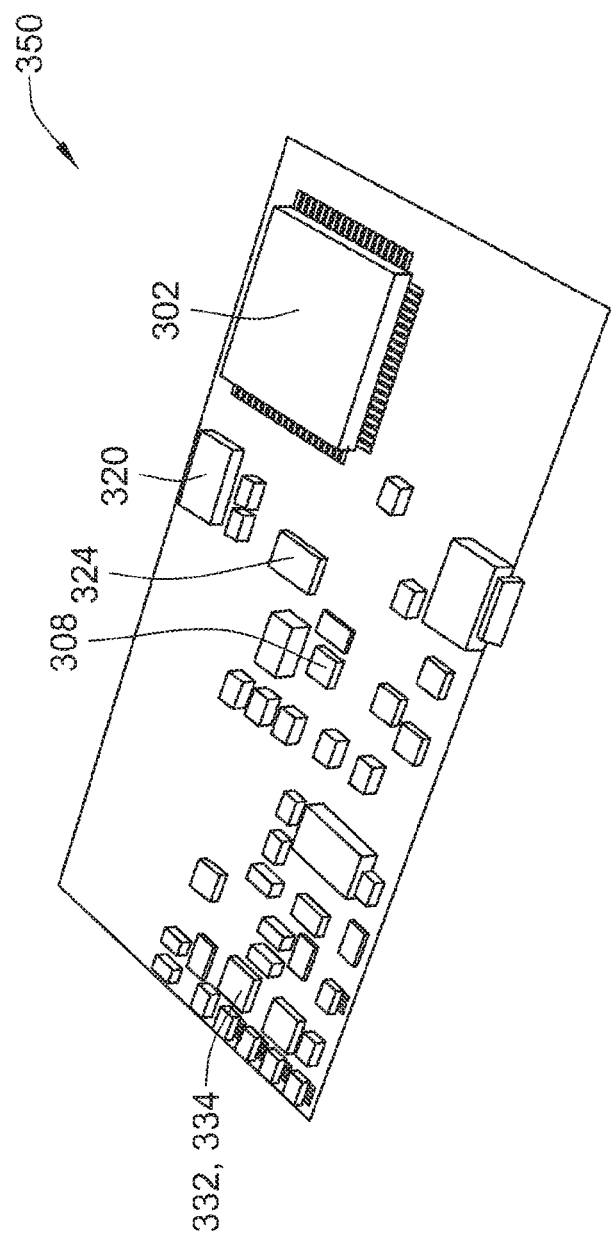
FIG. 21 illustrates a printed circuit board assembly of the drug delivery device illustrated in FIG. 11.

FIG. 20 illustrates a functional block diagram of a control unit to operate and control the drug delivery device illustrated in FIG. 1. FIG. 21 illustrates one arrangement of a printed circuit board (PCB) or printed circuit board assembly (PCBA) 350 that may comprise certain portions of the control unit illustrated in FIG. 20.

Referring now to both FIGS. 20 and 21, it may be seen that the control unit 300 comprises a microcontroller 302. Such a microcontroller may comprise a Freescale MCF51JM microcontroller. The microcontroller is used to control the electronic system for the drug delivery device 10. It includes internal analogue to digital converters and general purpose digital I/O lines. It can output digital Pulse Width Modulated (PWM) signals. It includes an internal USB module. In one arrangement, a USB protection circuit such as ON-Semi NUP3115 may be implemented. In suet, an implementation, the actual USB communications may be provided on board the microcontroller 302.

The control unit further comprises a power management module 304 coupled to the microcontroller 302 and other circuit elements. The power management module 304 receives a supply voltage from a main power source such as the battery 306 and regulates this supply voltage to a plurality of voltages required by other circuit components of the control unit 300. In one preferred control unit arrangement, switched mode regulation (by means of a National Semiconductor LM2731) is used to step up the battery voltage to 5V, with subsequent linear regulation to generate other supply voltages required by the control unit 300.

The battery 306 provides power to the control unit 300 and is preferably supplied by a single lithium-ion or lithium-polymer cell. This cell may be encapsulated in a battery pack that contains safety circuitry to protect against overheating, overcharging and excessive discharge. The battery pack may also optionally contain coulomb counting technology to obtain an improved estimate of remaining battery charge.

A battery charger 308 may be coupled to the battery 306. One such battery charger may be based on Texas Instruments (TI) BQ24150 along with other supporting software and hardware modules. In one preferred arrangement, the battery charger 308 takes energy from the external wired connection to the drug delivery device 10 and uses it to charge the battery 306. The battery charger 308 can also be used to monitor the battery voltage and charge current to control battery charging. The battery charger 308 can also be configured to have bidirectional communications with the microcontroller 302 over a serial bus. The charge status of the battery 306 may be communicated to the microcontroller 302 as well. The charge current of the battery charger may also be set by the microcontroller 302.

The control unit may also comprise a USB connector 310. A micro USB-AB connector may be used for wired communications and to supply power to the device.

The control unit may also comprise a USB interface 312. This interface 312 may be external to the microcontroller 302. The USB interface 312 may have USB master and/or USB device capability. The USB interface 312 may also provide USB on-the-go functionality. The USB interface 312 external to the microcontroller also provides transient voltage suppression on the data lines and VBUS line.

An external Bluetooth interface 314 may also be provided. The Bluetooth interface 314 is preferably external to the microcontroller 302 and communicates with this controller 302 using a data interface.

Preferably, the control unit further comprises a plurality of switches 316. In the illustrated arrangement, the control unit 300 may comprise eight switches 316 and these switches may be distributed around the device. These switches 316 may be used to detect and or confirm at least the following:

Whether the dispense interface 200 has been properly attached to the drug delivery device 10;

Whether the removable cap 18 has been properly attached to the main body 20 of the drug delivery device 10;

Whether the first cartridge retainer 50 of the cartridge holder 40 for the first cartridge 90 has been properly closed;

Whether the second cartridge retainer 52 of the cartridge holder 40 for the second cartridge 100 has been properly closed;

To detect the presence of the first cartridge 90;

To detect the presence of the second cartridge 100;

To determine the position of the stopper 94 in the first cartridge 90; and

To determine the position of the stopper 104 in the second cartridge 100.

These switches 316 are connected to digital inputs, for example to general purpose digital inputs, on the microcontroller 302. Preferably, these digital inputs may be multiplexed in order to reduce the number of input lines required. Interrupt lines may also be used appropriately on the microcontroller 302 so as to ensure timely response to changes in switch status.

In addition, and as described in greater detail above, the control unit may also be operatively coupled to a plurality of human interface elements or push buttons 318. In one preferred arrangement, the control unit 300 comprises eight push buttons 318 and these are used on the device for user input for the following functions:

Dose dial up;
Dose dial down;
Sound level;
Dose;
Eject;
Prime;
Dose set; and
OK.

These buttons 318 are connected to digital inputs, for example to general purpose digital inputs, on the microcontroller. Again, these digital inputs may be multiplexed so as to reduce the number of input lines required. Interrupt lines will be used appropriately on the microcontroller to ensure timely response to changes in switch status. In an example embodiment, the function of one or more buttons may be replaced by a touch screen.

In addition, the control unit 300 comprises a real time clock 320. Such a real time clock may comprise an Epson RX4045 SA. The real-time clock 320 may communicate with the microcontroller 302 using a serial peripheral interface or similar.

A digital display module 322 in the device preferably uses LCD or OLEO technology and provides a visual signal to the user. The display module incorporates the display itself and a display driver integrated circuit. This circuit communicates with the microcontroller 302 using a serial peripheral interface or parallel bus.

The control unit 300 also comprises a memory device, for example volatile and non-volatile memory. Volatile memory may be random access memory (RAM), for example static RAM or dynamic RAM and/or the like, as working memory of microcontroller 302. Non-volatile memory may be read only memory (ROM), FLASH memory or electrically erasable programmable read-only memory (EEPROM), such as an EEPROM 324. Such an EEPROM may comprise an Atmel AT25640. The EEPROM may be used to store system parameters and history data. This memory device 324 communicates with the processor 302 using a serial peripheral interface bus.

The control unit 300 further comprises a first and a second optical reader 326, 328. Such optical readers may comprise Avago ADNS3550. These optical readers 326, 328 may be optional for the drug delivery device 10 and are, as described above, used to read information from a cartridge when such a cartridge is inserted into either the first or the second cartridge retainers 50, 52. Preferably, a first optical reader is dedicated for the first cartridge and the second optical reader is dedicated for the second cartridge. An integrated circuit designed for use in optical computer mice may be used to illuminate a static 2D barcode on the drug cartridge, positioned using a mechanical feature on the drug cartridge, and read the data it contains. This integrated circuit may communicate with the microcontroller 302 using a serial peripheral interface bus. Such a circuit may be activated and deactivated by the microcontroller 302 e.g., to reduce power consumption when the circuit is not needed, for example by extinguishing the cartridge illumination when data is not being read.

As previously mentioned, a sounder 330 may also be provided in the drug delivery device 10. Such a sounder may comprise a Star Micronics MZT03A. The proposed sounder may be used to provide an audible signal to the user. The sounder 330 may be driven by a pulse-width modulation (PWM) output from the microcontroller 302. In an alternative configuration, the sounder may play polyphonic tones or jingles and play stored voice commands and prompts to assist the user in operating or retrieving information from the device.

The control unit 300 further comprises a first motor driver 332 and a second motor driver 334. The motor drive circuitry may comprise Freescale MPC17C724 and is controlled by the microcontroller 302. For example, where the motor drive comprises a stepper motor drive, the drive may be controlled using general purpose digital outputs. Alternatively, where the motor drive comprises a brushless DC motor drive, the drive may be controlled using a Pulse Width Modulated (PWM) digital output. These signals control a power stage, which switches current through the motor windings. The power stage requires continuous electrical commutation. This may for example increase device safety, decreasing the probability of erroneous drug delivery.

The power stage may consist of a dual H-bridge per stepper motor, or three half-bridges per brushless DC motor. These may be implemented using either discrete semiconductor parts or monolithic integrated circuits.

The control unit 300 further comprises a first and a second motor 336, 338, respectively. As explained in greater detail below, the first motor 336 may be used to move the stopper 94 in the first cartridge 90. Similarly, the second motor 338 may be used to move the stopper 104 in the second cartridge.

The motors can be stepper motors, brushless DC motors, or any other type of electric motor. The type of motor may determine the type of motor drive circuit used. The electronics for the device may be implemented with one main, rigid printed circuit board assembly, potentially with additional smaller flexible sections as required, e.g., for connection to motor windings and switches.

The micro-processor provided on the PCBA 350 will be programmed to provide a number of features and carry out a number of calculations. For example, and perhaps most importantly, the micro-processor will be programmed with an algorithm for using a certain therapeutic dose profile to calculate at least a dose of the secondary medicament based at least in part on the selected dose of the primary medicament.

For such a calculation, the controller may also analyze other variables or dosing characteristics in calculating the amount of second medicament to administer. For example, other considerations could include at least one or more of the following characteristics or factors:

Time since last dose;
Size of last dose;
Size of current dose;
Current blood glucose level;
Blood glucose history;
Maximum and/or minimum permissible dose size;
Time of day;
Patient's state of health;
Exercise taken; and
Food intake.

These parameters may also be used to calculate the size of both the first and the second dose size In one arrangement, and as will be described in greater detail below, a plurality of different therapeutic dose profiles may be stored in the memory device or devices operatively coupled to the micro-processor. In an alternative arrangement, only a single therapeutic dose profile is stored in the memory device operatively coupled to the micro-processor.

The presently proposed electromechanical drug delivery device is of particular benefit to patients with dexterity or computational difficulties. With such a programmable device, the single input and associated stored predefined therapeutic profile removes the need for the user or patient to calculate their prescribed dose every time they use the device. In addition, the single input allows easier dose setting and dispensing of the combined compounds.

In addition to computing the dose of the second medicament, the micro-processor can be programmed to achieve a number of other device control operations. For example, the micro-processor may be programmed so as to monitor the device and shut down the various elements of the system to save electrical energy when the device is not in use. In addition, the controller can be programmed to monitor the amount of electrical energy remaining in the battery 306. In one preferred arrangement, an amount of charge remaining in the battery can be indicated on the digital display 80 and a warning may be given to the user when the amount of remaining battery charge reaches a predetermined threshold level. In addition, the device may include a mechanism for determining whether there is sufficient power available in the battery 306 to deliver the next dose, or it will automatically prevent that dose from being dispensed. For example, such a monitoring circuit may check the battery voltage under different load conditions to predict the likelihood of the dose being completed. In a preferred configuration the motor in an energized (but not moving) condition and a not energized condition may be used to determine or estimate the charge of the battery.

Preferably, the drug delivery device 10 is configured to communicate via a data link (i.e., either wirelessly or hard wired) with various computing devices, such as a desktop or laptop computer. For example, the device may comprise a Universal Serial Bus (USB) for communicating with a PC or other devices. Such a data link may provide a number of advantages. For example, such a data link may be used to allow certain dose history information to be interrogated by a user. Such a data link could also be used by a health care professional to modify certain key dose setting parameters such as maximum and minimum doses, a certain therapeutic profile, etc. The device may also comprise a wireless data link, for example an IRDA data link or a Bluetooth data link. A preferred Bluetooth module comprises a Cambridge Silicon Radio (CSR) Blue core 6.

In an example embodiment, the device has USB On-The-Go (USB OTG) capability. USB OTG may allow the drug delivery device 10 to generally fulfill the role of being slave to a USB host (e.g., to a desktop or notebook computer) and to become the host themselves when paired with another slave device (e.g. a BGM).

For example, standard USB uses a master/slave architecture. A USB Host acts as the protocol master, and a USB 'Device' acts as the slave. Only the Host can schedule the configuration and data transfers over the link. The Devices cannot initiate data transfers, they only respond to requests given by a host. Use of OTG in the drug delivery device 10 introduces the concept that the drug delivery device can switch between the master and slave roles. With USB OTG, the device 10 at one time be a 'Host' (acting as the link master) and a 'Peripheral' (acting as the link slave) at another time.

Figure 22:
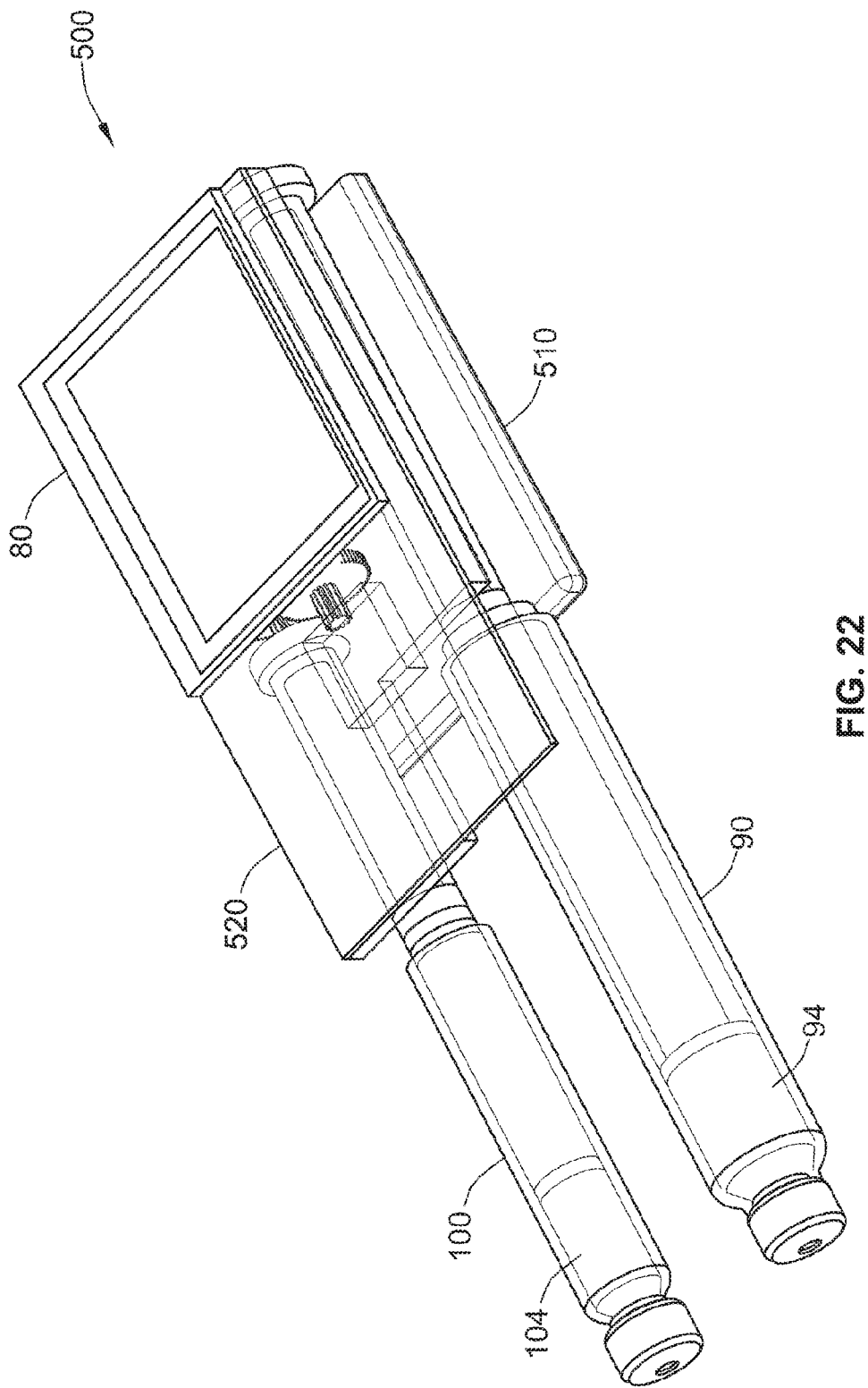
FIG. 22 illustrates a schematic view of a drive mechanism for use with the drug delivery device illustrated in FIGS. 1a and 1b.

FIG. 22 illustrates various internal components of the drug delivery device 10 illustrated in FIGS. 1*a* and 1*b* including one preferred arrangement of a drive train 500. As illustrated, FIG. 22 illustrates the digital display 80, a printed circuit board assembly (PCBA) 520 (such as the PCB 350 illustrated in FIG. 21), along with a power source or battery 510. The PCBA 520 may be positioned between the digital display 80 and a drive train 500 with the battery or power source 510 positioned beneath this drive train. The battery or power source 510 is electronically connected to provide power to the digital display 80, the PCBA 520 and the drive train 500. As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 in the distal position. The stopper 104 of the second cartridge 100 (ordinarily containing the second medicament 102) is illustrated in a similar position.

With reference to FIG. 22, it may be seen that there is provided a first region defining a suitable location for a power source 510 such as a replaceable battery or batteries. The power source 510 may comprise a rechargeable power source and may be recharged while the power source 510 remains in the device. Alternatively, the power source 510 may be removed from the drug delivery device 10 and recharged externally, for example, by way of a remote battery charger. This power source may comprise a Lithium-Ion or Lithium-polymer power source. In this preferred arrangement, the battery 510 comprises a generally flat and rectangular shaped power source.

Figure 23:
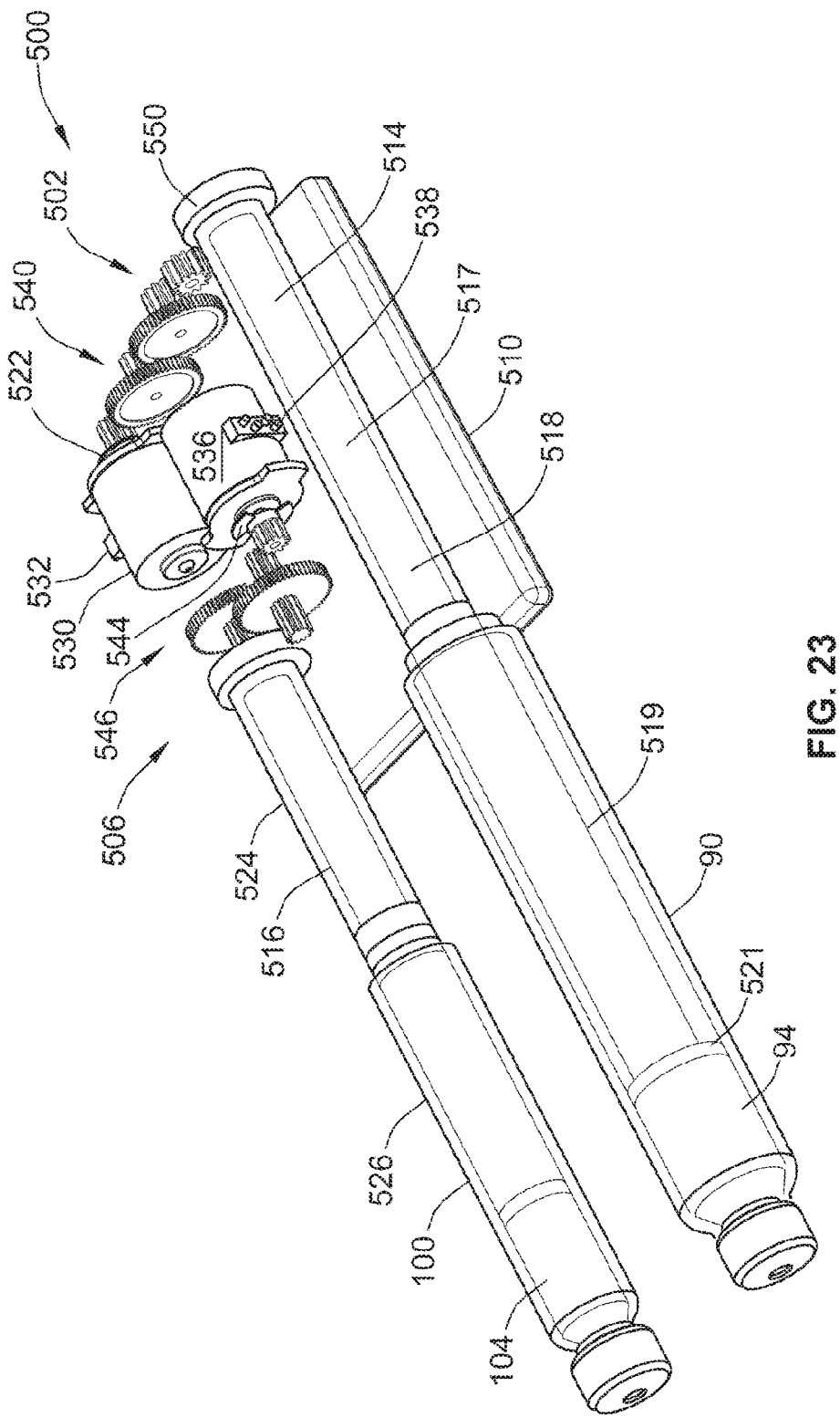
FIG. 23 illustrates another schematic view of the drive mechanism illustrated in FIG. 22.

FIG. 23 illustrates the first arrangement of the electro-mechanical system illustrated in FIG. 22 with both the digital display 80 and the PCBA 520 omitted. As illustrated in FIG. 23, the electro-mechanical system 500 operates to expel a dose from the first cartridge 90 containing the primary medicament 92 and the second cartridge 100 containing the secondary medicament 102. Again, as illustrated in FIG. 23, the first and second cartridges 90, 100 are illustrated in an empty state having stoppers at a most distal position.

In this preferred electro-mechanical system 500, the system comprises an independent mechanical driver for each cartridge 90, 100. That is, an independent mechanical driver 502 operates to expel a dose from the first cartridge 90 and an independent mechanical driver 506 operates to expel a dose from the second cartridge 100. In an alternative electro-mechanical system 500 operating on three different medicaments, three independent mechanical drivers could be provided. The independent mechanical drivers act under control of the motor drivers 332, 334 of the control unit 300 (see, e.g., FIG. 20).

The first independent mechanical driver 502 operates to expel a dose from the first cartridge 90. This first driver 502 comprises a first motor 530 that is operatively coupled to a first gearing arrangement 540. To energize this motor 530, a connector 532 is provided as a means of electrically connecting to the motor driver 332. This first gearing arrangement 540 is mechanically linked to a proximal portion of the first telescoping piston rod 514. The first telescoping piston rod 514 is illustrated in a fully extended position having a distal end 521 acting on the stopper 94 of the first cartridge 90.

As this gearing arrangement 540 is driven by the output shaft of the first motor 530, this arrangement 540 rotates the proximal portion 518 of the first telescoping piston rod 514. As this proximal portion 518 of the piston rod 514 is rotated, the second or distal portion 519 of the piston rod 514 is driven in a distal direction.

Preferably, the proximal portion 518 of the telescope piston rod 514 comprises an external thread 517. This thread 517 engages the distal portion 519 which has in integrated nut comprising a short threaded section at a proximal end of the distal portion 519. This distal portion 519 is prevented from rotating via a key acting in a keyway. Such a keyway may pass through the middle of first telescope 514. Therefore, when the first gearbox arrangement 540 causes rotation of the proximal section 518, rotation of the proximal portion 518 acts upon the distal end 521 to thereby drive the distal portion of telescope piston rod to extend along the longitudinal axis.

Moving in this distal direction, the distal end 521 of the second portion 519 of the piston rod 514 exerts a force on a stopper 94 contained within the first cartridge 90. With this distal end 521 of the piston rod 514 exerting a force on the stopper, the user selected dose of the first medicament 92 is forced out of the cartridge 90 and into an attached dispense interface 200 and consequently out an attached needle assembly 400 as previously discussed above.

A similar injection operation occurs with the second independent driver 506 when the controller first determines that a dose of the second medicament 102 is called for and determines the amount of this dose. As previously mentioned, in certain circumstances, the controller may determine that a dose of the second medicament 102 may not be called for and therefore this second dose would be "set" to a "0" dose.

Preferably, motors 530, 536 comprise motors suitable for electronic commutation. Most preferably, such motors may comprise either a stepper motor or a brushless DC motor.

To inject a dose of the primary and secondary medicaments 92, 102, a user will first select a dose of the primary medicament by way of the human interface components on the display 80. (see, e.g., FIGS. 1 and 4). After a dose of the drug from the primary medicament 92 has been selected, the microcontroller will utilize a previously stored algorithm for determining the dose size of a second drug 102 from a second medicament cartridge. This pre-defined algorithm may help to determine at least in part the dose of the second medicament 102 based on a pre-selected therapeutic profile. In one arrangement, these therapeutic profiles are user selectable. Alternatively, these therapeutic profiles may be password protected and selectable only by a person authorized with the password, such a physician or patient care giver. In yet another arrangement, the therapeutic profile may only be set by the manufacture or the supplier of the drug delivery device 10. As such, the drug delivery device 10 may be provided with only one profile.

When the dose sizes of the first and second medicaments have been established, the user can press the injection button 74 (see e.g., FIG. 4). By pressing this button 74, the motor drivers 332, 334 energize both the first and the second motors 530, 536 to begin the injection process described above.

The piston rods 514, 516 are preferably movable between a first fully withdrawn position (not shown) and a second fully extended portion (as shown in FIGS. 22 and 23). With the piston rods 514, 516 in the withdrawn position, the user will be allowed to open up the respective cartridge retainer and remove an empty cartridge. In one preferred arrangement, an end stop switch may be provided in the main body 14 of the drug delivery device 10 so as to detect when either or both of the piston rods 514, 516 are in a fully withdrawn position. Tripping of the end stop switch may release a catch or other fastening device so as to allow access to the main body for replacement of either cartridge 90, 100.

In one preferred arrangement, both the first and second motors 530, 536 operate simultaneously so as to dispense the user selected dose of the first medicament 92 and the subsequently calculated dose of the second medicament 102 simultaneously. That is, both the first and the second independent mechanical drivers 502, 506 are capable of driving the respective piston rods 514, 516 either at the same or a different time. In this manner, now referring to the dispense interface 200 previously discussed, the first medicament 92 enters the holding chamber 280 of the dispense interface 200 at essentially the same time as the second medicament. One advantage of such an injecting step is that a certain degree of mixing can occur between the first and second medicament 92, 102 prior to actual dose administration.

If after an injection, the patient determines that one or more of the cartridges 90,100 is spent and therefore needs to be exchanged, the patient can follow the following method of cartridge exchange:

Remove the double ended needle from the dispense interface 200;

Remove the dispense interface 200 from the cartridge holder 40 of the device 10;

Enable a menu option on the digital display 80 to change the first cartridge 90 and/or the second cartridge 100;

Rewind the first and/or the second piston rods 514, 516;

The first and/or second cartridge retainer doors will pop open;

The user removes the spent cartridge and replaces this spent cartridge with a new cartridge;

The reservoir doors may manually be closed;

Once the doors are closed, the first and second piston rods 514, 516 advance so that a most distal portion of each rod will meet the stopper of the respective cartridge and will stop advancing when a bung detect mechanism coupled to the micro-processor is activated;

The user replaces the dispense interface 200 in the one way manner on the cartridge holder 40;

The user can, optionally, connect a new double ended needle to the dispense interface 200;

The user can, optionally, perform a test shot or a priming step with the device 10; and The user can then set the next dose for a subsequent dose administration step.

One or more of the steps may be performed automatically, for example controlled by microcontroller 302, such as the step of rewinding the first and/or second piston rod.

In an alternative arrangement, the controller may be programmed so that the first and the second independent mechanical drivers 502, 506 may be operated to dispense either the first medicament 92 or the second medicament 102 prior to the other medicament. Thereafter, the second or the primary medicament may then be dispensed. In one preferred arrangement, the secondary medicament 102 is dispensed before the primary medicament 92.

Preferably, the first and second motors 530, 536 comprise electronic commutation. Such commutation may help to minimise the risk of a motor runaway condition. Such a motor runaway condition could occur with a system comprising a standard brushed motor experiencing a fault. In one embodiment of the motor drive system, a watchdog system may be provided. Such a system has the ability to remove power to either or both of the motors in the event of a software malfunction or a failure of the electronic hardware. To prevent the power from being removed, the correct input from a number of sections of the electronic hardware and/or the microcontroller software will need to be provided. In one of these input parameters is incorrect; power may be removed from the motor.

In addition, preferably both motors 530, 536 may be operated in a reverse direction. This feature may be required in order to allow the piston rods 514, 516 to be moved between a first and a second position.

Figure 24:
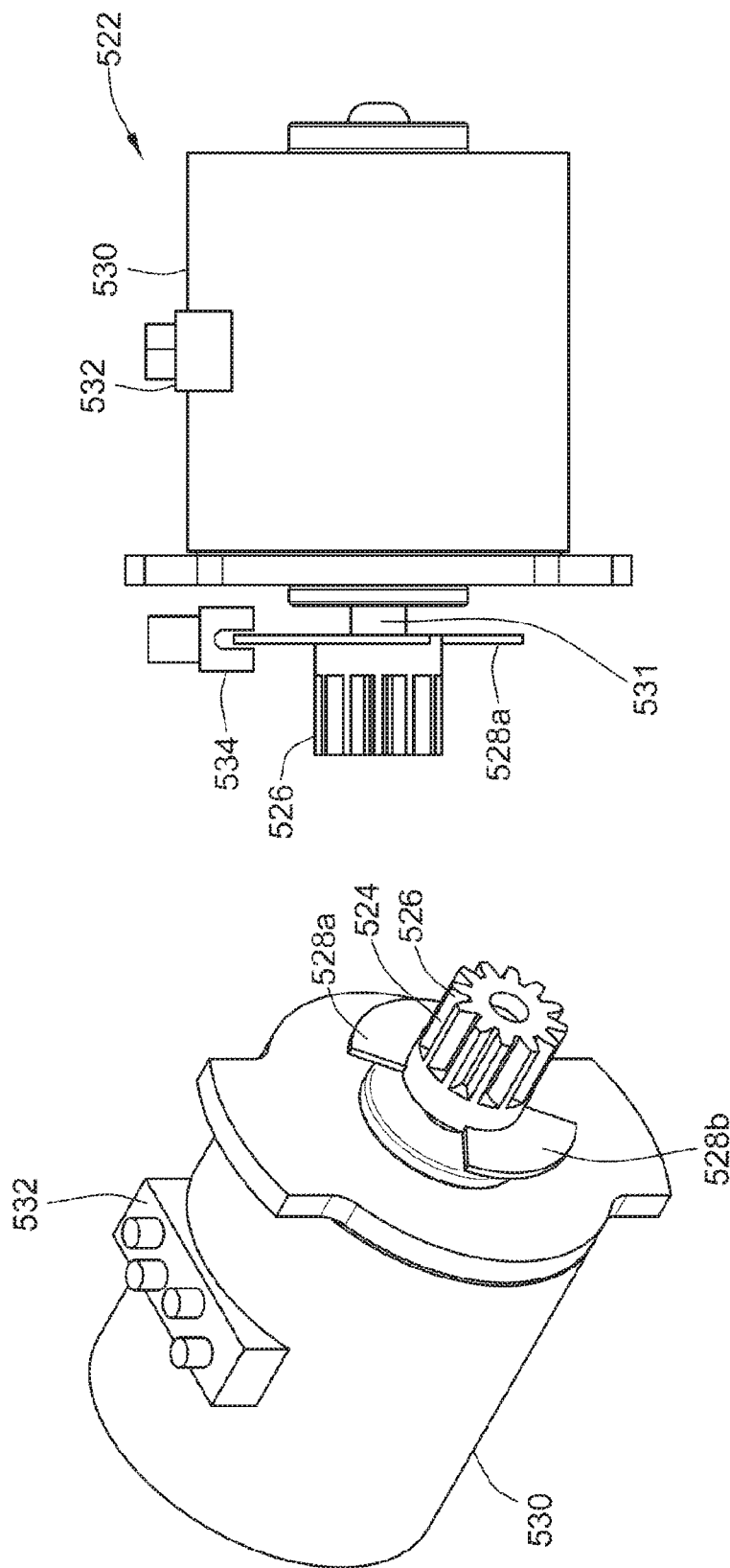
FIGS. 24a and 24b illustrate a motion detection system that may be used with the drive mechanism illustrated in FIG. 22.

Preferably, the first independent drive train 502 illustrated in FIG. 23 comprises a first motion detection system 522. FIG. 24a illustrates a perspective view of the first motor 530 illustrated in FIG. 23. FIG. 24b illustrates a preferred motion detection system 522 comprising the first motor 530 illustrated in FIG. 24a in conjunction with a digital encoder 534.

As illustrated in FIGS. 24a and 24b, such a motion detection system 522 may be beneficial as it can be utilized to provide operational and positional feedback from the first independent driver 502 to the control unit of the drug delivery device 10. For example, with respect to the first independent driver 502, a preferred motion detection system 522 may be achieved through the use of a first motor pinion 524. This first pinion 524 operatively coupled to an output shaft 531 of the first motor 530. The first pinion 524 comprises a rotating gearing portion 526 that drives a first gear of the first gearing arrangement 540 (see, e.g., FIG. 23). The first motor pinion 524 also comprises a plurality of flags 528a-b. In this first motion detection system 522, the first pinion 524 comprises a first flag 528a and a second flag 528b. These two flags 528a-b are positioned on the motor pinion 524 so that they pass through a first optical encoder 534 as the motor output shaft 531 and hence the connected first pinion 524 rotate when the motor is driven.

Preferably, as the first and second flags 528a-b pass through the first optical encoder 534, the encoder 534 can send certain electrical pulses to the microcontroller. Preferably, the optical encoder 534 sends two electrical pulses per motor output shaft revolution to the microcontroller. As such, the microcontroller can therefore monitor motor output shaft rotation. This may be advantageous to detect position errors or events that could occur during a dose administration step such as jamming of the drive train, incorrect mounting of a dispense interface or needle assembly, or where there is a blocked needle.

Preferably, the first pinion 524 comprises a plastic injection molded pinion. Such a plastic injection molded part may be attached to the output motor shaft 531. The optical encoder 534 may be located and attached to a gearbox housing. Such a housing may contain both the first gearing arrangement 540 along with the optical encoder 534. The encoder 534 is preferably in electrical communication with the control unit potentially via a flexible portion of the PCB. In a preferred arrangement, the second independent drive train 506 illustrated in FIGS. 22 and 23 comprises a second motion detection system 544 that operates in a similar fashion as the first motion detection system 522 of the first drive train 502.

Figure 25:
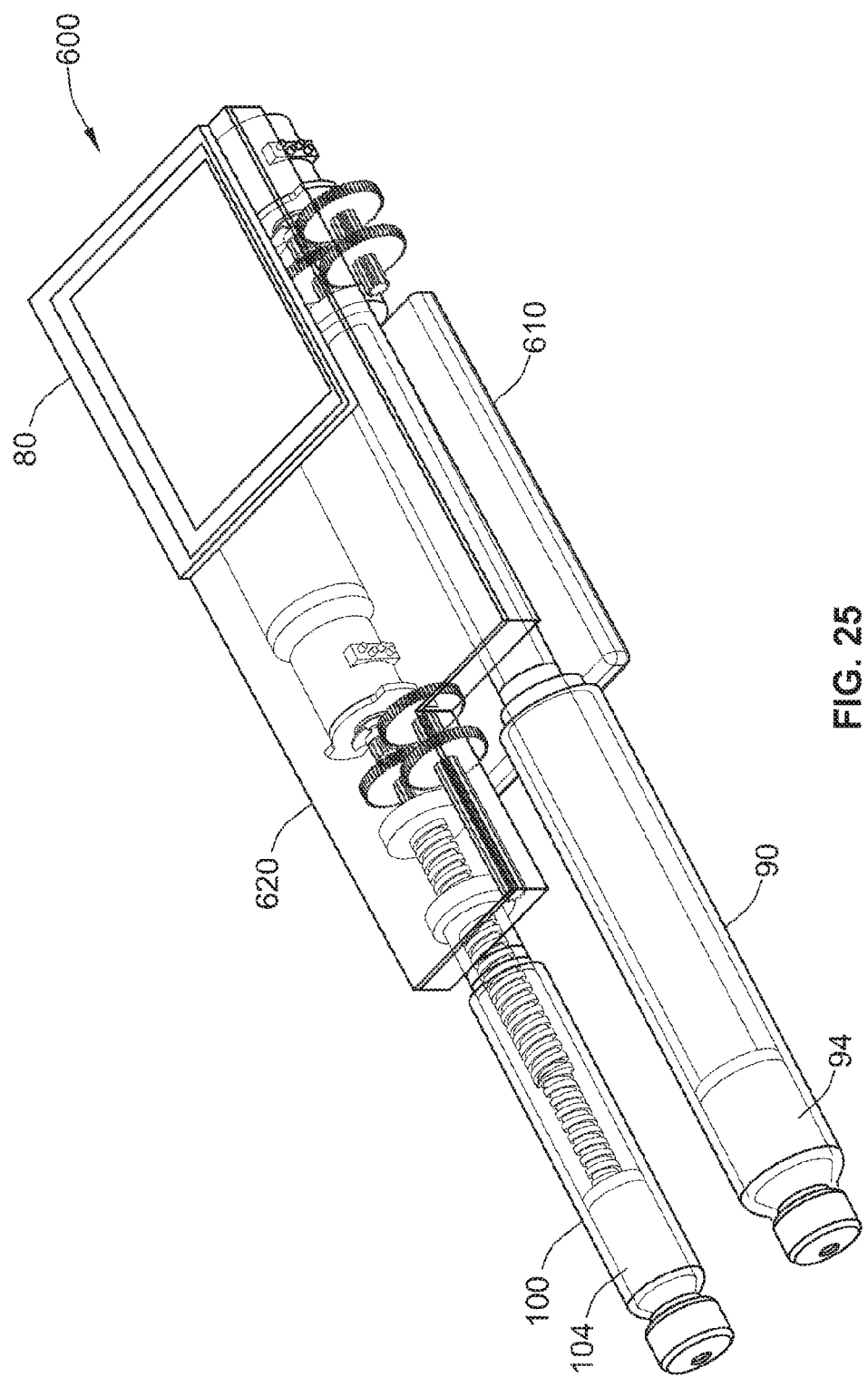
FIG. 25 illustrates a schematic view of an alternative drive mechanism for use with the drug delivery device illustrated in FIGS. 1a and 1b.

FIG. 25 illustrates various internal components of the drug delivery device 10 illustrated in FIGS. 1a and 1b including a preferred alternative drive train arrangement 600. As illustrated, FIG. 25 illustrates the digital display 80, a printed circuit board assembly (PCBA) 620, along with a power source or battery 610. The PCBA 620 may be positioned between the digital display 80 and a drive train 600 with the battery or power source 610 positioned beneath this drive train. The battery or power source 610 is electronically connected to provide power to the digital display 80, the PCBA 620 and the drive train 600. The digital display 80 and the PCBA 620 of this alternative drive train arrangement 600 operate in a similar manner as previously described.

As illustrated, both the first and second cartridges 90, 100 are shown in an expended state. That is, the first and second cartridges are illustrated in an empty state having a stopper at a most distal position. For example, the first cartridge 90 (which ordinarily contains the first medicament 92) is illustrated as having its stopper 94 at the end or most distal position. The stopper 104 of the second cartridge 100 (ordinarily containing the second medicament) is illustrated in a similar end position.

Figure 26:
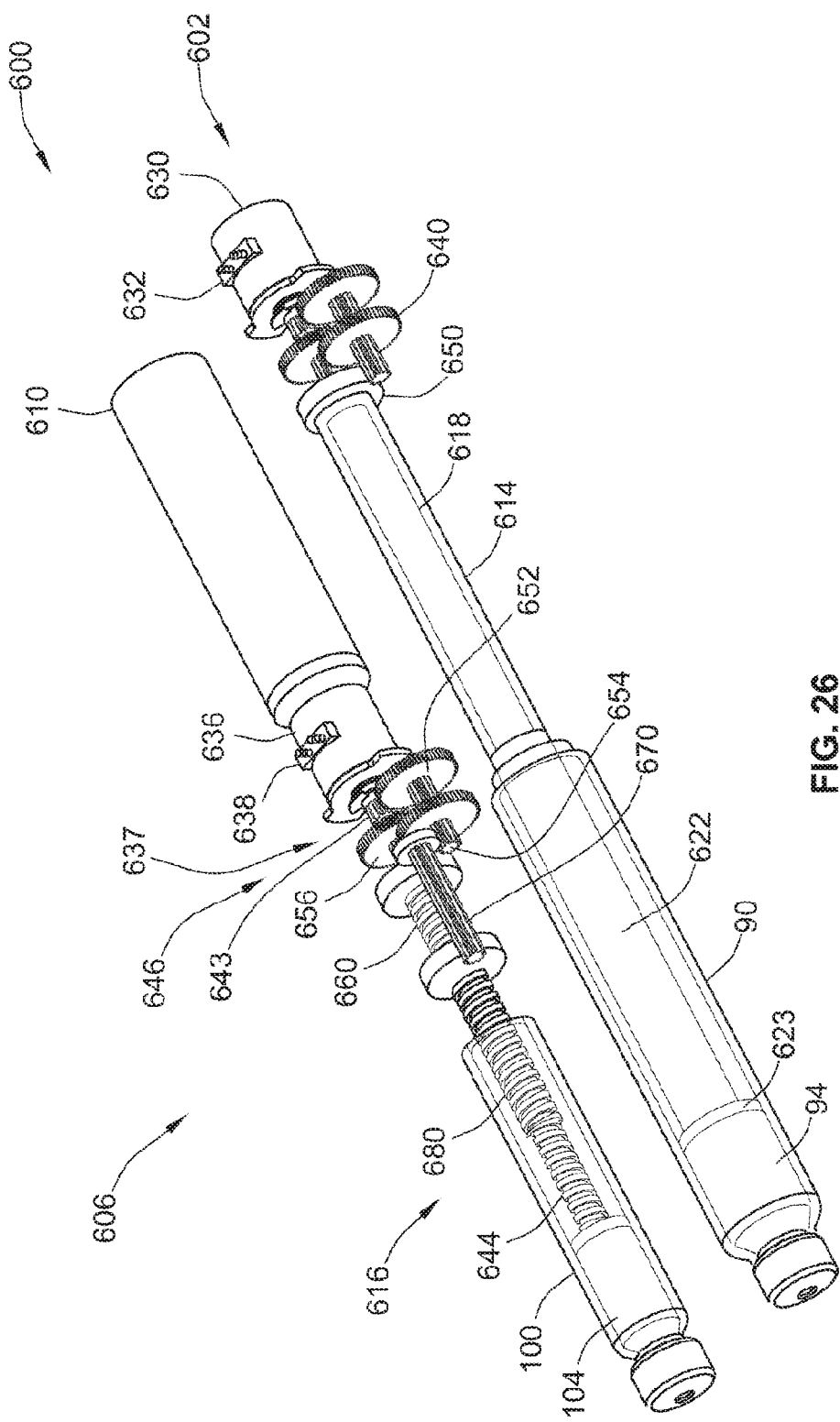
FIG. 26 illustrates a schematic view of the alternative drive mechanism illustrated in FIG. 25 with certain elements removed.

FIG. 26 illustrates the electro-mechanical system illustrated in FIG. 25 with both the digital display 80 and the PCBA 620 omitted. As illustrated, this alternative electro-mechanical system 600 operates to expel a dose from the first cartridge 90 containing a primary medicament 92 and the second cartridge 100 containing a secondary medicament 102. In this preferred electro-mechanical system 600, the system comprises an independent mechanical driver for both the first cartridge and the second cartridge. That is, an independent mechanical driver 602 operates to expel a dose from the first cartridge 90 and an independent mechanical driver 606 operates to expel a dose from the second cartridge 100. If this preferred electro-mechanical system 600 were to be reconfigured to operate on three different medicaments contained within three separate cartridges, three independent mechanical drivers could be provided so as to administer a combined dose. The independent mechanical drivers act under control of the motor drivers 332, 334 of the control unit 300 (see, e.g., FIG. 20).

The first independent mechanical driver 602 operates to expel a dose from the first cartridge 90 and operates in a similar manner as the independent drivers 502, 506 described with reference to the drive train 500 illustrated in FIGS. 22-23 above. That is, this first independent driver 602 comprises a first motor 630 that is operatively coupled to a first gearing arrangement 640. To energize this motor 630, a connector 632 is provided as a means of electrically connecting to the motor driver 332. This first gearing arrangement 640 is mechanically linked to a proximal portion of the telescoping piston rod 614. As this gearing arrangement 640 is driven by an output shaft of the first motor 632, this arrangement 640 rotates the proximal portion 618 of the telescoping piston rod 614. As this proximal portion 618 of the piston rod 614 is rotated, the second or distal portion 622 of the piston rod 614 is driven in a distal direction. Moving in this distal direction, a distal end 623 of the second portion 622 of the piston rod 614 exerts a force on the stopper 94 contained within the first cartridge 90. With a distal end 623 of the piston rod 614 exerting a force on the stopper 94, the user selected dose amount of the first medicament 92 is forced out of the cartridge 90 and into an attached dispense interface 200 and consequently out an attached needle assembly 400 as previously discussed.

Preferably, the first independent mechanical driver 602 comprises a bung or stopper detection system. Such a detection system may be used detect the position of the cartridge stopper 94 following a cartridge change event. For example, when a cartridge change event occurs, the piston rod is retracted in a proximal position so as to enable a user to open the cartridge retainer and thereby provide access to a spent cartridge. When the cartridge is replaced and the cartridge retainer door is shut, the piston rod will advance in a distal direction towards the stopper of new the cartridge.

In one preferred stopper detection system, a switch is provided at the distal end of the piston rod. Such a switch may comprise a mechanical, optical, capacitive, or inductive type switch. Such a switch would be in communication with the microcontroller and indicates when the piston rod is in contact with the stopper and hence may be used as a mechanism for stopping the drive system.

The second independent mechanical driver 606 operates to expel a dose from the second cartridge 100 in a different manner than the first independent driver 602. That is, this second mechanical driver 606 comprises a second motor 636 that is operatively coupled to a second gearing arrangement 646. To energize this motor 636, a connector 638 is provided as a means of electrically connecting to the motor driver 334.

This independent mechanical driver 606 comprises:
A motor 636;
A second gearing arrangement 646; and
A telescope piston rod 616.

The second gearing arrangement 646 is mechanically linked to a proximal portion of a nested piston rod 660. As this gearing arrangement 646 is driven by the output shaft of the second motor 636, this arrangement 646 rotates the proximal portion 660 of the telescoping piston rod 616.

The second gearing arrangement 646 comprises a motor pinion along with a plurality of compound gears (here four compound gears) along with a telescope input piston rod. Two of the compound gears are elongated to enable continuous mesh engagement with the input piston rod as the telescope extends in a distal direction to exert an axially pressure on the cartridge stopper 104 so as to expel a dose from the cartridge. The elongated gear may be referred to as a transfer shaft. The gearbox arrangement preferably has a ratio of 124:1. That is, for every revolution of the telescope input screw the output shaft of the second motor rotates 124 times. In the illustrated second gearing arrangement 646, this gearing arrangement 646 is created by way of five stages. As those skill in the art will recognize, alternative gearing arrangements may also be used.

The second gearing arrangement 646 comprises three compound reduction gears 652, 654, and 656. These three compound reduction gears may be mounted on two parallel stainless steel pins. The remaining stages may be mounted on molded plastic bearing features. A motor pinion 643 is provided on an output shaft of the second motor 636 and is retained on this shaft 637, preferably by way of an interference or friction fit connection.

As described above, the motor pinion 643 may be provided with two mounted "flag" features that interrupt the motion detect optical sensor. The flags are symmetrically spaced around the cylindrical axis of the pinion.

Figure 27:
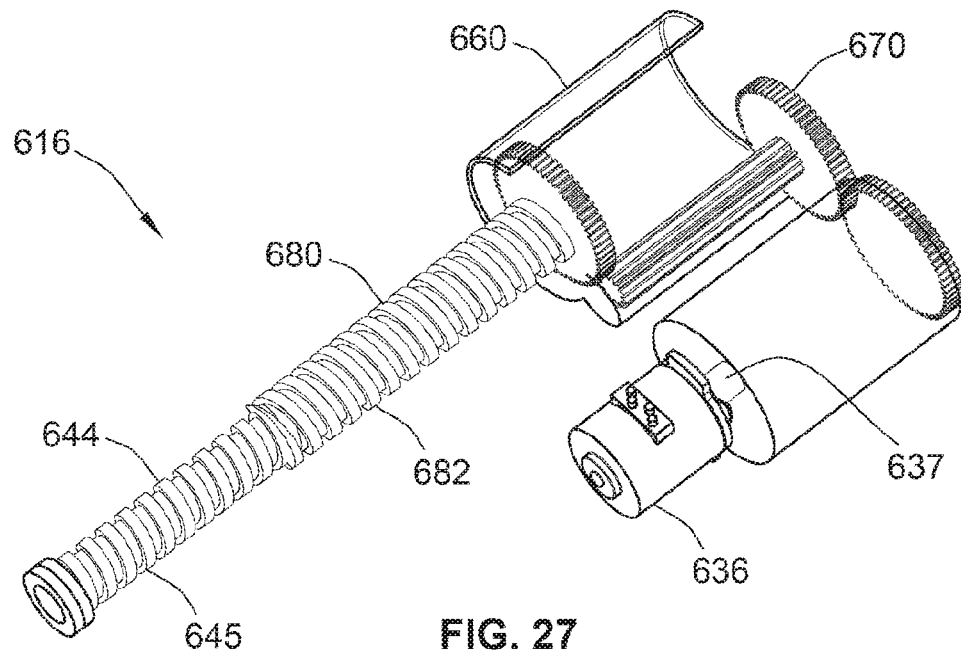
FIG. 27 illustrates a schematic view of a telescope piston rod and gearing arrangement illustrated in FIG. 26.
Figure 28:
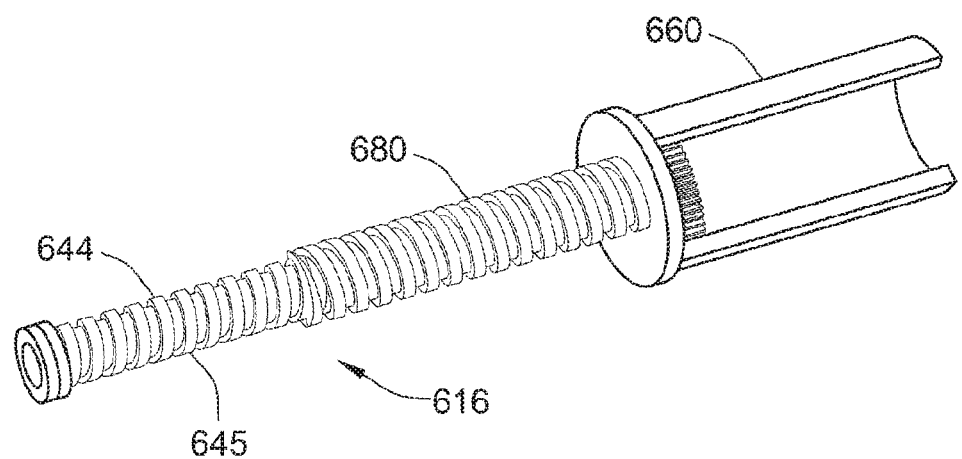
FIG. 28 illustrates a schematic view of a telescope piston rod arrangement illustrated in FIG. 27.
Figure 29:
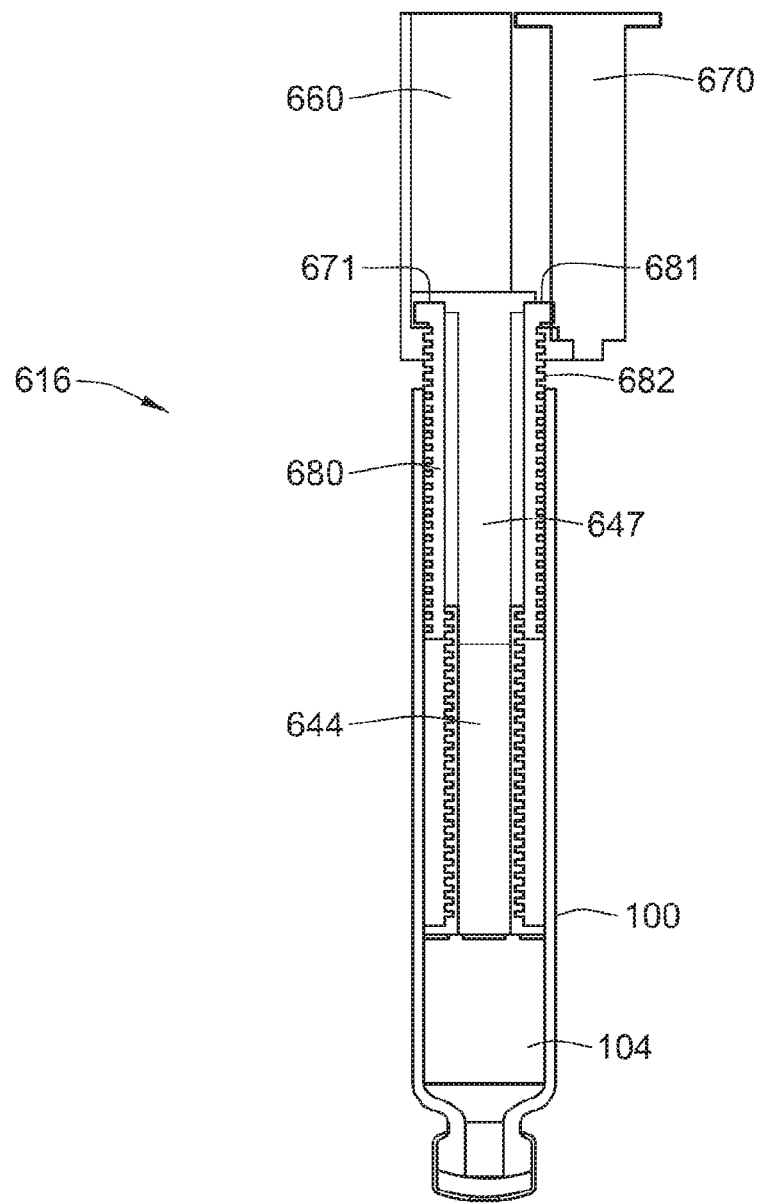
FIG. 29 illustrates a schematic view of one piston rod arrangement illustrated in FIG. 27.

The drive train telescoping piston rod 616 is illustrated in FIG. 27 and comprises a telescope plunger 644 that is operatively coupled to an input screw 680. FIG. 28 illustrates a perspective view of the telescope piston rod 616 coupled to a latch barrel. FIG. 29 illustrates a cross sectional view of the independent mechanical driver with the piston rod 616 in an extended position.

As illustrated, the outer elements (the telescope piston rod plunger 644 and telescope) create the telescopic piston rod 616 and react to the compressive axial forces that are developed. An inner element (telescope piston rod key 647 provides a means of reacting the rotational input force. This operates with a continuous motion and force since there will be no changes in drive sleeve diameter to generate varying levels of force.

The transfer shaft 670 is operatively linked to the gearing arrangement 646. The transfer shaft 670 can rotate but it cannot move in an axial direction. The transfer shaft 670 interfaces with the second gearing arrangement 646 and transfers the torque generated by the second gearbox arrangement 646 to the telescope piston rod 616.

Specifically, when the transfer shaft 670 is rotated by way of the gearing arrangement 646, the transfer shaft 670 will act on an integrated geared part 681 on a proximal end of the input screw 680. As such, rotation of the transfer shaft 670 causes the input screw 680 to rotate about its axis.

A proximal portion of the input screw 680 comprise a threaded section 682 and this threaded section is mated with a threaded section of the latch barrel 660. As such, when the input screw 680 rotates, it winds or screws itself in and out of the latch barrel 660. Consequently, as the input screw 680 moves in and out of the latch barrel, the screw 680 is allowed to slide along the transfer shaft 670 so that the transfer shaft and the gears remain mated.

The telescope plunger 644 is provided with a threaded section 645. This threaded section 645 is threaded into short section in distal end of the input screw 680. As the plunger 644 is constrained from rotating, it will wind itself in and out along the input screw 680.

A key 647 is provided to prevent the plunger 644 from rotating. This key 647 may be provided internal to the input screw 680 of the piston rod 616. During an injection step, this key 647 moves in the axial direction towards the stopper 104 of the cartridge 100 but does not rotate. The key 647 is provided with a proximal radial peg that runs in a longitudinal slot in the latch barrel 660. Therefore, the key 647 is not able to rotate. The key may also be provided with a distal radial peg that engage a slot in the plunger 644.

Preferably, the drug delivery device 10 comprises memory devices comprising enough memory storage capability so as to store a plurality of algorithms that are used to define a plurality of different therapeutic profiles. In one preferred arrangement, after a user sets a dose of the primary medicament, the drug delivery device will be preprogrammed so as to determine or calculate a dose of the secondary medicament and perhaps a third medicament based on one of the stored therapeutic profiles. In one arrangement, the healthcare provider or physician selects a therapeutic dose profile and this profile may not be user alterable and/or may be password protected. That is, only a password known by the user, for example a healthcare provider or physician, will be able to select an alternative profile. Alternatively, in one drug delivery device arrangement, the dose profile is user selectable. Essentially, the selection of the therapeutic dose profiles can be dependent upon the individualized targeted therapy of the patient.

Figure 30:
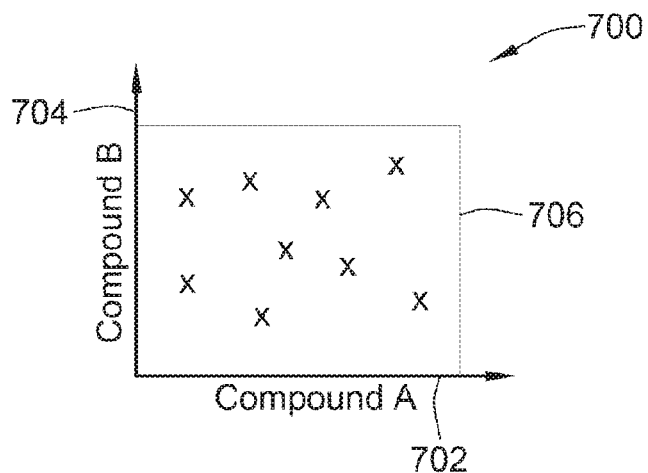
FIG. 30 illustrates a potential deliverable therapy of a known two input and two compound combination device.

As described above, certain known multi drug compound devices allow independent setting of the individual drug compounds. As such, the delivery of the combined dose in a combination is determined by a user. This is not ideal in all the therapeutic situations that a patient may face. For example, FIG. 30 illustrates a potential deliverable therapy 700 of such a known two input and two compound combination device: that is, a device that requires a user to physically set the first dose of a first medicament and then physically set the second dose of the second medicament. In such a known device, a user could select a dose of the Compound A or the primary medicament 702 along the x-axis (i.e., between O units to a top dose). Similarly, the user could then select a dose of the secondary medicament—Compound B 704 along the y-axis (i.e., between O units to a top dose). As such, although these known devices can potentially deliver the combination of the two compounds as illustrated by area 706 shown in FIG. 30, there is an inherent risk that the user does not follow the correct, prescribed therapeutic profile, either intentionally or otherwise. For example, in such a device, the user must know, or be able to determine or calculate, the required relationship and then set the dose of both the first and second compounds 702, 704 independently.

One of the primary reasons for combining drug compounds is that generally all the pharmaceutical elements are required to ensure an increased therapeutic benefit to a patient. In addition, some compounds and some combinations of compounds need to be delivered in a specific relationship with each other in order to provide the optimum pharmacokinetic ("PK") and pharmacodynamic ("PD") response. Such complex relationships between one, two, or more (i.e., more than a plurality) of medicaments may not be achievable through a single formulation route and could potentially be too complex for the user to understand, or follow correctly, in all cases.

Figure 31A:
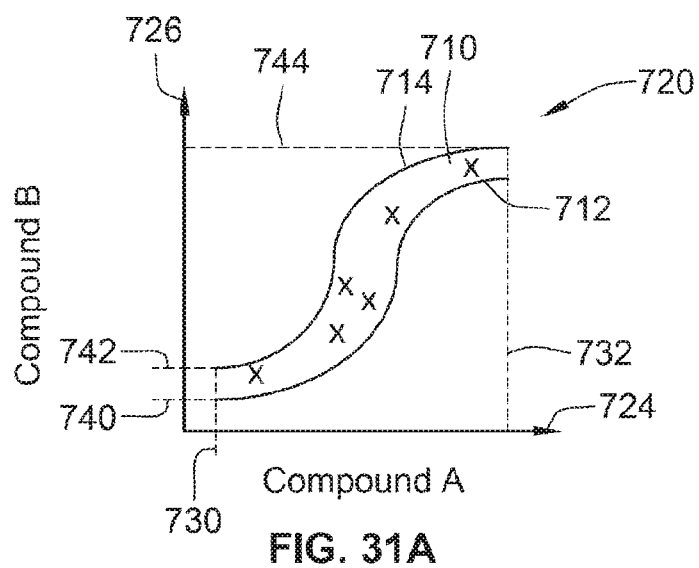
FIGS. 31a and 31b illustrates a first arrangement of a predefined therapeutic profile that may be programmed into the programmable drug delivery device.
Figure 31B:
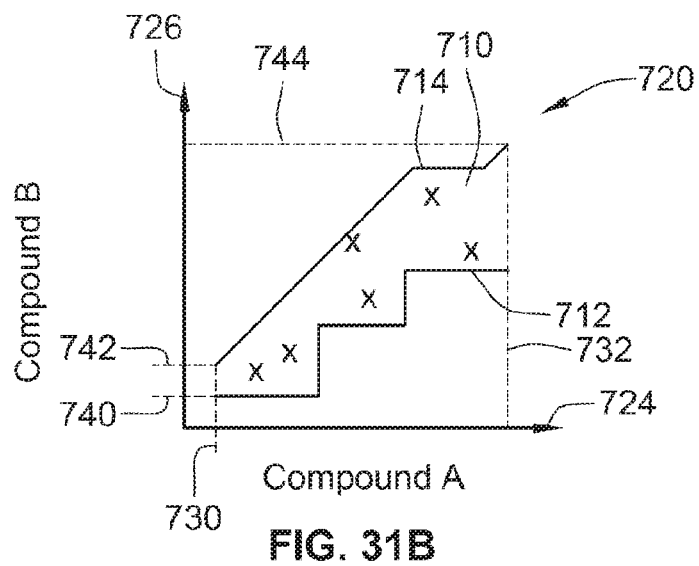

In an example embodiment of the invention, a multi drug compound device may be reliant upon the user input for each independent compound to control the delivered dose profile within predetermined thresholds. For example, FIGS. 31a and 31b illustrate in diagrammatic form a potential delivered therapy 720 of a theoretical two input, two compound combination device. The area 710 illustrates the range of potential combination doses that are achievable. That is, a user can set the dose of the primary medicament or Compound A 724 anywhere from a minimum value 730 to a maximum value 732. Similarly, the user can separately and independently set the dose of the secondary medicament or Compound B 726 anywhere from a minimum value 740 to an overall maximum value 744 within predetermined thresholds, for example between a lower limit 712 and an upper limit 714. In this area 710, the plurality of 'X' designations illustrate specific combination doses that a patient and/or user of such a device may elect to set and deliver. Essentially, the combined dose of Compound A 724 and Compound B 726 can be set anywhere within this area 710. In the example embodiment, the user is limited to setting a combined dose only along a predefined profile, such as the predefined profile illustrated by area 710 in FIGS. 31a and 31b. For example, if an amount of Compound A is selected by a user to be the minimum value 730, Compound B may be selected between the minimum value 740 and a maximum value 742 defined for this minimum value of Compound A.

The lower limit 712 and the upper limit 714 may be represented by a curve as in FIG. 31a. In an alternative embodiment, the lower limit and the upper limit may be represented by one or more lines, by a stepwise function, and/or the like. For example, in the diagram of FIG. 31b, the upper limit 714 is represented by a diagonal line and a horizontal line, the lower limit 712 is represented by a stepwise function of 3 steps. The upper limit 714 and the lower limit 712 define an area 710, in which a user may select a combination of Compound A and Compound B, for example one of the combinations designated by the 'X'-marks.

In further example embodiments, the presently proposed programmable electro-mechanical drug delivery device described in detail above uses only a single input in order to offer an innovative solution to these and other related problems. In further embodiments, the proposed programmable multi-drug compound device uses only a single dispense interface. As just one example, such a device is capable of delivering any of a plurality of predefined programmed therapeutic profiles for various drug combinations. As an alternative, such a device is capable of delivering only one predefined programmed therapeutic profile for various drug combinations.

By defining the ratio-metric relationship or relationships between the various individual drug compounds (2, 3, or more), the proposed device helps to ensure that a patient and/or user receives the optimum therapeutic combination dose from a multi drug compound device. This can be accomplished without the inherent risks associated with multiple inputs. This can be achieved since the patient and/or user is no longer called upon to set a first dose of medicament and then determine or calculate and then independently set a correct dose of a second and/or third medicament in order to arrive at the correct dose combination each time the device is used to administer a combination dose.

Figure 32:
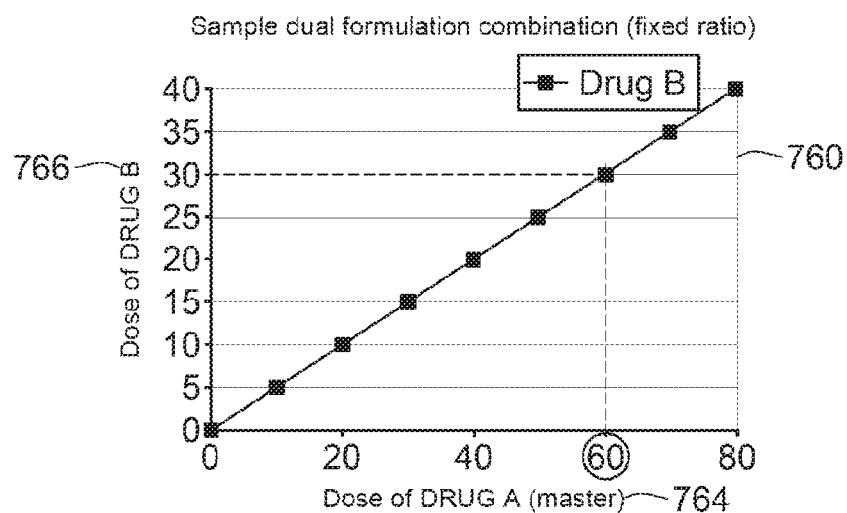
FIG. 32 illustrates one arrangement of a predefined fixed ratio therapeutic profile that may be programmed into the drug delivery device.

As just one example, FIG. 32 illustrates a first arrangement of a predefined therapeutic profile 760 that may be programmed into the programmable drug delivery device. In FIG. 32, a first therapeutic dose line represents an example of a predefined therapeutic profile 760 compared to the area 706 indicating all potential drug combinations that can be selected by way of currently known devices as illustrated in FIG. 30. As can be seen from this predefined profile 760 illustrated in FIG. 32, for every dose value of Compound A 764 (also herein referred to as the Master Drug or the Primary Drug or the Primary Medicament) selected by the user, the drug delivery device 10 will rely on a previously stored therapeutic profile to calculate the dose value of Compound B 766 along this therapeutic profile 760.

As such, the user merely needs to select a first dose of the first drug: Drug A or the primary medicament and the drug delivery device 10 automatically calculates the dose of the secondary medicament or Drug B based on this preselected dosing profile 760. For example, if the user selects a dose comprising "60 Units" for Compound A 764, the drug delivery device 10 will recall the selected dosing profile 760 from its memory device and then automatically calculate the dose value of "30 Units" for Compound B 766.

In an alternative drug delivery device arrangement, and as discussed in greater detail above, the drug delivery device may comprise a coding system. A coding system may be provided if coding means is provided on either the first or the second cartridge so that the drug delivery device could then identify the particular medicament contained within an inserted cartridge. After the drug delivery device undergoes a method or process for determining cartridge and/or medicament identification, the drug delivery device could then potentially automatically update the therapeutic profile or profiles. For example, a new or a revised/updated profile may be selected if required to reflect an updated or revised pharmaceutical philosophy so as to achieve an optimum medicament relationship. Alternatively, a new or a revised/updated profile may be selected if a health care provider has decided to alter a patient's therapy strategy. An updated or revised profile may be loaded into the device through a wired or wireless connection, for example from a memory comprised in the cartridge, from an external device, from the internet and/or the like. The updated or revised profile may be loaded automatically, for example after insertion of the cartridge, or only after user confirmation, for example after a user presses a button on the device to confirm a message shown in the display.

As another example of a therapeutic profile, the proposed drug delivery device 10 may be programmed to calculate a linear ratio profile for the delivered dose from the drug delivery device 10 that comprises two or more discrete medicament reservoirs.

For example, with such a programmed therapeutic profile, the constituent components of the dose would be delivered to a patient in a fixed, linear ratio. That is, increasing the dose of one element will increase the dose of the other constituent element(s) by an equal percentage. Similarly, reducing the dose of one element will reduce the dose of the other constituent element(s) by an equal percentage.

FIG. 32 illustrates one arrangement of a predefined ratio therapeutic profile 760 that may be programmed into the drug delivery device 10. In the profile illustrated in FIG. 32, the user would select a dose of Drug A 764. As previously described above, the user could be called upon to select this first dose by toggling or manipulating one of the buttons provided on the operator interface of the drug delivery device 10. Once this initial dose of the primary Drug A 764 is selected by the user and then set by the drug delivery device, the control unit of the device 10 calculates and then sets the resultant dose of Drug B 766 based on the therapeutic profile 760. For example, referring to FIG. 32, if the user selects a dose of 60 units for Drug A 764, the control unit would recall the algorithm for this particular therapeutic profile 760 and would then use this algorithm to calculate the dose of Drug B or the secondary medicament 766. According to this profile 760, the control unit would calculate a 30 Units dose of Drug B or the secondary medicament. In an alternative embodiment, the profile is stored as a look-up table in a memory.

For every value of drug A, a corresponding value of drug B is stored in the look-up table. In a further embodiment only some values of drug A are stored in the look-up table along with corresponding values of drug B. Missing values are then calculated by interpolation, for example by linear interpolation.

Therefore, when the device is then used to dispense the combination of medicaments, this combined dose comprising 60 Units of Drug A and 30 Units of Drug B would be administered. As those of skill in the art will recognize, the ratio of the two (or more) medications can be tailored according to the needs of the patient or therapy by a number of methods including changing the concentration of the medicaments contained within the primary or secondary reservoirs.

As just one example, the drug delivery device 10 may comprise three or more medicaments. For example, the device 10 may contain a first cartridge containing a long acting insulin, a second cartridge containing a short acting insulin, and a third cartridge containing a GLP-1. In such an arrangement, referring back to FIGS. 6 and 9, the cartridge holder 40 of the drug delivery device 10 would be re-configured with three cartridge retainers (rather than the two retainers 50, 52 illustrated in FIGS. 6 and 9) and these three cartridge retainers would be used to house three compound or medicament cartridges.

Figure 33:
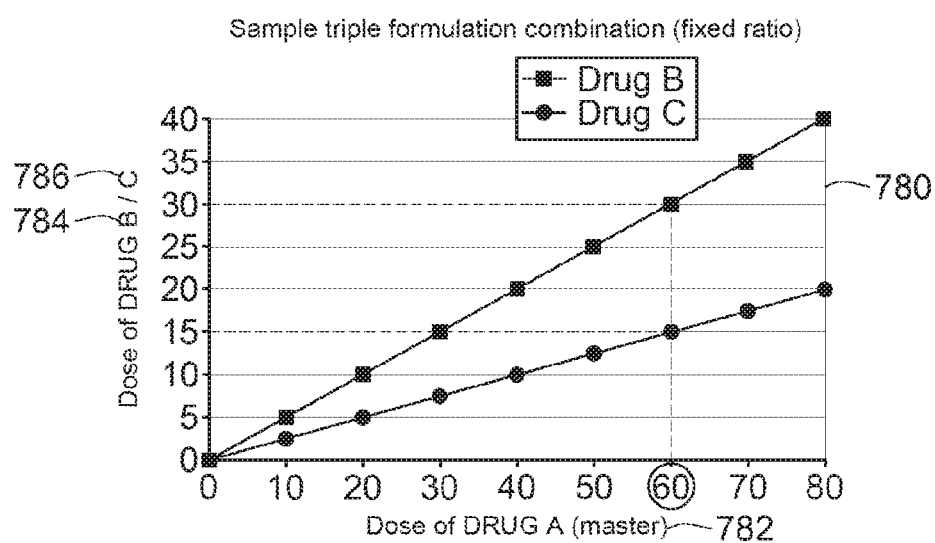
FIG. 33 illustrates an alternative arrangement of a predefined fixed ratio therapeutic profile that may be programmed into a drug delivery device comprising three medicaments.

As just one example, FIG. 33 illustrates an alternative arrangement of a predefined fixed ratio therapeutic profile 780 that may be programmed into the proposed drug delivery device 10. FIG. 33 illustrates a linear dose profile 780 that may be used with a drug delivery device comprising three medicaments. For example, in this profile, the user would first select a dose of 60 Units of the primary medicament Drug A 782. Once this initial dose of Drug A 782 has been selected, the control unit of the device 10 would calculate, based on this selected therapeutic profile 780, the resultant dose amount of Drug B (the secondary medicament) 784 as well as the resultant dose of Drug C (the tertiary medicament) 786. When the device 10 is then used to dispense the combined dose of medicaments, the combination dose of 105 Units would comprise a combination dose of 60 Units of Drug A, a calculated dose of 30 Units of Drug B 784, and a calculated dose 15 Units of Drug C 786. In such an arrangement, the primary or master drug 782 could comprise an insulin or insulin analog, the secondary medicament 784 could comprise a GLP-1 or GLP-1 analog, and the tertiary medicament 786 could comprise a local anesthetic or anti-inflammatory.

Figure 34:
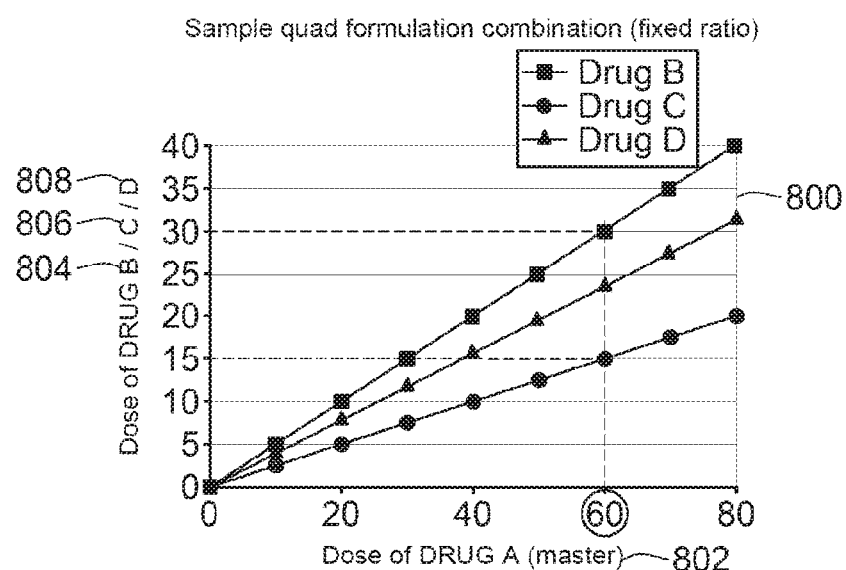
FIG. 34 illustrates an alternative arrangement of a predefined fixed ratio therapeutic profile that may be programmed into a drug delivery device comprising four medicaments.

Similarly, FIG. 34 illustrates an alternative arrangement of a predefined fixed ratio therapeutic profile 800 that may be programmed into the drug delivery device 10 illustrated in FIG. 1. FIG. 34 illustrates a linear profile for use with a drug delivery device comprising four different medicaments: Drug A 802, Drug B 804, Drug C 806, and Drug D 808. Again, in this situation, once the initial dose of the primary medicament (i.e., Drug A) 802 has been selected by the user, the control unit of the device 10 calculates, based on this linear profile 800, the resultant dose amount of Drug B 804, Drug C 806, and Drug D 808. For example, in this illustrated exemplary profile, a user has selected a 60 Unit dose of Drug A or the primary medicament 802. With such a selected primary dose, when the device 10 is then used to dispense the calculated combined dose, the combination dose of 129 Units would comprise 60 Units of the selected Drug A 802, 30 Units of Drug B 804, 24 Units of Drug D 806, and 15 Units of Drug C 808.

A derivative therapeutic profile of the various profiles illustrated in FIGS. 32-34 may be provided for the combination of compounds to be delivered in a fixed ratio, but for the dose setting process for the master drug compound (i.e., Drug A) to only allow doses of the secondary compound or medicament to be calculated in discrete amounts. This would mean that the dose of the dependent drug compound or compounds (e.g., Drug B, Drug C, etc.) or the secondary medicaments would also only be calculated in discrete amounts.

Figure 35:
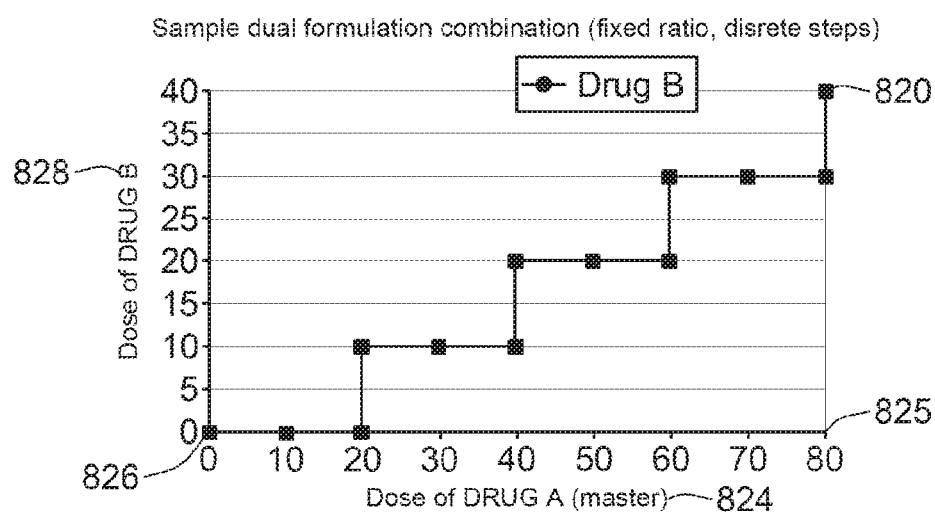
FIG. 35 illustrates another alternative arrangement of a predefined fixed ratio therapeutic profile having discrete dose steps and that may be programmed into the drug delivery device.

For example, FIG. 35 illustrates an alternative arrangement of a predefined fixed ratio therapeutic profile 820 having discrete dose steps and that may be programmed into the drug delivery device 10. For example, this profile 820 comprises a fixed ratio profile having five (5) discrete dose steps of Drug B 828 for varying amounts of Drug A 824. While following the fixed ratio profile, Drug A 824 would be continuously variable between a maximum dose 825 and a minimum dose 826 while the calculated dose of the secondary medicament 828 would not be continuously variable. For example, if a user were to select a dose of either 0 or 20 Units of the master medicament Drug A 824, the drug delivery device 10 would determine a zero ("0") dose of Drug B 828. Similarly, if a user were to select a dose of anywhere from 20-40 Units of the Drug A 824, the drug delivery device 10 would compute a dose of 10 Units of Drug B 828. Therefore, in this later case, a combination dose of 20 Units of Drug A 824 would result in a maximum dose of 10 Units of Drug B 828.

The proposed linear ratio profile discussed and described with respect to FIGS. 32-34 provides a number of advantages. For example, these various proposed linear ratio profiles are analogous to a profile of a single formulation product that contains a combination of two or more therapeutic medicaments, where the concentration of the formulation is constant. This means that with the proposed drug device 10 programmed with such linear ratio profiles 760, 780 and 800, this would provide an alternative delivery platform for scenarios where it is not possible to formulate the individual elements together into a single formulation. This may be the case where mixing such medicaments may raise stability, compromised performance, toxicology issues and/or other related types of issues.

In addition, the proposed linear ratio therapy profiles 760, 780 and 800 are robust to a split dosing requirement. That is, the desired dose can potentially be split into multiple, smaller injections without compromising the total amount of each constituent medicament that is ultimately administered. As just one example, returning to FIG. 32, if the patient were to split up a 60 Unit dose into a 30 Unit dose followed by two 15 Unit doses, the net result (in terms of the total amount of each of the constituent elements delivered) would be the same. Such a split dosing requirement might be advantageous in situations where the calculated combined dose is a large dose (e.g., where the injected dose is greater than 1 ml), where the delivery of such volumes to a single injection site might be painful for a particular patient or sub-optimal in terms of its absorption profile.

In addition, cognitively, the relationship between the various compounds or drugs is reasonably straightforward for a patient to understand. Moreover, with such profiles 760, 780 and 800, the patient and/or health care provider is not called upon to perform profile calculations themselves since it is the microcontroller of the device 10 that computes the value of the secondary medicament automatically once the initial dose of the primary medicament has been set. In contrast to the linear profiles 760, 780 and 800 shown in FIGS. 32-34, FIGS. 35-50 show non-linear profiles showing a relation between the primary medicament and at least the secondary medicament or fluid agent.

Figure 36:
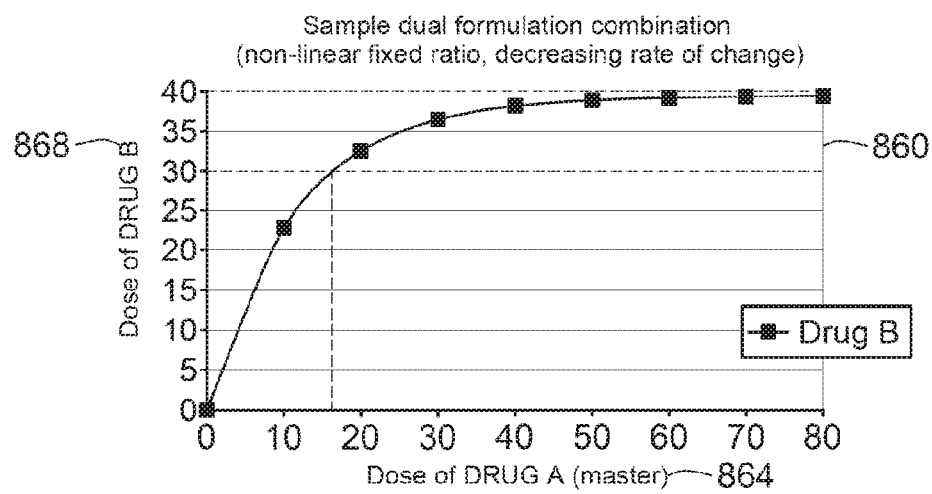
FIG. 36 illustrates an arrangement of a predefined non-linear fixed ratio therapeutic profile having a decreasing rate of change and that may be programmed into the drug delivery device.

FIG. 36 illustrates another proposed therapy profile 860 that might be programmed into the control unit of the drug delivery device 10. This profile 860 comprises a non-linear ratio dose profile. With such a programmed profile, the constituent components of the dose would be delivered to a patient in a fixed, non-linear ratio. That is, the relationship between the size of the delivered dose of the primary medicament and that of the secondary medicament and perhaps a third medicament is fixed, but is non-linear in nature. With such profiles, the relationship between the primary and the secondary medicament might be cubic, quadratic, or other similar type of relationship.

As described above, the delivery of a combination of drug products (i.e., single doses that are made up from the combination of two or more individual drug formulations) in a format where the ratio-metric profile is predefined, offers a number of benefits for both a patient and the treatment of a particular condition. For certain combinations, the ideal profile might be for the various individual formulations to be delivered in a defined, non-linear ratio to one another. Therapeutic profiles of this type are not achievable from a combination drug or drugs that is co-formulated into a single drug reservoir, such as, but not limited to, a standard 3 ml glass cartridge. In such situations, the concentration of the various constituent parts within the glass cartridge is constant (i.e., xmg/ml), and would be particularly difficult for a patient to calculate on certain known devices for each dose. To calculate or determine such concentration would be reliant on the patient or health care provider being able to look up the correct dose on a table (or similar lookup document or prescription) and this may be less desirable as such a method would be more prone to error.

FIGS. 36-39 illustrate exemplary profiles 860, 880, 900 and 920 utilizing non-linear dose profiles. For example, FIG. 36 illustrates an arrangement of a predefined non-linear fixed ratio therapeutic profile 860 having a decreasing rate of change. That is, as the amount of the primary medicament Drug A 864 increases, the amount of the secondary medicament Drug B 868 increases sharply, as, for example, the amount of Drug A increases from 0 Units to approximately 30 Units and quickly tapers off thereafter. As such, FIG. 36 illustrates a sample dual formulation wherein the profile 860 is non-linear.

Figure 37:
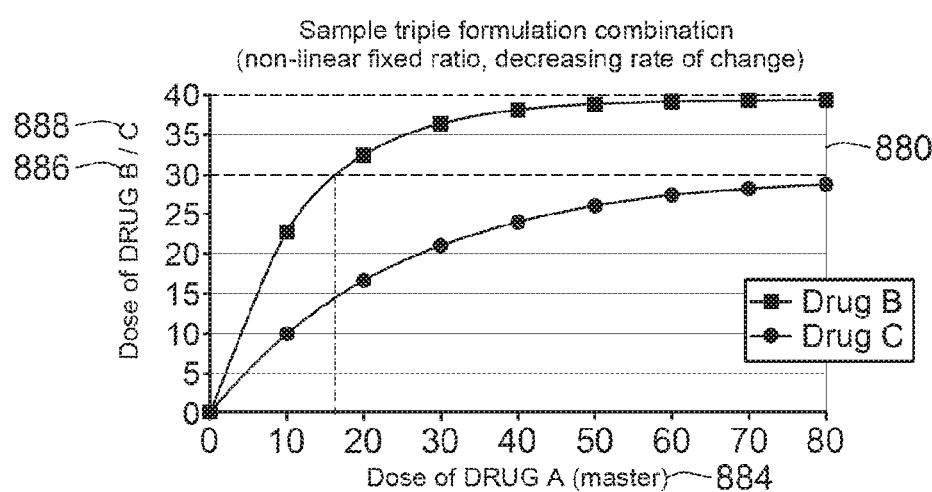
FIG. 37 illustrates an alternative arrangement of a predefined non-linear fixed ratio therapeutic profile having a decreasing rate of change and that may be programmed into the drug delivery device.

FIG. 37 illustrates a similar profile 880 but a profile that represents a sample triple formulation combination of three different medicaments: Drug A 884, Drug B 886 and Drug C 888. As just one example, with this profile 880, if the user sets a dose of 50 Units of the master Drug A 884, the control unit of the device 10 will compute a resulting combined dose comprising approximately a 37 Unit dose of Drug B 886 and an approximately 26 Unit dose of Drug C 888.

Some of the advantages of using such a fixed, non-linear ratio of the constituent drug elements as illustrated include (but are not limited to) the fact that such profiles utilize a decreasing rate of change profile. These types of illustrated therapy profiles 860, 880 may be appropriate in situations where it is desirable to initially rapidly increase the dose of Compound B or the secondary medicament, relative to Compound A. However, once the desirable dose range has been reached to slow this rate of increase so that the dose does not then increase much further, even if the dose of Compound A doubles, for example. A profile of this type might be beneficial in therapeutic applications where there are a potentially wide range of doses of Compound A that patients might require (either as an individual, or across the therapy area as a whole), but where there is a much narrower therapeutically beneficial range of doses for Compound B.

The dose profiles 860, 880 illustrated in FIGS. 36 and 37 provide a non-linear fixed ratio having a decreasing rate of change. Alternatively, a proposed non-linear fixed ratio dose profile may comprise a profile having an increasing rate of change. For example, one such profile 900 having such a non-linear increasing rate of change within a two medicament drug delivery device such as device 10 is illustrated in FIG. 38.

Figure 39:
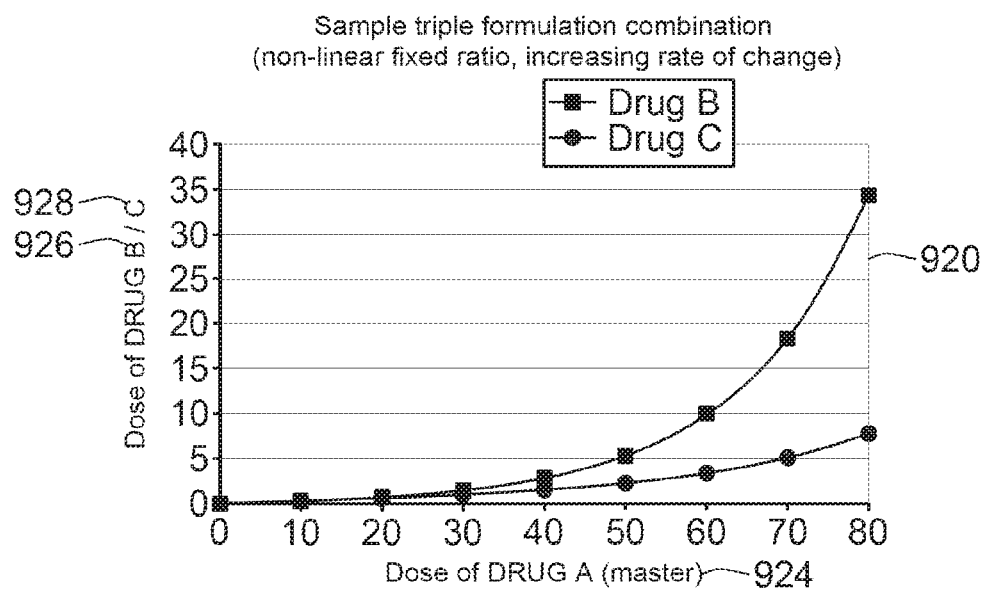
FIG. 39 illustrates an alternative arrangement of a predefined non-linear fixed ratio therapeutic profile having an increasing rate of change and that may be programmed into the drug delivery device.

FIG. 39 illustrates a non-linear fixed ratio profile 920 having such an increasing rate of change within a three medicament drug delivery device. With this profile 920, as the size of the user selected dose of Drug A 924, the incremental increase in the computed dose of Drug B 926 and Drug C 928 increases.

Figure 38:
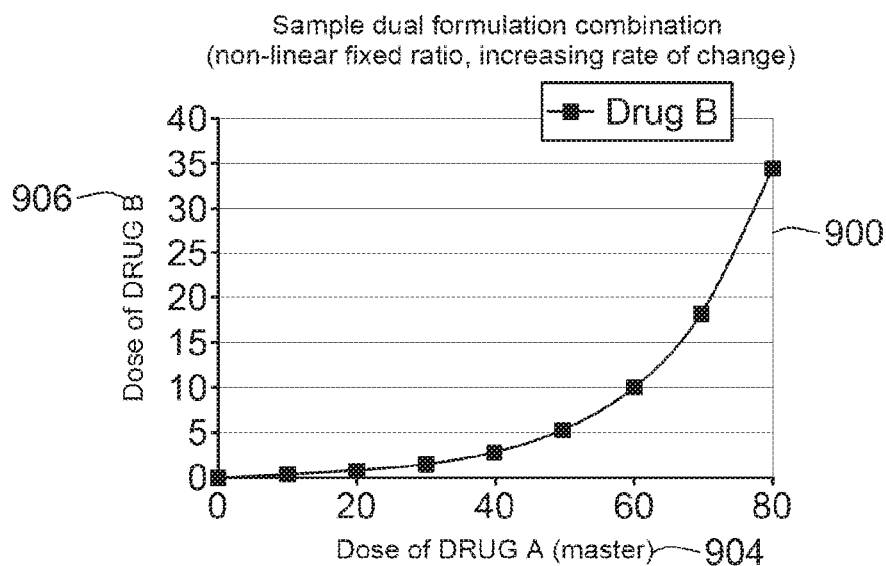
FIG. 38 illustrates an arrangement of a predefined non-linear fixed ratio therapeutic profile having an increasing rate of change and that may be programmed into the drug delivery device.

The therapeutic profiles 900 and 920 illustrated in FIGS. 38 and 39 might be advantageous in situations where a patient receiving a low dose of Compound A (e.g., 0-40 Units of Drug A 904) may only require a relatively low dose of Compound B 906 for the desired pharmokenitic therapeutic response. However, as the size of the dose of Compound A 904 increases, the dose of Compound B 906 needs to provide the same therapeutic response increase at a much greater rate.

Alternatively, the drug delivery device 10 may be programmed with an algorithm for computing a dose of the secondary medicament based on a fixed, linear ratio followed by a fixed dose profile. As just one example, such a stored profile may initially follow a fixed ratio profile for certain low doses of the primary medicament or Compound A. Then, above a certain threshold dose level of the Drug A, the profile switches to a fixed dose of the secondary medicament or Compound B. That is, for higher doses of the primary medicament/Compound A, the secondary medicament will comprise essentially a fixed dose.

For certain therapies, the delivery of combination drug products (i.e., single doses that are made up from the combination of two or more individual drug formulations) might be beneficial for the dose of the secondary medicament to initially rise rapidly relative to the primary medicament. Then, once a pre-determined threshold value of the primary medicament has been reached, the profile will then flatten out. That is, the calculated dose of the secondary medicament will remain constant regardless of further increases in the set dose of the primary medicament. Such fixed ratio followed by fixed dose—low dose threshold therapeutic profiles are not achievable from a combination drug that is co-formulated into a single primary pack (such as, but not limited to, a standard 3 ml glass cartridge) where the concentration of the various constituent parts is constant (xmg/ml). Achieving such profiles would also be particularly difficult for a patient to calculate on current devices for every dose.

Figure 40:
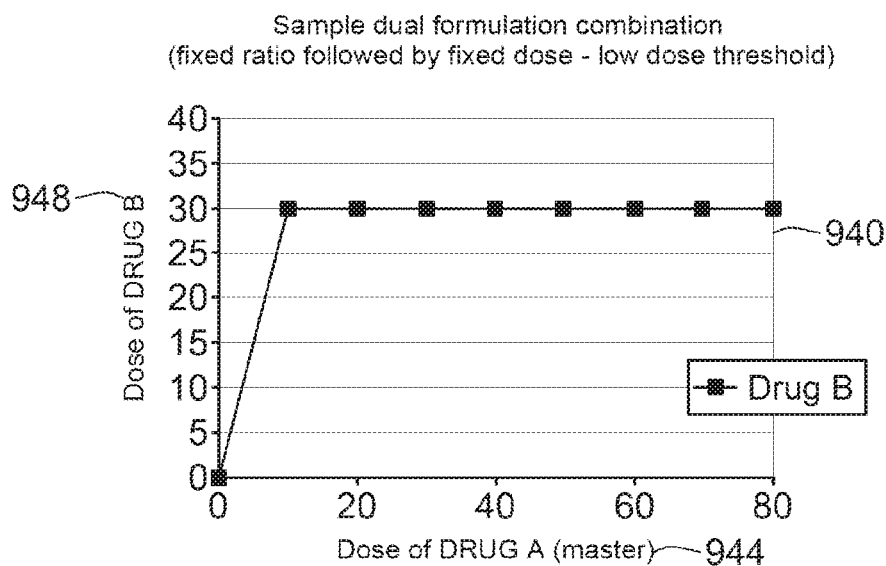
FIG. 40 illustrates an arrangement of a predefined fixed ratio—fixed dose therapeutic profile having a low dose threshold and that may be programmed into the drug delivery device.
Figure 41:
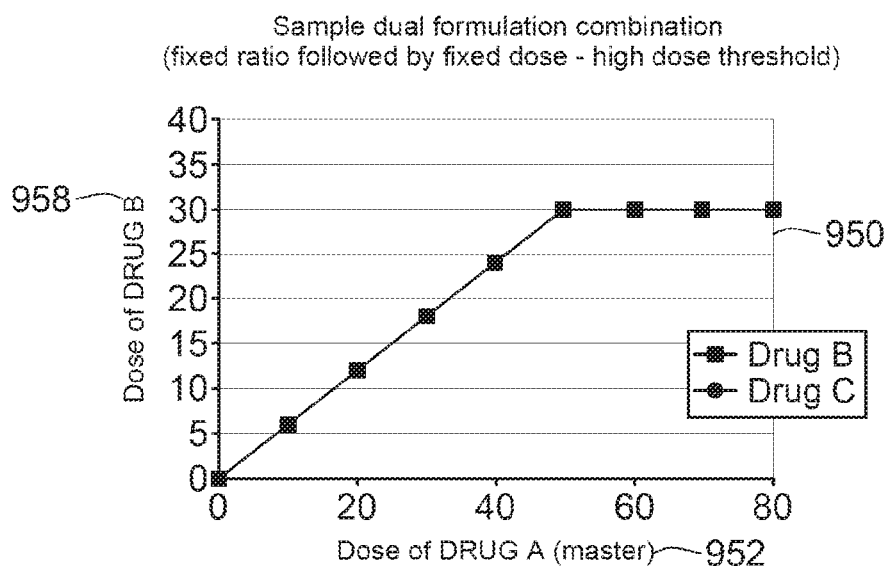
FIG. 41 illustrates an alternative arrangement of a predefined fixed ratio—fixed dose therapeutic profile having a high dose threshold and that may be programmed into the drug delivery device.
Figure 42:
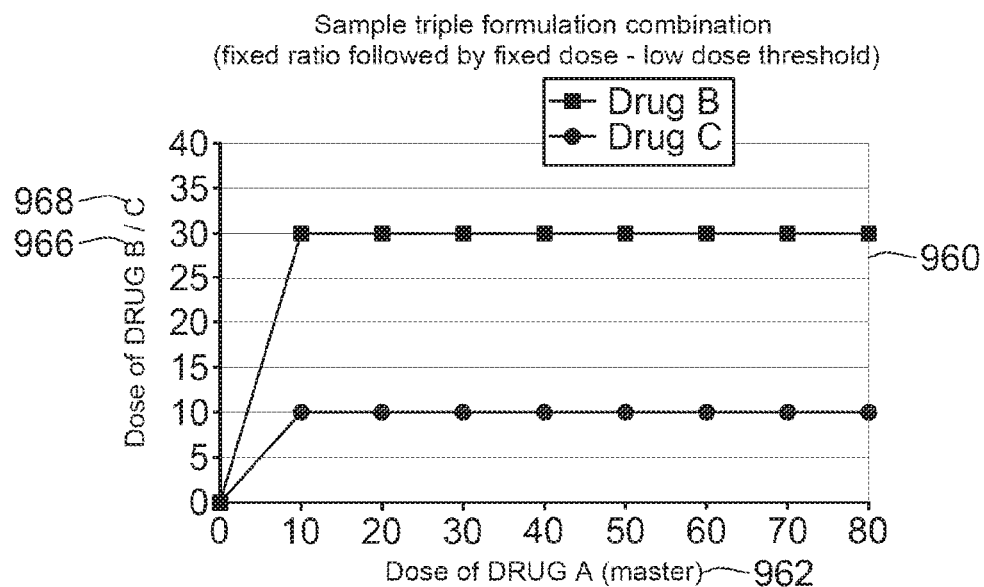
FIG. 42 illustrates an alternative arrangement of a predefined fixed ratio—fixed dose therapeutic profile having a low dose threshold and that may be programmed into a drug delivery device for use with at least three medicaments.

FIGS. 40-42 provide three illustrative examples of such fixed ratio followed by fixed dose—low dose threshold therapeutic profiles 940, 950, and 960. For example, FIG. 40 illustrates an arrangement of a predefined fixed ratio—fixed dose therapeutic profile 940 having a low dose threshold and that may be programmed into the drug delivery device. As illustrated, this profile 940 initially follows a fixed ratio profile for a 0-10 Unit selected doses of the primary medicament or Compound A 944. Then, once this 10 Unit threshold dose level of the Drug A has been surpassed, the profile 940 switches to a 30 Unit fixed dose of the secondary medicament or Compound B 948. As such, for doses greater than 10 Units of the primary medicament/Compound A 944, the secondary medicament 948 will comprise a fixed dose at 30 Units.

FIG. 41 illustrates an alternative arrangement of a predefined fixed ratio—fixed dose therapeutic profile 950 having a high dose threshold. As illustrated, this profile 950 initially follows a fixed ratio profile for a 0-50 Unit selected dose of the primary medicament or Compound A 952. Then, above this 50 Unit threshold dose level of the Drug A 952, the profile 950 switches to a 30 Unit fixed dose of the secondary medicament or Compound B 958. As such, for doses greater than 50 Units of the primary medicament/Compound A 952, the secondary medicament 958 will comprise essentially a fixed dose at 30 Units.

FIG. 42 illustrates an alternative arrangement of a predefined fixed ratio—fixed dose therapeutic profile having a low dose threshold and that may be programmed into the drug delivery device comprising three compounds or medicaments. As illustrated, this profile 960 initially follows a fixed ratio profile for both Drug B 966 and Drug C 968 for a 0-10 Unit selected dose of the primary medicament or Compound A 944. Then, above this 10 Unit threshold dose level of the Drug A, the profile 960 switches to a 30 Unit fixed dose of the secondary medicament or Compound B 966 and a 10 Unit fixed dose of the tertiary medicament Compound C 968. As such, for doses greater than 10 Units of the primary medicament/Compound A 944, the secondary and tertiary medicaments 966, 968 will comprise essentially fixed doses at 30 Units and 10 Units, respectively.

The profiles 940, 950, and 960 delivering a fixed ratio up to a first point and thereafter delivering a fixed dose type of profile in a combination drug delivery device provide a number of advantages. For example, where priming of the drug delivery device may be required (either for initial first time use, or prior to each dose), these types of a predefined fixed ratio—fixed dose therapeutic profiles facilitate priming of both compounds with potentially minimal wastage. In this regard, these profiles have certain advantages over other programmable therapeutic profiles, such as the fixed dose profiles and the delayed fixed dose profiles described herein below. This may be especially true with regards to wastage of the secondary medicament or Compound B.

In addition, the various profiles described and illustrated in FIGS. 40-42 may be appropriate in treatment situations where it is desirable to rapidly increase the dose of the secondary medicament, relative to the primary medicament initially. However, once a preset dose threshold has been reached, the secondary medicament may be kept constant regardless of further increases in the dose of the primary medicament. As such, this type of profile might be beneficial for drug delivery devices where an initial titration phase (of both drug compounds) is either required, or is deemed preferable for a patient.

An example of a particular combination therapy where profiles 940, 950 and 960 might be appropriate is for the combined delivery of a long acting insulin or insulin analog (i.e., Drug A or the primary medicament) in combination with an active agent, such as a GLP-1 or GLP-1 analog (i.e., Drug B or the secondary medicament). In this particular combination therapy, there is a reasonable variation in the size of the insulin dose across patient population, whereas the therapeutic dose of the GLP-1 may be considered as broadly constant (except during the titration phase) across the patient population.

Another preferred dose profile for use with the drug delivery device 10 comprises a fixed dose of the secondary medicament (i.e., Compound B) and a variable dose of the primary medicament (i.e., Compound A) profile. With such a therapeutic profile, the profile describes the delivery of a fixed dose of Compound B across the full range of potential doses of Compound A.

This fixed dose—variable dose therapeutic profile may be beneficial for the dose of Compound B to be constant for all potential doses of Compound A. One advantage of having the control unit programmed with such a profile is that fixed dose—variable dose therapeutic profiles are not achievable from a combination drug that is co-formulated into a single primary pack (such as, but not limited to, a standard 3 ml glass cartridge) where the concentration of the various constituent parts is constant (xmg/ml).

Figure 43:
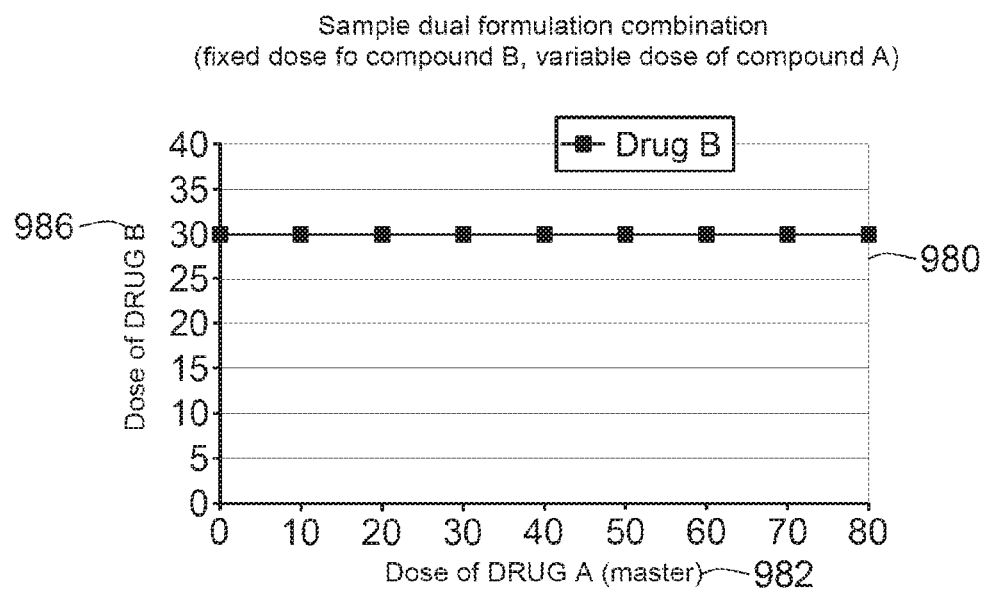
FIG. 43 illustrates an arrangement of a predefined fixed dose—variable dose therapeutic profile that may be programmed into the drug delivery device.
Figure 44:
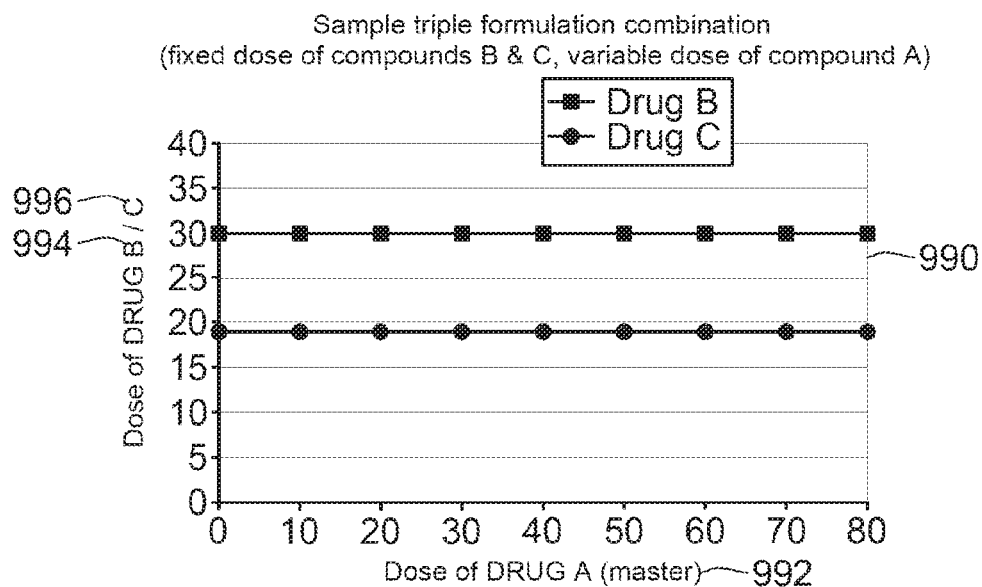
FIG. 44 illustrates an alternative arrangement of a predefined fixed dose—variable dose therapeutic profile that may be programmed into the drug delivery device and for use with at least three medicaments.

Two such fixed dose—variable dose profiles are illustrated in FIGS. 43-44. FIG. 43 illustrates an arrangement of a predefined fixed dose—variable dose therapeutic profile 980 that may be programmed into the drug delivery device. More specifically, FIG. 43 illustrates a sample formulation combination for a fixed dose of Compound B 986 and a variable dose of compound A 982. As illustrated, for any selected dose of the primary medicament 982, a fixed dose of 30 Units of Drug B 986 will be computed.

FIG. 44 illustrates an alternative arrangement of a predefined fixed dose—variable dose therapeutic profile 990 that may be programmed into the drug delivery device. As illustrated, profile 990 provides for a sample triple formulation combination of a fixed dose of Drug B 994 and Drug C 996 and a variable dose of Drug A 992. As illustrated, for any selected dose of the primary medicament 992, a fixed dose of 30 Units of Drug B 994 and a fixed dose of 18 Units of Drug C 996 will be computed by the drug delivery device 10.

Such fixed dose—variable dose profiles 980 and 990 offer a number of advantages. For example, one of the benefits of these types of delivery profiles is in treatment situations where it is therapeutically desirable to ensure that patients receive a specific dose of one drug compound, irrespective of the size of the variable dose selected of the other compound. This particular profile has specific advantages over other predefined profiles (e.g., the fixed ratio then fixed dose profiles described above, the delayed fixed dose of compound B, variable dose of compound A profiles described below and the controlled thresholds profiles described below), there is not a predetermined minimum dose threshold of primary medicament required to ensure a complete dose of the secondary medicament.

One example of a particular combination therapy where this type of fixed dose-variable dose profile might be particularly appropriate is for the combined delivery of a long acting insulin (i.e., the variable dose) with a GLP-1 (i.e., the fixed dose). In this particular combination, there is reasonable variation in the size of the insulin dose across the patient population, whereas the GLP-1 dose is broadly constant (except during the titration phase where it generally increases in stepped intervals) across the patient population. For this particular therapy regimen, titration of the GLP-1 dose may be needed during the early stages of treatment. This could be achieved with a combination device using different 'strengths' of drug within the GLP-1 primary pack (e.g., using 10, 15 or 20 g per 0.1 ml concentrations).

For certain therapies it might be beneficial for the dose of secondary medicament Compound B to be a constant dose once a minimum threshold dose of the primary medicament Compound A has been met and/or exceeded. Again, such profiles of this type are not achievable from a combination drug that is co-formulated into a single reservoir or cartridge (such as, but not limited to, a standard 3 ml glass cartridge). In such standard cartridges, the concentration of the various constituent parts is constant (xmg/ml).

In one arrangement, the drug delivery device 10 may also be programmed with a therapeutic profile that calculates a delayed fixed dose of a secondary medicament Compound B and variable dose of a primary medicament Compound A. Such a profile provides for the delivery of a fixed dose of Compound B but provides this fixed dose only after a minimum threshold dose of Compound A has been met or exceeded. Illustrative examples of four predefined delayed fixed dose—variable dose therapeutic profiles 1000, 1020, 1040 and 1060 are illustrated in FIGS. 45-48.

Figure 45:
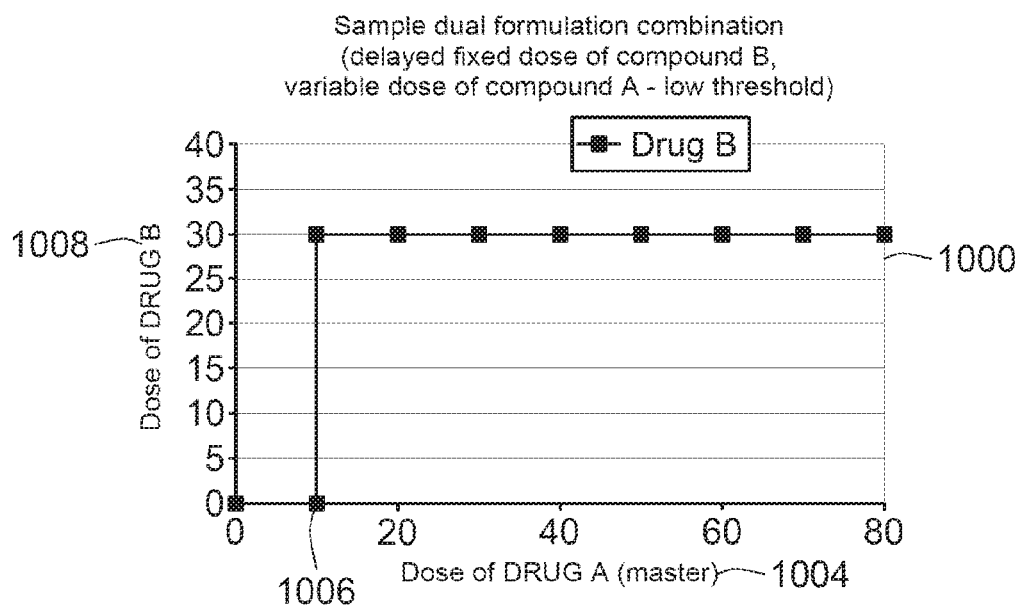
FIG. 45 illustrates an arrangement of a predefined delayed fixed dose—variable dose therapeutic profile having a low threshold and that may be programmed into the drug delivery device.

For example, FIG. 45 illustrates an arrangement of a predefined delayed fixed dose—variable dose therapeutic profile 1000 having a low threshold. More specifically, FIG. 45 illustrates a sample dual formulation combination having a delayed fixed dose of the secondary medicament (i.e., Compound B) and a variable dose of the primary medicament (i.e., Compound A) with the primary medicament having a low dose threshold 1006.

As illustrated in FIG. 45, the profile 1000 defines a variable dose of Drug A 1004 from a minimum dose of 0 Units to a maximum dose of 80 Units. In this illustrative profile 1000, the low threshold 1006 for Drug A 1004 is 10 Units. Based on profile 1000, if a user were to select a dose of Drug A 1004 anywhere from 0 to 10 Units, the control unit would calculate a dose of Drug B 1008 equal to "0" Units. Only after a minimum or threshold dose of 10 units were selected for the primary medicament 1004, would a dose of Drug B 1008 be calculated above "0" Units. Moreover, this calculated dose of Drug B 1008 would be a constant 30 Units, irrespective of the amount of the selected dose set of Drug A 1004, as long as this selected dose remains greater than 10 Units.

Figure 46:
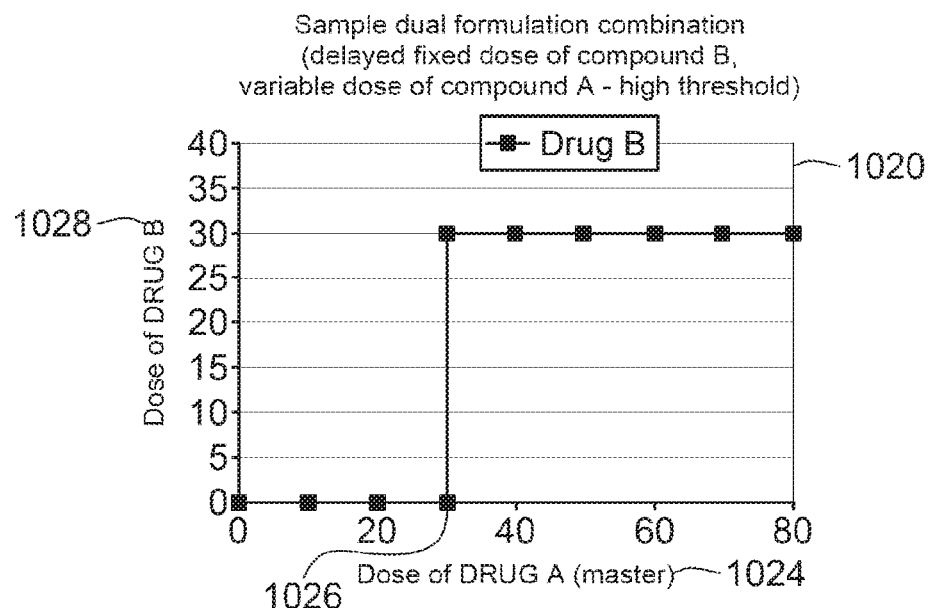
FIG. 46 illustrates an arrangement of a predefined delayed fixed dose—variable dose therapeutic profile having a high threshold and that may be programmed into the drug delivery device.

FIG. 46 illustrates an arrangement of a predefined delayed fixed dose—variable dose therapeutic profile 1020 having a high threshold of Drug A 1024. More specifically, FIG. 46 illustrates a profile 1020 for defining a dual formulation combination having a delayed fixed dose of Compound B 1028 and a variable dose of Compound A 1024. In this illustrative profile 1020, the high threshold 1026 for Drug A 1024 is 30 Units. This high initial threshold 1026 of Drug A 1024 is required before the profile 1020 allows a dose to be set from Drug B 1028. In this illustrated profile 1020, this high initial threshold 1026 equal to 30 Units of Drug A 1024 must be surpassed before the delivery device 10 begins to calculate a 30 Unit dose of Drug B 1028.

Figure 47:
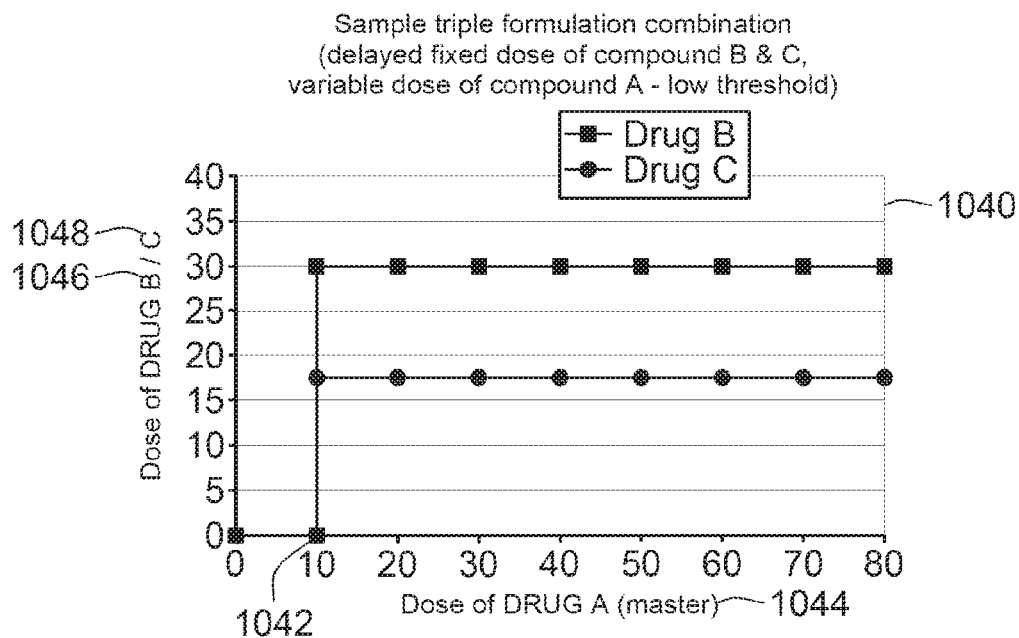
FIG. 47 illustrates an alternative arrangement of a predefined delayed fixed dose—variable dose therapeutic profile having a low dose threshold and that may be programmed into the drug delivery device.

FIG. 47 illustrates an alternative arrangement of a predefined delayed fixed dose—variable dose therapeutic profile 1040 wherein the drug delivery device 10 comprises two compounds or medicaments. More particularly, FIG. 47 illustrates a profile 1040 for defining a sample triple formulation combination having a delayed fixed dose of Drug B 1046 and Drug C 1048, a variable dose of Drug A 1044 wherein this Drug A 1044 has a low threshold. In this illustrated profile 1040, Drug A 1044 has a low threshold 1042 equal to 10 Units. That is, once a user equals or surpasses the low threshold 1042 of 10 Units of Drug A 1044, the drug delivery device 10 will calculate a dose of 17.5 Units of Drug C 1048 and calculate a dose of 30 Units of Drug B 1046.

Figure 48:
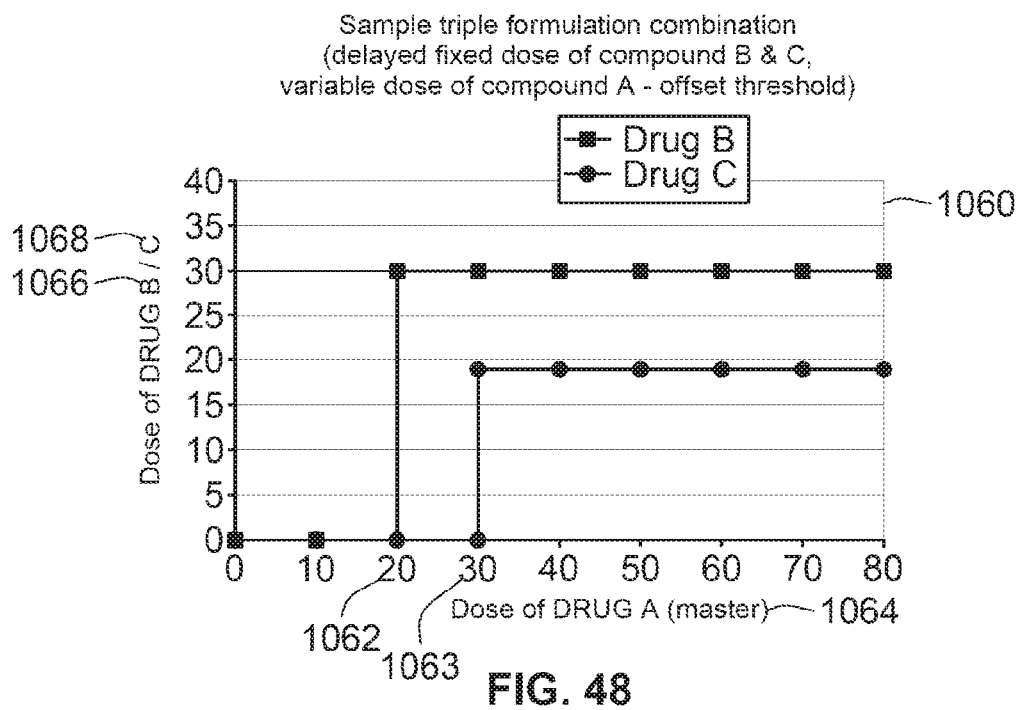
FIG. 48 illustrates an arrangement of a predefined delayed fixed dose—variable dose therapeutic profile having offset dose thresholds and that may be programmed into the drug delivery device.

FIG. 48 illustrates a profile 1060 that defines a sample triple formulation combination having a delayed fixed dose of Drug B 1066 and Drug C 1068, and a variable dose of Drug A 1064. In profile 1060, the primary medicament Drug A has two offset thresholds 1062, 1063. That is, once the user selects a dose that surpasses the low threshold 1062 of 20 Units of Drug A 1064, the drug delivery device 10 will calculate a dose of 30 Units for Drug B 1066 and will calculate a dose of "0" Units for Drug C 1068.

Similarly, if a user selects a dose of Drug A 1064 between 20 Units and 30 Units, again the drug delivery device 10 will calculate a dose of 30 Units for Drug B 1066 and calculate a dose of "0" Units for Drug C 1068. Then, it is only after a user selects a dose greater than 30 Units for Drug A 1064 thereby surpassing the second threshold 1063, the drug delivery device 10 will the calculate a dose of Drug C 1068. In this illustrated profile 1060, this dose of Drug C 1068 equals 19 Units. Although only two offset thresholds are illustrated in this profile 1060, those of skill in the art will recognize alternative threshold arrangements may also be utilized.

The preferred profiles 1000, 1020, 1040, and 1060 illustrated in FIGS. 45-48 offer a number of advantages. For example, these illustrated profiles could provide the basis for a single device solution where it is therapeutically desirable to ensure that a patient using the drug delivery device 10 receives a specific, calculated dose of one drug compound in conjunction with the dose they select of another drug compound. However, the patient would receive such specific, calculated doses of the second compound only once a minimum dose threshold (of a primary drug or Drug A) has been reached or surpassed. As such, these illustrated profiles 1000, 1020, 1040, and 1060 could provide a cost-effective solution where a user's prescribed therapy requires that the primary medicament needs to be titrated up to a minimum value reasonably quickly before it should be taken in combination with a secondary medicament (and perhaps other medicaments), therefore rendering at least a two device option more costly and/or wasteful. Such a two device option may be more costly and/or wasteful as the device containing Drug A may be only part utilized at the point where the patient switches to the combination product.

An additional benefit stems from the situation that patients are sometimes required to carry out a priming step with their drug delivery device. Such a priming step may be required either prior to a first use of the drug delivery device or perhaps prior to each time a dose is to be administered by the drug delivery device. In the example of pen type drug delivery devices, one of the principle reasons for the set up prime is to remove clearances/backlash in the mechanism, thereby helping ensure that the first dose delivered is within the required dose accuracy range. The in-use prime (sometimes referred to in certain relevant art and/or literature as a "safety shot") is recommended for some pen type drug delivery devices. For example, such a safety shot may be recommended so as to confirm that the dose setting mechanism within the device is functioning properly. Such a safety shot is also often recommended so as to confirm that the delivered dose is accurately controlled and also to ensure that the attached dose dispenser (e.g., double ended needle assembly) is not blocked. Certain safety shots also allow the user to remove air from the dose dispenser prior to a user setting and therefore administering a dose. For a multi primary pack device, a profile of this type would enable the 'in use safety' prime to be undertaken using primary medicament only, thereby minimizing potential wastage of the secondary medicament.

For example, a particular combination therapy where this type of profile might be particularly appropriate is for the combined delivery of a long acting insulin or insulin analog along with a GLP-1 or a GLP-1 analog for early-stage diabetics. For example, there is a reasonably large variation in the size of the insulin doses across patient population, whereas GLP1 doses are broadly constant (except during the titration phase where is generally increases in stepped intervals) across the patient population. For this particular type of combination therapy, titration of the GLP1 dose is needed during the early stages of treatment. This could be achieved with a combination device through the use different 'strengths' of drug within the GLP1 cartridge or reservoir (e.g. using 10, 15 or 20 g per 0.2 ml concentrations for instance). The proposed delivery profiles illustrated in FIGS. 45-48 would enable the user to perform a safety shot of the long acting insulin only without wasting GLP1. In this example the accuracy of the insulin dose is the more important than the accuracy of the GLP1 dose which is why performing the safety shot with insulin only is preferred.

As previously described, the delivery of combination drug products (i.e., single doses that are made up from the combination of two or more individual drug formulations) in a format where the delivered dose profile is predefined, offers a number of key benefits for both a patient and the treatment of a particular condition. For certain therapies it might be beneficial for the dose of the secondary medicament to increase in fixed stepped increments as the corresponding dose of primary medicament increases, but for each of these stepped increases to only occur once a specific predefined threshold dose of primary medicament has been exceeded. The relative 'spacing' between these threshold values of the primary medicament may or may not be regular. Again, such profiles of this type are not achievable from a combination drug that is co-formulated into a single primary pack (such as, but not limited to, a standard 3 ml glass cartridge) where the concentration of the various constituent parts is constant. Two exemplary profiles 1080 and 1100 are illustrated in FIGS. 49 and 50, respectively.

Figure 49:
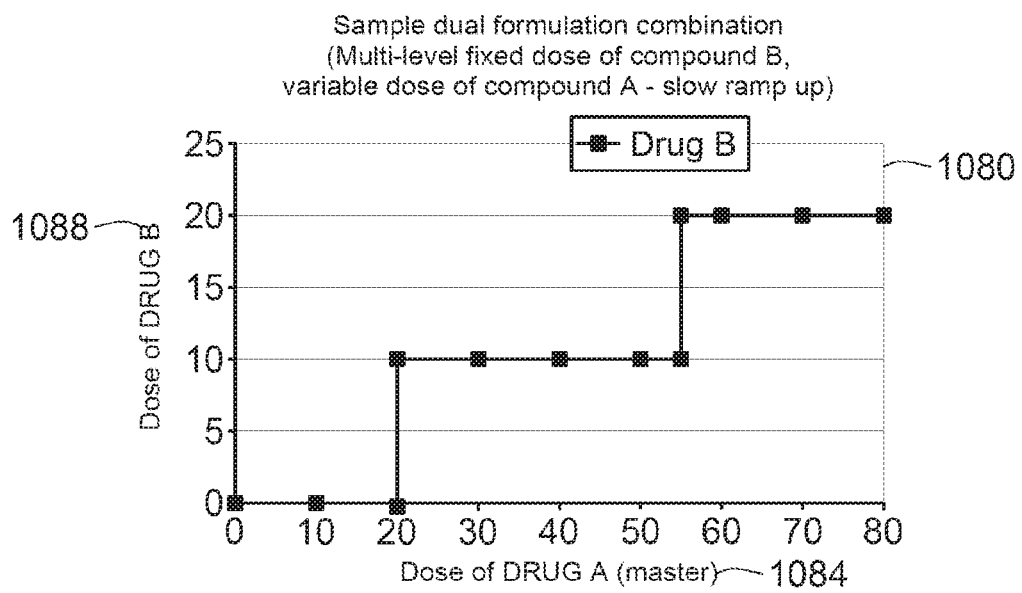
FIG. 49 illustrates an arrangement of a predefined multi-level fixed dose—variable dose therapeutic profile having a slow ramp up and that may be programmed into the drug delivery device.

For example, FIG. 49 illustrates an arrangement of a predefined multi-level fixed dose—variable dose therapeutic profile 1080 that comprises a slow ramp up and that may be programmed into the drug delivery device 10. Specifically, FIG. 49 illustrates a sample dual formulation having a multi-level fixed dose of Drug B 1088 and having a variable dose of Drug A 1084 and a slow ramp up.

This particular delivery profile could provide the basis for a single device solution where it is therapeutically desirable for the dose of the secondary medicament to increase in a stepped (rather than linear) manner as the dose of primary medicament is increased. This may be related to the specific safety and efficacy characteristics of a prescribed therapy, or situations where titration of the secondary medicament is stepped, as is the case for the injection of GLP1 type drugs (for the treatment of early stage, Type II diabetes).

Figure 50:
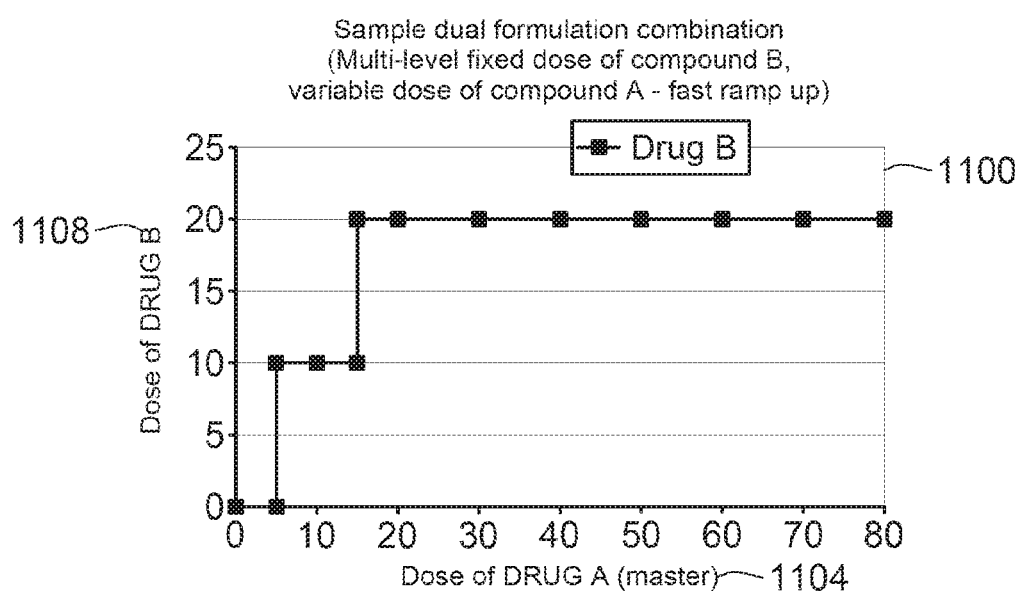
FIG. 50 illustrates an arrangement of a predefined multi-level fixed dose—variable dose therapeutic profile having a fast ramp up and that may be programmed into the drug delivery device.

FIG. 50 illustrates an alternative profile 1100 for defining a predefined multi-level fixed dose—variable dose therapeutic and that may be programmed into the drug delivery device 10. As illustrated, this particular predefined multi-level fixed dose—variable dose therapeutic profile comprises a quick ramp up. In this preferred profile 1100, a multi-level fixed dose of Drug B 1108 and a variable dose of Drug A 1104 profile is shown. In this case, the profile 1100 describes the delivery of stepped fixed doses of Drug B once corresponding threshold doses of Drug A have been exceeded. The illustrated profiles in FIGS. 49 and 50 have certain potential benefits in terms of splitting a set and calculated combined dose. In addition to the previously discussed advantages, it has been acknowledged that users of drug delivery devices (such as pen type drug delivery devices) may sometimes split their target dose into two, smaller doses. This may occur as a patient transitions from a device that is nearly empty to a replacement device, or because the delivery of a 'large' dose as a singular event is problematic (even painful). For single formulation devices, or combination device where the various constituent elements are delivered in a fixed ratio to each other, splitting a dose into smaller parts does not affect the dose that is ultimately received. However, for combination devices where a patient receives a fixed dose of one medicament irrespective of the selected dose of the primary medicament as previously described, splitting a dose could result in an overdose of one of the individual medicaments. The careful utilization of this type of multi-level profile, however, can provide a reasonably robust solution to this particular user scenario.

As just one example, consider a patient who generally takes between 50 and 80 units of Drug A (e.g., an insulin or insulin analog), and whose target dose of Drug B (e.g., a GLP-1 or GLP-1 analog) is 20 units. Assuming that the patient has been prescribed with a device utilizing the therapeutic profile detailed in FIG. 49, then their target prescription would be achieved if each dose is administered as a single injection. This would not be the case where the patient decides to split their target dose into two smaller doses. In an example embodiment, the device may determine that the two subsequent injections are split injections of a single target dose, for example by determining that a cartridge of one of the medicaments was changed, or by determining that only a small amount of time has passed since the last injection, for example less than 30 minutes. Referring to the profile of FIG. 49, a patient may want to administer a dose of 50 units of drug A. The device would determine that a dose of 10 units of drug B corresponds to a dose of 50 units of drug A. However, in a first injection, 25 units of drug A are selected, for example as the cartridge only contains a remainder of 25 units. The device determines according to the profile 10 units of drug B. 5 minutes later (for example after exchanging the cartridge) another 25 units of drug A are selected. As the time since the last injection is less than the threshold of 30 minutes, the device determines that the new selection of 25 units is a second dose of a split dose of drug A of 50 units. Therefore, the device determines the dose of drug B for the second injection to be 0 units, as 50 units of drug A will result in 10 units of drug B according to profile 1080, and as 10 units of drug B have already been administered in the first injection of the split dose.

The electro-mechanical dose setting mechanism is of particular benefit where a targeted therapeutic response can be optimized for a specific target patient group. This may be achieved by a microprocessor based drug delivery device that is programmed to control, define, and/or optimize at least one therapeutic dose profile. A plurality of potential dose profiles may be stored in a memory device operatively coupled to the microprocessor. For example, such stored therapeutic dose profiles may include, but are not limited to, a linear dose profile; a non-linear dose profile; a fixed ratio fixed dose profile; a fixed dose variable dose profile; a delayed fixed dose variable dose profile; or a multi-level, fixed dose variable dose profile as discussed and described in greater detail below. Alternatively, only one dose profile would be stored in a memory device operatively coupled to the microprocessor. In one dual medicament drug delivery device arrangement, the dose of the second medicament may be determined by way of a first therapeutic profile such as those identified above. In one drug delivery device comprising three medicaments, the dose of the second medicament may be determined by way of a first therapeutic profile while the dose of the third medicament may be determined by either the same first therapeutic profile or a second different therapeutic profile. As those of ordinary skill in the art will recognize, alternative therapeutic profile arrangements may also be used.

Exemplary embodiments of the present invention have been described. Those skilled in the art will understand, however, that changes and modifications may be made to these embodiments without departing from the true scope and spirit of the present invention, which is defined by the claims.

What is claimed is:

1. A drug delivery device comprising:
   a motor configured to advance a stopper in a cartridge of medicament, the motor comprising an output shaft;
   a controller;
   a motion detection system configured to provide positional feedback to the controller, the motion detection system comprising an optical encoder and at least one element operatively coupled to the output shaft of the motor and configured to rotate with the output shaft such that the at least one element passes through the optical encoder;
   a piston rod mechanically linked to the motor, the piston rod being moveable between a first fully withdrawn position and a second fully extended position; and
   a hinged cartridge retainer rotatable about a pivot point between an open position and a closed position and configured to receive a cartridge of medicament, wherein the cartridge retainer can only be opened when the piston rod is in the first fully withdrawn position.

2. A drug delivery device according to claim 1, wherein the optical encoder is configured to send electrical pulses to the controller as the at least one element passes through the optical encoder.

3. A drug delivery device according to claim 1, wherein the at least one element is a plurality of elements symmetrically spaced around a cylindrical axis of the output shaft.

4. A drug delivery device according to claim 1, further comprising a pinion operatively coupled to the output shaft, wherein the pinion includes the at least one element of the motion detection system.

5. A drug delivery device according to claim 1, wherein the controller is configured to monitor a rotation of the output shaft and to detect a position error of the motor.

6. A drug delivery device according to claim 1, wherein the controller is configured to monitor a rotation of the output shaft and to detect a jamming of a drive train of the drug delivery device.

7. A drug delivery device according to claim 1, wherein the controller is configured to monitor a rotation of the output shaft and to detect a blocked needle event.

8. A drug delivery device according to claim 1, wherein the at least one element comprises a plurality of flags protruding radially from the output shaft of the motor.

9. A drug delivery device according to claim 8, wherein the plurality of flags comprises a first flag and a second flag.

10. A drug delivery device according to claim 1, wherein the motor is a stepper motor.

11. A drug delivery device according to claim 1, wherein the motor is a brushless DC motor.

12. A drug delivery device according to claim 1, wherein the drug delivery device further comprises one or more switches configured to determine a position of the stopper in the cartridge of medicament.

13. A drug delivery device according to claim 1, wherein the drug delivery device further comprises an end stop switch configured to detect when the piston rod is in the first fully withdrawn position.

14. A drug delivery device according to claim 1, wherein the drug delivery device further comprises an electronic cartridge detection system configured to determine if the cartridge of medicament has been inserted into the cartridge retainer.

15. A drug delivery device according to claim 14, wherein the electronic cartridge detection system is configured to detect a drug type contained in the cartridge of medicament.

16. A drug delivery device according to claim 1, wherein the controller is configured to automatically rewind the piston rod from the second fully extended position to the first fully withdrawn position.

17. A drug delivery device according to claim 1, wherein the optical encoder is attached to a gearbox housing.

* * * * *

SEQUENCE LISTING

```
<160> NUMBER OF SEQ ID NOS: 2

<210> SEQ ID NO 1
<211> LENGTH: 39
<212> TYPE: PRT
<213> ORGANISM: Artificial Sequence
<220> FEATURE:
<223> OTHER INFORMATION: Exendin-4(1-39) amino acid sequence

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 45
<212> TYPE: PRT
<213> ORGANISM: Artificial Sequence
<220> FEATURE:
<223> OTHER INFORMATION: AVE0010 amino acid sequence

<400> SEQUENCE: 2
```

-continued

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25              30

Ser Gly Ala Pro Pro Pro Ser Lys Lys Lys Lys Lys Lys
        35              40              45
```